(12) United States Patent
Roth et al.

(10) Patent No.: US 7,923,445 B2
(45) Date of Patent: Apr. 12, 2011

(54) METHODS FOR TREATMENT OF DISEASES RELATED TO ACTIVATED LYMPHOCYTES

(75) Inventors: Stephen Roth, Gladwyne, PA (US);
Clayton Buck, Berwyn, PA (US);
Christopher Self, West Caldwell, NJ (US); Gary Olson, Mountainside, NJ (US)

(73) Assignee: Immune Control, Inc., West Conshohocken, PA (US)

( * ) Notice: Subject to any disclaimer, the term of this patent is extended or adjusted under 35 U.S.C. 154(b) by 510 days.

(21) Appl. No.: 11/897,669

(22) Filed: Aug. 31, 2007

(65) Prior Publication Data

US 2008/0125415 A1  May 29, 2008

Related U.S. Application Data

(60) Provisional application No. 60/841,771, filed on Sep. 1, 2006.

(51) Int. Cl.
*A01K 31/54* (2006.01)
*A01K 31/497* (2006.01)

(52) U.S. Cl. .............. 514/222.2; 514/224.5; 514/254.08; 514/253.01

(58) Field of Classification Search .............. 514/222.2, 514/224.5, 254.08, 253.01
See application file for complete search history.

(56) References Cited

U.S. PATENT DOCUMENTS

| 2,645,640 A | 7/1953 | Charpentier |
| 2,687,414 A | 8/1954 | Cusic |
| 2,957,870 A | 10/1960 | Cusic |
| 3,058,979 A | 10/1962 | Ullyot |
| 3,194,733 A | 7/1965 | Yale et al. |
| 5,595,989 A | 1/1997 | Andersen et al. |
| 6,333,322 B1 | 12/2001 | Miyamoto et al. |
| 6,815,450 B2 | 11/2004 | He et al. |
| 2003/0032801 A1 | 2/2003 | Lin et al. |
| 2005/0080075 A1 | 4/2005 | Nichols et al. |

FOREIGN PATENT DOCUMENTS

| EP | 0 889 037 | 1/1999 |
| FR | 2.218.102 | 9/1974 |
| GB | 824598 | 12/1959 |
| GB | 857547 | 12/1960 |
| GB | 903725 | 8/1962 |
| WO | WO 02/089810 | 11/2002 |
| WO | WO 03/062388 | 7/2003 |
| WO | 03/106660 | 12/2003 |
| WO | WO 03/106660 | 12/2003 |

OTHER PUBLICATIONS

Achour et al. Virology 315 (2003) 245-258.*
Aune et al., 1990, J. Immunol. 145:1826-1831.
Aune et al., 1993, J. Immunol. 151:1175-1183.
Aune et al., 1994, J. Immunol. 153:1826-1831.
Foon et al., 1976, J. Immunol. 117:1545-1552.
Khan et al., 1986, Int. Arch. Allergy Appl. Immunol. 81:378-380.
Kut et al., 1992, Immunopharmacol. Immunotoxicol. 14:783-796.
Mossner & Lesch, 1998, Brain, Behavior, and Immunity 12:249-271.
Slauson et al., 1984, Cell. Immunol. 84:240-252.
Young et al., 1993, Immunology 80:395-400.
Dahlbom, "Antihistamine Agents", 1949, ACTA Chemica Scandinavica, 3:247-255.
USPTO, Office Action dated May 3, 2010 for U.S. Appl. No. 11/897,598, filed Aug. 31, 2007.
Supplemental European Search Report for European Application No. 07811633.2, dated Sep. 8, 2010.
Hromatka et al., XP009137937, Jan. 1, 1962, pp. 1288-1293.
USPTO, Office Action dated Sep. 2, 2010 for U.S. Appl. No. 11/897,598, filed Aug. 31, 2007.
Nieschuz et al., Arzneimittel-Forschung (1957), vol. 7, pp. 106-113.

\* cited by examiner

*Primary Examiner* — Brandon J Fetterolf
*Assistant Examiner* — Shirley V Gembeh
(74) *Attorney, Agent, or Firm* — Riverside Law LLP

(57) ABSTRACT

The present invention relates to inhibiting proliferation and inducing apoptosis in activated lymphocytes, including T cells and B cells. The invention also provides compositions and methods for inhibiting proliferation and inducing apoptosis in activated lymphocytes, as well methods for treating diseases associated with activated lymphocytes by administering 5-HT receptor antagonists.

11 Claims, 36 Drawing Sheets

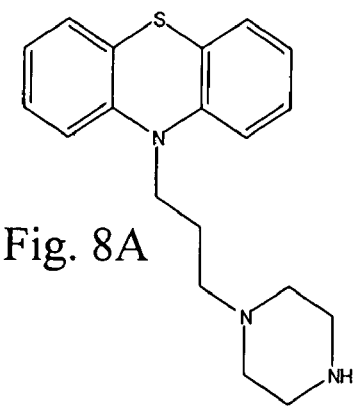
Fig. 8A
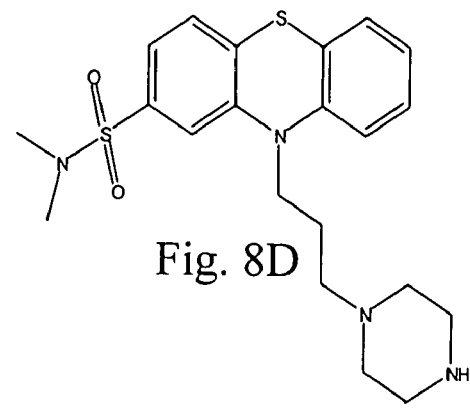
Fig. 8D
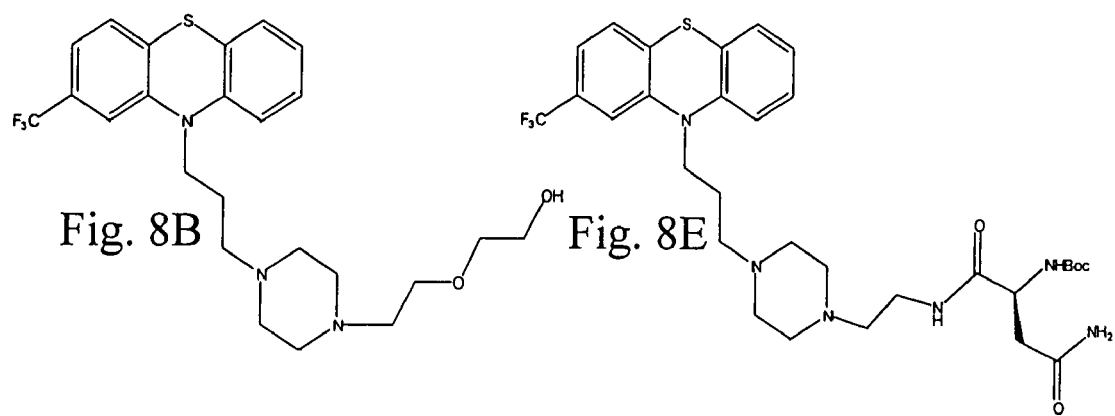
Fig. 8B
Fig. 8E
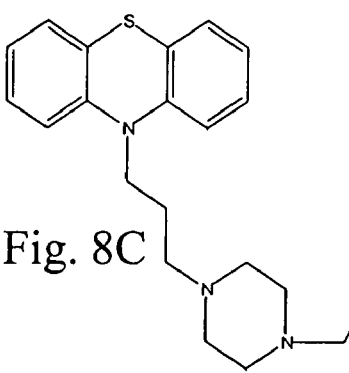
Fig. 8C
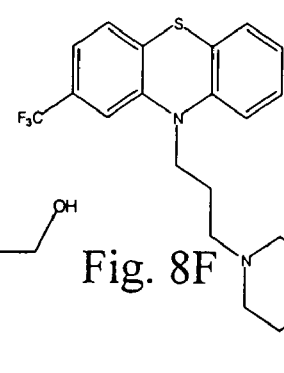
Fig. 8F

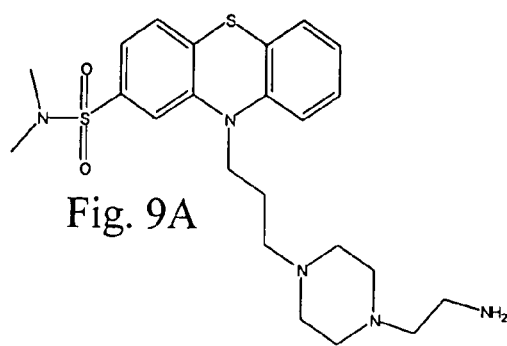
Fig. 9A
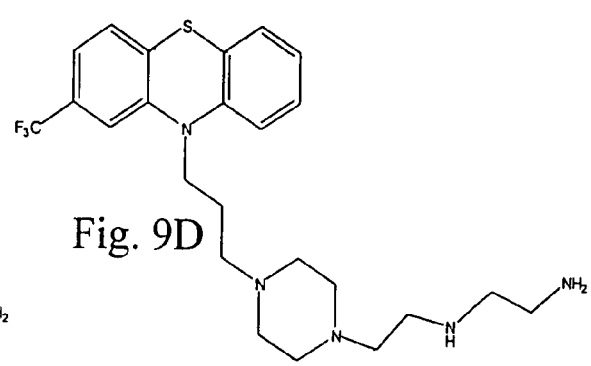
Fig. 9D
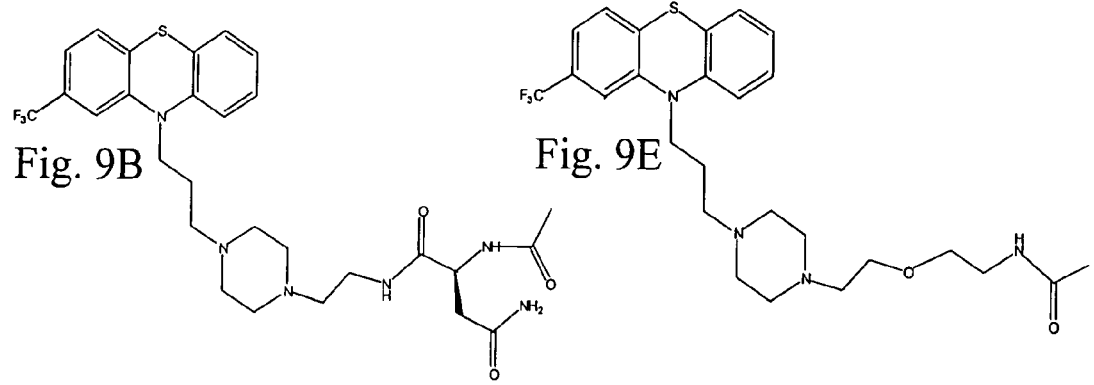
Fig. 9B
Fig. 9E
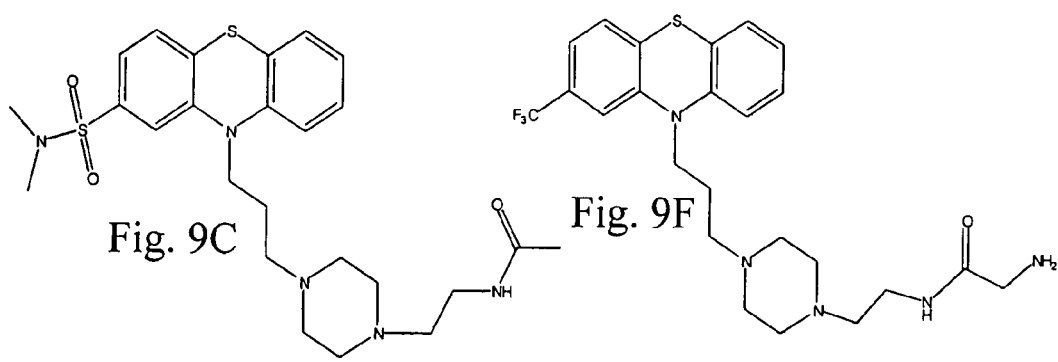
Fig. 9C
Fig. 9F

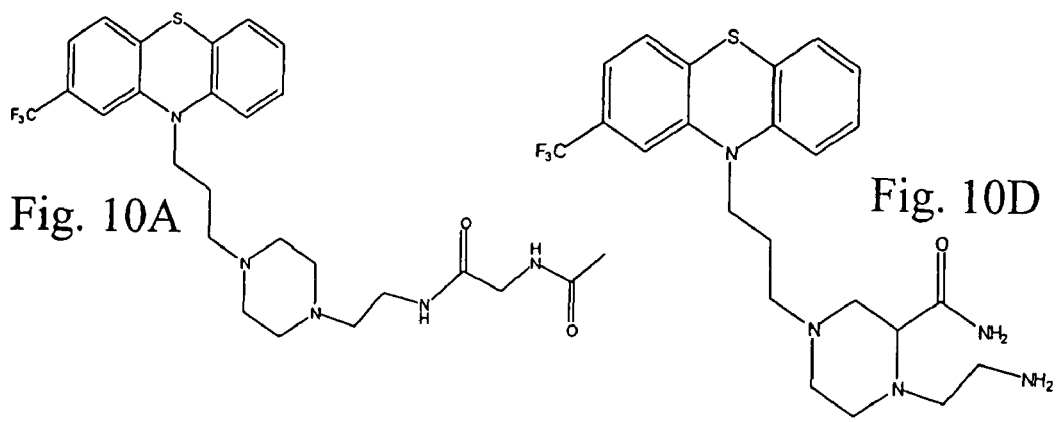
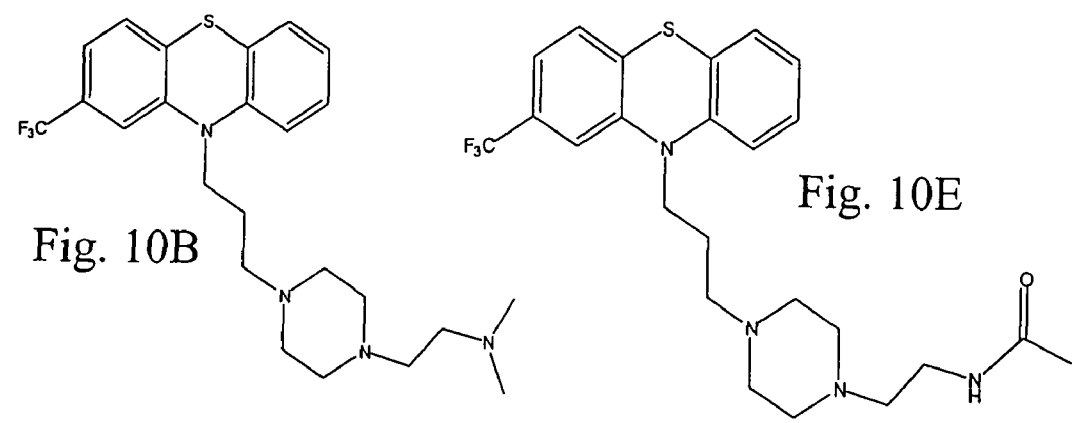
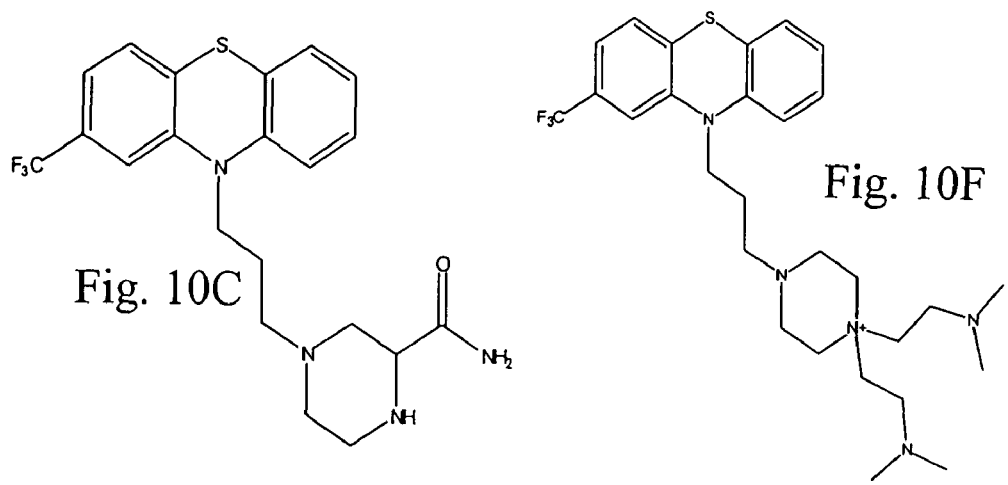

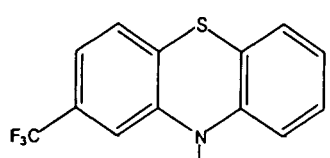
Fig. 11A
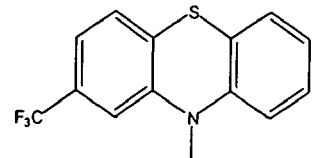
Fig. 11D
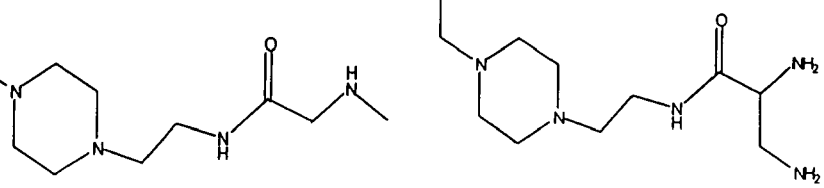
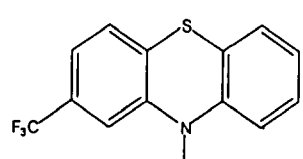
Fig. 11B
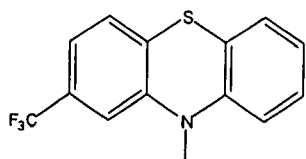
Fig. 11E
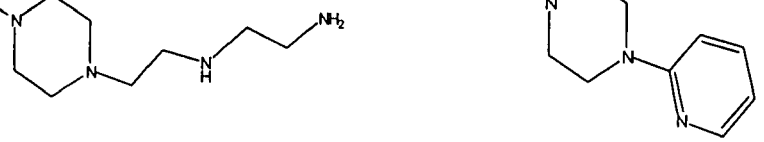
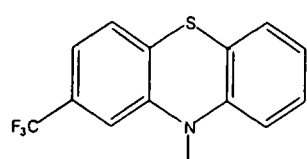
Fig. 11C
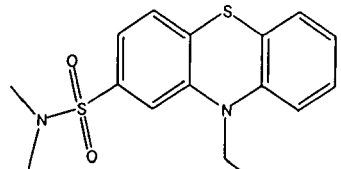
Fig. 11F
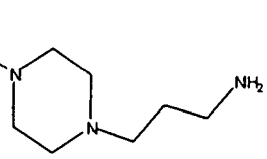

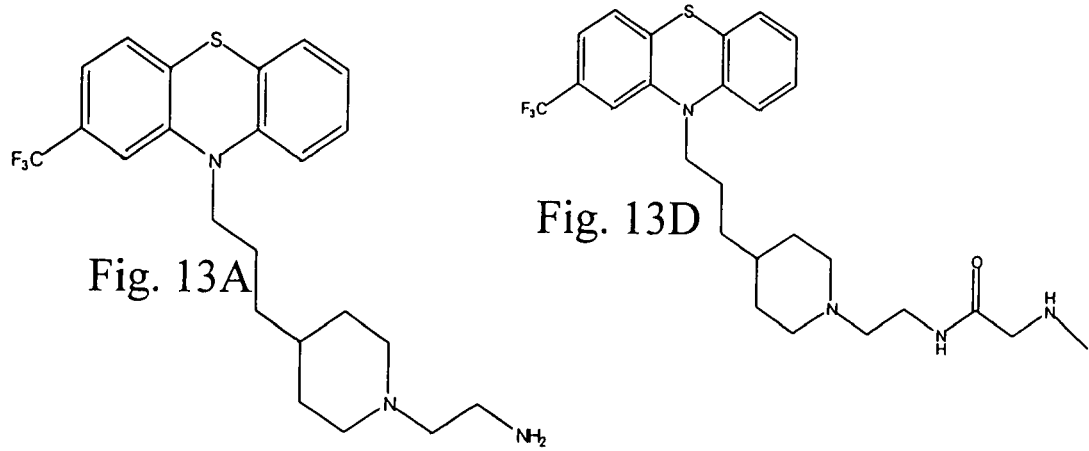
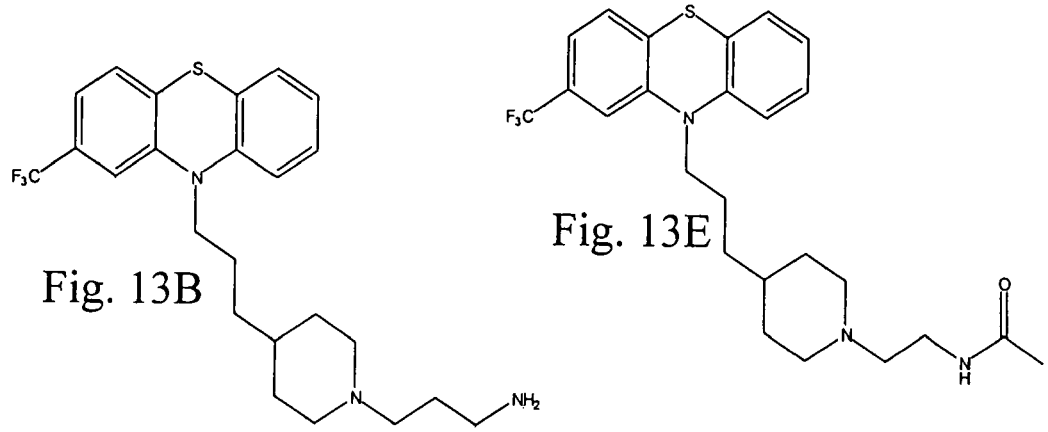
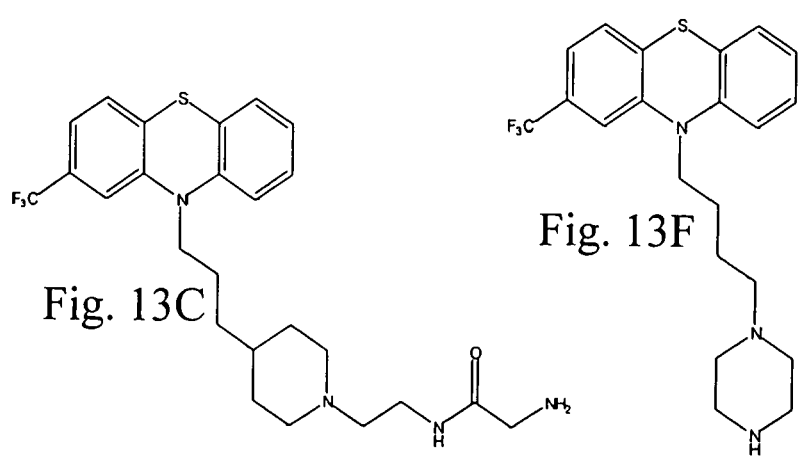
Fig. 13A Fig. 13B Fig. 13C Fig. 13D Fig. 13E Fig. 13F compound 15: n=2, m=1, R$_1$=Boc compound 16: n=2, m=2, R$_1$=Boc compound 19: n=2, m=1, R$_1$=(CO)CH$_2$NMe(Boc)

compound 29: n=1, m=1, R$_1$=Boc

Other Intermediates

Synthetic route to ICI-954

Synthetic route to ICI-1008

METHODS FOR TREATMENT OF DISEASES RELATED TO ACTIVATED LYMPHOCYTES

CROSS-REFERENCE TO RELATED APPLICATIONS

The present application is entitled to priority under 35 U.S.C. §119(e), to U.S. Provisional Application No. 60/841,771 filed on Sep. 1, 2006, which application is hereby incorporated herein by reference in its entirety.

BACKGROUND OF THE INVENTION

Serotonin (also referred to as 5-hydroxytryptamine or 5-HT) is a neurotransmitter that has been strongly implicated in the pathophysiology and treatment of a wide variety of neuropsychiatric disorders. Serotonin exerts its effects through a diverse family of serotonin receptor molecules (referred to herein as "5-HT receptors" or "5-HTRs"). Classically, members of the serotonin receptor family have been grouped into seven (7) subtypes pharmacologically, i.e., according to their specificity of various serotonin antagonists. Thus, while all the 5-HT receptors specifically bind with serotonin, they are pharmacologically distinct and are encoded by separate genes. To date, fourteen (14) mammalian serotonin receptors have been identified and sequenced. More particularly, these fourteen separate 5-HT receptors have been grouped into seven (7) pharmacological subtypes, designated 5-HT1, 5-HT2, 5-HT3, 5-HT4, 5-HT5, 5-HT6, and 5-HT7. Several of the subtypes are further subdivided such that the receptors are grouped pharmacologically as follows: 5-HT1A, 5-HT1B, 5-HT1D, 5-HT1E, 5-HT1F, 5-HT2A, 5-HT2B, 5-HT2C, 5-HT3A, 5-HT3B, 5-HT4, 5-HT5A, 5-HT6, 5-HT7. However, when the nucleic and amino acid sequences of the receptors are compared, the percent identity among the subtypes is not correlated to the pharmacological groupings.

Of the fourteen different mammalian serotonin receptors that have been cloned, all but one are members of the G-protein coupled receptor superfamily. Serotonin receptors 5-HT1A, 5-HT1B, and 5-HT1D inhibit adenylate cyclase, and 5-HT2 receptors activate phospholipase C pathways, stimulating breakdown of polyphosphoinositides. The 5-HT2 receptor belongs to the family of rhodopsin-like signal transducers that are distinguished by a seven-transmembrane configuration and functional linkage to G-proteins. The 5-HT3 receptor family includes ligand-gated ion channel receptors that have four putative TMDs.

Serotonin regulates a wide variety of sensory, motor and behavioral functions in the mammalian CNS, including behaviors such as learning and memory, sleep, thermoregulation, motor activity, pain, sexual and aggressive behaviors, appetite, neuroendocrine regulation, and biological rhythms. Serotonin has also been linked to pathophysiological conditions such as anxiety, depression, obsessive-compulsive disorders, schizophrenia, suicide, autism, migraine, emesis, alcoholism and neurodegenerative disorders. This biogenic amine neurotransmitter is synthesized by neurons of the brain stem that project throughout the CNS, with highest density in basal ganglia and limbic structures (Steinbusch, 1984, In: Handbook of Chemical Neuroanatomy 3:68-125, Bjorklund et al., Eds., Elsevier Science Publishers, B. V.).

Studies have suggested that serotonin may play a role in the immune system since data demonstrate that serotonin receptors are present on various cells of the immune system. There have been reports in the literature about the immunomodulatory effects of adding serotonin exogenously to mitogenically stimulated lymphocyte cultures. Under some circumstances, serotonin has been shown to stimulate the activated T cells (Foon et al., 1976, J. Immunol. 117:1545-1552; Kut et al., 1992, Immunopharmacol. Immunotoxicol. 14:783-796; Young et al., 1993, Immunology 80:395-400), whereas other laboratories report that high concentrations of added serotonin inhibit the proliferation (Slauson et al., 1984, Cell. Immunol. 84:240-252; Khan et al., 1986, Int. Arch. Allergy Appl. Immunol. 81:378-380; Mossner & Lesch, 1998, Brain, Behavior, and Immunity 12:249-271).

Of the fourteen known pharmacologically distinct serotonin receptors, lymphocytes express type 2A, type 2B, type 2C, type 6 and type 7 on resting cells (Ameisen et al., 1989, J. Immunol. 142:3171-3179; Stefulj et al., 2000, Brain, Behavior, and Immunity 14:219-224) and that the type 1A and type 3 receptors are up-regulated upon activation (Aune et al., 1993, J. Immunol. 151:1175-1183; Meyniel et al., 1997, Immunol. Lett. 55:151-160; Stefulj et al., 2000, Brain, Behavior, and Immunity 14:219-224).

The involvement of the 5-HT1A receptors in human and murine T cells has also been demonstrated (Aune et al., 1990, J. Immunol. 145:1826-1831; Aune et al., 1993, J. Immunol. 151:1175-1183; Aune et al., 1994, J. Immunol. 153:1826-1831). These studies established that IL-2-stimulated human T cell proliferation could be inhibited by a blockade of tryptophan hydroxylase, i.e., the first enzyme involved in the conversion of tryptophan to serotonin, and that the inhibition could be reversed by the addition of 5-hydroxy tryptophan. Furthermore, human T cell proliferation was blocked in vitro with a 5-HT1A-specific receptor antagonist. In a murine model, a type 1A receptor antagonist, but not a type 2 receptor antagonist, was able to inhibit the in vivo contact sensitivity response, but not antibody responses, to oxazalone.

PCT Publication No. WO 03/106660 discloses the use of fluphenazine, an antagonist of 5-HT(1B/1D) and 5-HT(2C) receptors, for inhibiting proliferation and inducing cell death in lymphocytes.

There exists a long-felt need to develop novel compounds and therapies for treating diseases related to activated lymphocytes and lymphocyte proliferation, especially diseases related to activated T cells and B cells. In addition, there is a long-felt need to develop novel compounds without the side effects related to other serotonin receptor antagonists. The present invention meets these needs.

BRIEF SUMMARY OF THE INVENTION

The present invention includes a compound of formula I:

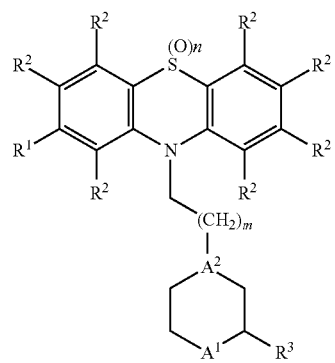

or a pharmaceutically acceptable salt, prodrug or solvate thereof, wherein:

$R^1$ is independently selected at each occurrence from hydrogen, halogen, $(C_1-C_6)$alkyl; $(C_1-C_6)$alkenyl; $(C_1-C_6)$alkoxy; OH; $NO_2$; C≡N; C(=O)OR$^7$; C(=O)NR$^7_2$; NR$^7_2$; NR$^7$C(=O)$(C_1-C_6)$alkyl; NR$^7$C(=O)O$(C_1-C_6)$alkyl; NR$^7$C(=O)NR$^7_2$; NR$^7$SO$_2$$(C_1-C_6)$alkyl; SO$_2$NR$^7_2$; OC(=O)$(C_1-C_6)$alkyl; O$(C_2-C_6)$alkylene-NR$^7_2$; $(C_2-C_6)$alkylene-OR$^7$; and $(C_1-C_3)$perfluoroalkyl;

$R^2$ is independently selected at each occurrence from hydrogen, halogen, $(C_1-C_6)$alkyl; $(C_1-C_6)$alkenyl; $(C_1-C_6)$alkoxy; OH; $NO_2$; C≡N; C(=O)OR$^7$; C(=O)NR$^7_2$; NR$^7_2$; NR$^7$C(=O)$(C_1-C_6)$alkyl; NR$^7$C(=O)O$(C_1-C_6)$alkyl; NR$^7$C(=O)NR$^7_2$; NR$^7$SO$_2$$(C_1-C_6)$alkyl; SO$_2$NR$^7_2$; OC(=O)$(C_1-C_6)$alkyl; O$(C_2-C_6)$alkylene-NR$^7_2$; $(C_2-C_6)$alkylene-OR$^7$; and $(C_1-C_3)$perfluoroalkyl;

$R^3$ is hydrogen, C(=O)OR$^7$, or C(=O)NR$^7_2$;

$A^1$ is $CH_2$ or NR$^4$;

$A^2$ is CH or N;

provided that if $A^1$ is $CH_2$, then $A^2$ is N, and if $A^2$ is CH, then $A^1$ is NR$^4$;

$R^4$ is H, $(C_1-C_6)$alkyl; $(CH_2)_pOR^7$; $(CH_2)_pNR^7_2$; $(CH_2)_pNHC(O)R^5$; $(CH_2)_pO(CH_2)_pOR^7$; $(CH_2)_pO(CH_2)_pNR^7_2$; $(CH_2)_pNR^4(CH_2)_pNR^7_2$; $(CH_2)_pO(CH_2)_pNHC(O)R^5$; $(CH_2)_pNR^7(CH_2)_pNHC(O)R^5$; $(CH_2)_qC(=O)OR^7$; $(CH_2)_qC(=O)NR^7_2$; $(CH_2)_pO(CH_2)_qC(=O)OR^7$; $(CH_2)_pO(CH_2)_qC(=O)NR^7_2$; $(CH_2)_pNR^7(CH_2)_qC(=O)OR^7$; or $(CH_2)_pNR^7(CH_2)_qC(=O)NR^7_2$;

$R^5$ is $(C_1-C_6)$alkyl; NR$^7$C(=O)$(C_1-C_6)$alkyl; NR$^7$C(=O)O$(C_1-C_6)$alkyl; NR$^7$C(=O)NR$^7_2$; CH(R$^6$)NR$^7_2$; CH(R$^6$)NR$^7$C(=O)$(C_1-C_6)$alkyl; or CH(R$^6$)NR$^7$C(=O)O$(C_1-C_6)$alkyl.

$R^6$ is H, $(C_1-C_6)$alkyl; $(C_2-C_6)$alkylene-OR$^7$; $(CH_2)_qC(=O)OR^7$; or $(CH_2)_qC(=O)NR^7_2$;

$R^7$ is independently selected at each occurrence from the group consisting of hydrogen and $(C_1-C_6)$alkyl;

m is independently at each occurrence 1, 2, or 3;

n is 0, 1, or 2;

p is independently at each occurrence 2 or 3; and q is independently at each occurrence 1 or 2.

In one aspect of the present invention, $R^1$ is hydrogen, halogen, $(C_1-C_6)$alkyl, methyl, C≡N, C(=O)NR$^7_2$, C(=O)NH$_2$, SO$_2$NR$^7_2$, SO$_2$NMe$_2$, $(C_1-C_3)$perfluoroalkyl, or CF$_3$.

In another aspect of the present invention, each occurrence of $R^2$ is hydrogen.

In yet another aspect of the present invention, $R^3$ is hydrogen.

In one aspect of the present invention, $A^1$ is NR$^4$.

In another aspect of the present invention, $A^2$ is N.

In still another aspect of the present invention, $R^4$ is H, $(CH_2)_pNR^7_2$, $CH_2CH_2NH_2$, $CH_2CH_2CH_2NH_2$, $(CH_2)_pNHC(O)R^5$, $CH_2CH_2NC(O)R^5$, $CH_2CH_2NHC(O)Me$, $CH_2CH_2NHC(O)CH_2NH_2$, or $CH_2CH_2NHC(O)CH_2NMe$.

In one aspect of the present invention, $R^5$ is $(C_1-C_6)$alkyl, CH(R$^6$)NR$^7_2$, or CH(R$^6$)NH$_2$ or NHMe.

In another aspect of the present invention, $R^6$ is H.

In yet another aspect of the present invention, m is 2, n is 0, p is 2, and q is 1.

The present invention includes a compound selected from the group consisting of ICI-681, ICI-682, ICI-683, ICI-684, ICI-685, ICI-686, ICI-687, ICI-696, ICI-697, ICI-712, ICI-713, and ICI-714, ICI-715, ICI-726, ICI-727, ICI-728, ICI-734, ICI-735, ICI-737, ICI-738, ICI-746, ICI-747, ICI-748, ICI-749, ICI-758, ICI-759, ICI-760, ICI-761, ICI-763, ICI-783, ICI-784, ICI-801, ICI-802, ICI-822, ICI-823, ICI-824, ICI-846, ICI-847, ICI-848, ICI-849, ICI-850, ICI-890, ICI-891, ICI-892, ICI-893, ICI-894, and ICI-895.

The present invention includes a method of inducing apoptosis in an immune cell, the method comprising contacting the immune cell with a compound of formula I. In an aspect, an immune cell is a lymphocyte.

In one aspect of the present invention, the lymphocyte is selected from the group consisting of a T cell and a B cell.

In another aspect of the present invention, the B cell is a plasma cell.

In still another aspect of the present invention, the plasma cell is a multiple myeloma cell.

The present invention includes a method of inhibiting proliferation of a lymphocyte, the method comprising contacting the lymphocyte with a compound of formula I.

In one aspect of the present invention, the lymphocyte is selected from the group consisting of a T cell and a B cell.

In still another aspect of the present invention, the B cell is a plasma cell.

In another aspect of the present invention, the plasma cell is a multiple myeloma cell.

The present invention includes a method of treating a disease characterized by abnormal lymphocyte proliferation, the method comprising administering to a mammal a compound of formula I.

The invention also includes a method of treating a disease selected from the group consisting of asthma and rheumatoid arthritis, the method comprising administering to a mammal a compound of formula I.

In one aspect of the present invention, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 7, comprising

FIG. 8, comprising FIGS. 8A through 8F, is a series of images depicting the chemical structures of the following 5-HT receptor antagonists: ICI-687 (FIG. 8A), ICI-696 (FIG. 8B), ICI-697 (FIG. 8C), ICI-712 (FIG. 8D), ICI-713 (FIG. 8E), and ICI-714 (FIG. 8F).

FIG. 9, comprising FIGS. 9A through 9F, is a series of images depicting the chemical structures of the following 5-HT receptor antagonists: ICI-715 (FIG. 9A), ICI-726 (FIG. 9B), ICI-727 (FIG. 9C), ICI-728 (FIG. 9D), ICI-734 (FIG. 9E), and ICI-735 (FIG. 9F).

FIG. 10, comprising FIGS. 10A through 10F, is a series of images depicting the chemical structures of the following 5-HT receptor antagonists: ICI-737 (FIG. 10A), ICI-738 (FIG. 10B), ICI-746 (FIG. 10C), ICI-747 (FIG. 10D), ICI-748 (FIG. 10E), and ICI-749 (FIG. 10F).

FIG. 11, comprising FIGS. 11A through 11F, is a series of images depicting the chemical structures of the following 5-HT receptor antagonists: ICI-758 (FIG. 11A), ICI-759 (FIG. 11B), ICI-760 (FIG. 11C), ICI-761 (FIG. 11D), ICI-763 (FIG. 11E), and ICI-783 (FIG. 11F).

FIG. 12, comprising

FIG. 13, comprising FIGS. 13A through 13F, is a series of images depicting the chemical structures of the following 5-HT receptor antagonists: ICI-846 (FIG. 13A), ICI-847 (FIG. 13B), ICI-848 (FIG. 13C), ICI-849 (FIG. 13D), ICI-850 (FIG. 13E), and ICI-890 (FIG. 13F).

FIG. 14, comprising

FIG. 30 is a schematic illustrating synthetic schemes for a number of compounds of the invention.

DETAILED DESCRIPTION OF THE INVENTION

Figure 1:
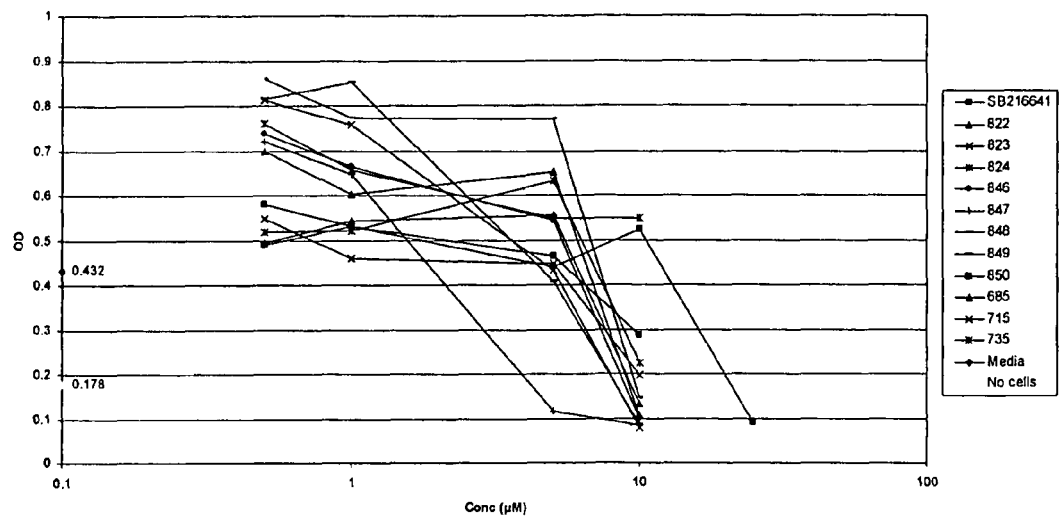
FIG. 1 is a graph depicting the results of an MTT assay demonstrating the inhibition of proliferation of HeLa cells using the indicated 5-HT receptor antagonists and the selective 5-HT1B receptor antagonist SB 216641.
Figure 2:
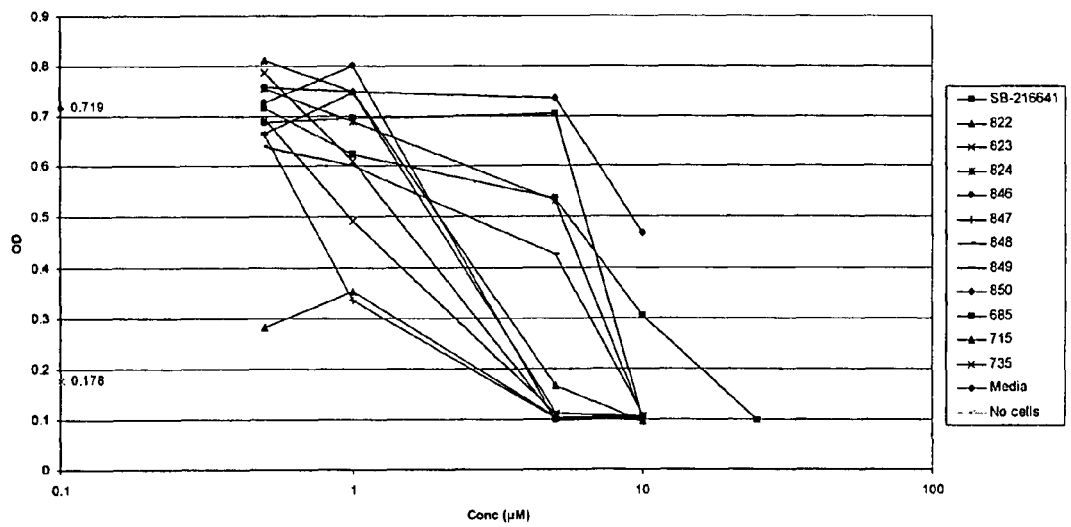
FIG. 2 is a graph depicting the results of an MTT assay demonstrating the inhibition of proliferation of CCRF-CEM cells using the indicated 5-HT receptor antagonists and the selective 5-HT1B receptor antagonist SB 216641.
Figure 3:
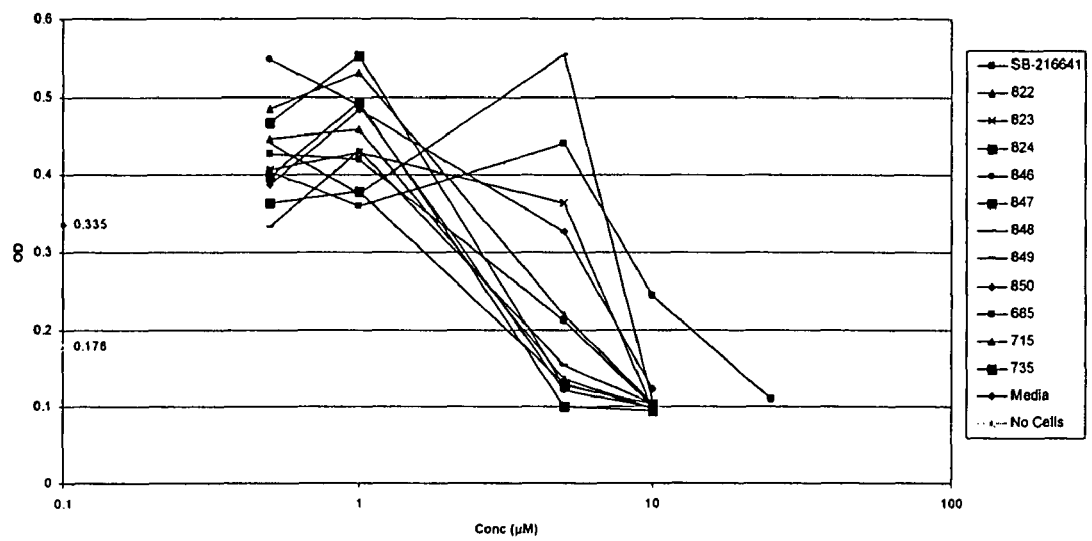
FIG. 3 is a graph depicting the results of an MTT assay demonstrating the inhibition of proliferation of RPMI-8226 cells using the indicated 5-HT receptor antagonists and the selective 5-HT1B receptor antagonist SB 216641.
Figure 4:
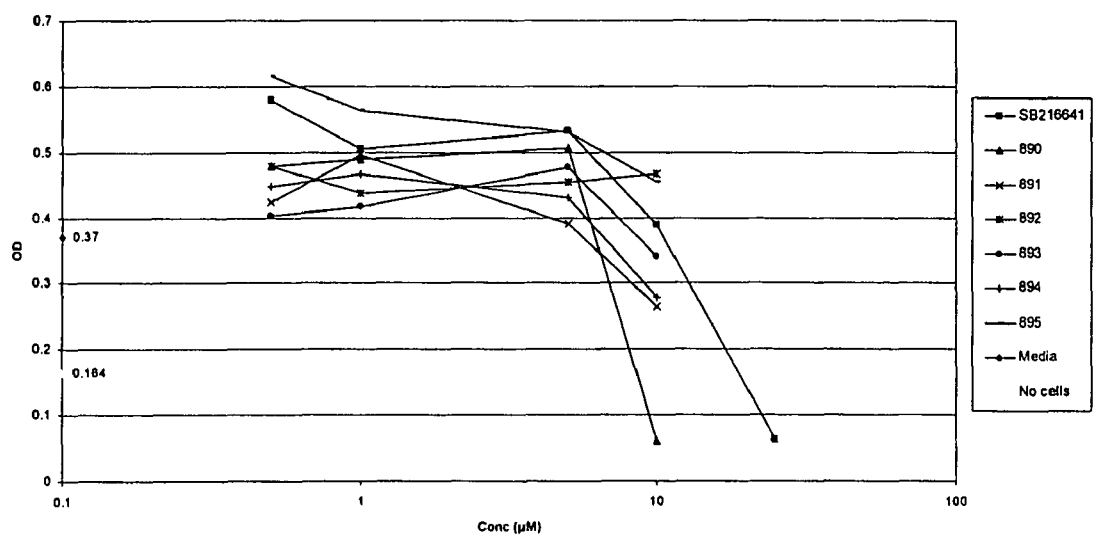
FIG. 4 is a graph depicting the results of an MTT assay demonstrating the inhibition of proliferation of HeLa cells using the indicated 5-HT receptor antagonists and the selective 5-HT 1B receptor antagonist SB 216641.
Figure 5:
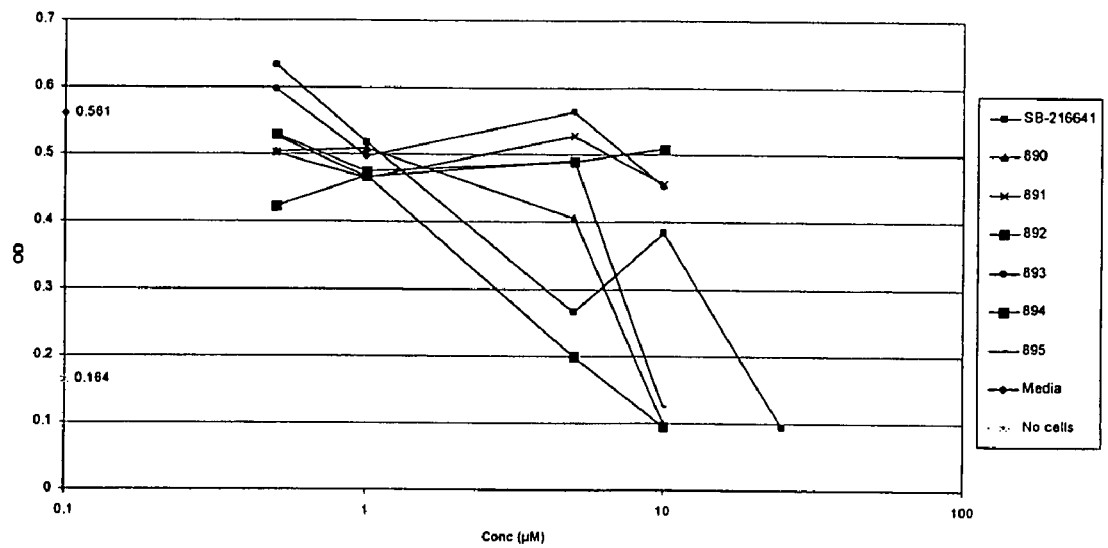
FIG. 5 is a graph depicting the results of an MTT assay demonstrating the inhibition of proliferation of CCRF-CEM cells using the indicated 5-HT receptor antagonists and the selective 5-HT1B receptor antagonist SB 216641.
Figure 6:
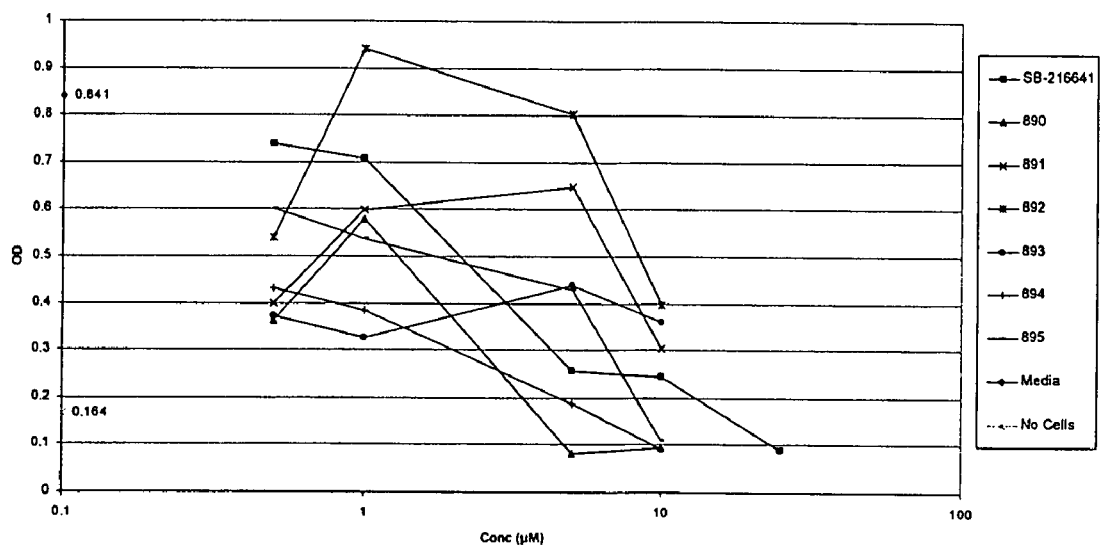
FIG. 6 is a graph depicting the results of an MTT assay demonstrating the inhibition of proliferation of RPMI-8226 cells using the indicated 5-HT receptor antagonists and the selective 5-HT1B receptor antagonist SB 216641.
Figure 7A:
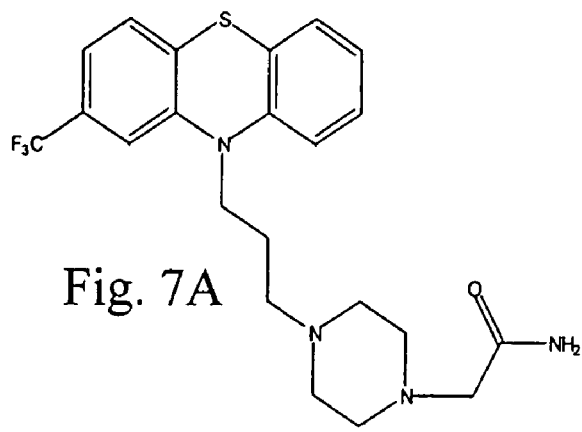
FIGS. 7A through 7F, is a series of images depicting the chemical structures of the following 5-HT receptor antagonists: ICI-681 (FIG. 7A), ICI-682 (FIG. 7B), ICI-683 (FIG. 7C), ICI-684 (FIG. 7D), ICI-685 (FIG. 7E), and ICI-686 (FIG. 7F).
Figure 7D:
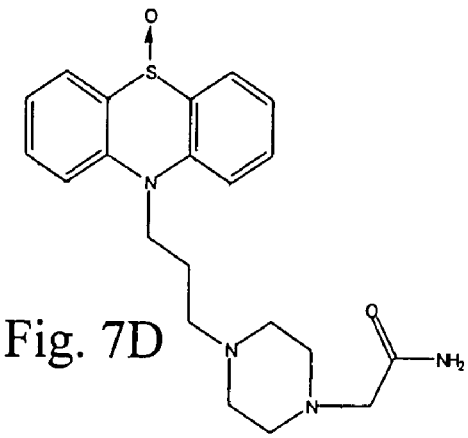
Figure 7B:
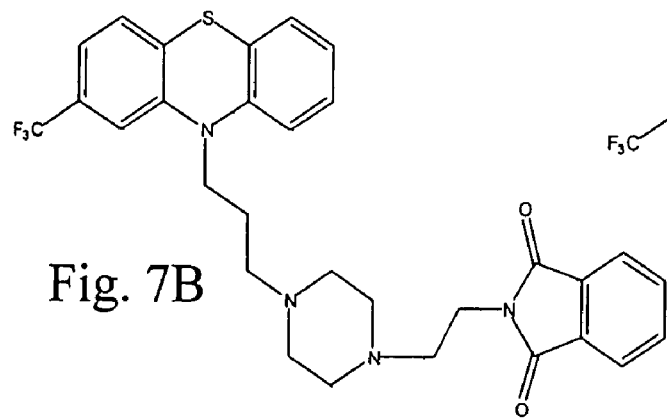
Figure 7E:
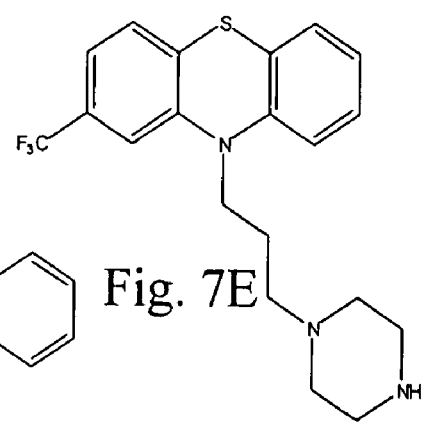
Figure 7C:
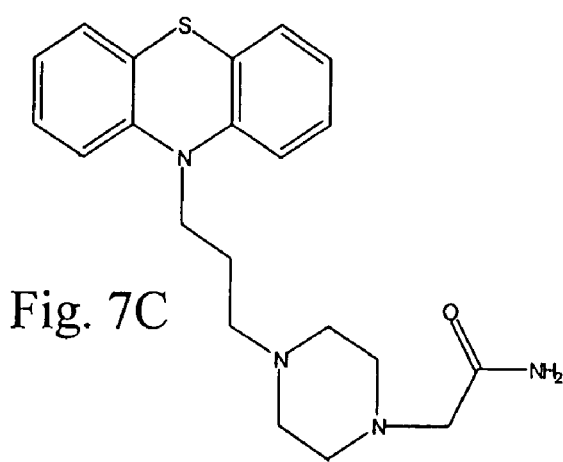
Figure 7F:
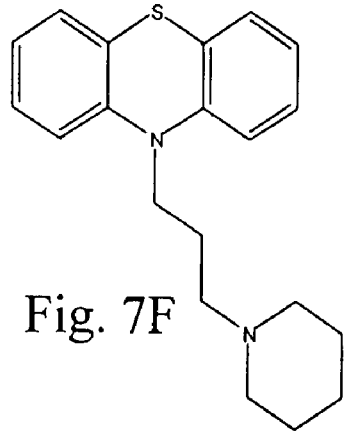
Figure 12A:
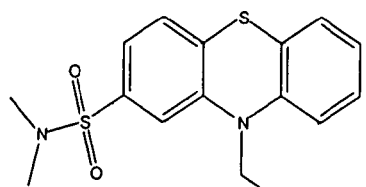
FIGS. 12A through 12F, is a series of images depicting the chemical structures of the following 5-HT receptor antagonists: ICI-784 (FIG. 12A), ICI-801 (FIG. 12B), ICI-802 (FIG. 12C), ICI-822 (FIG. 12D), ICI-823 (FIG. 12E), and ICI-824 (FIG. 12F).
Figure 12D:
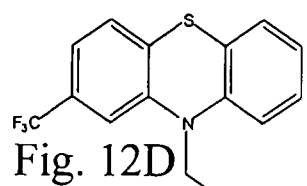
Figure 12B:
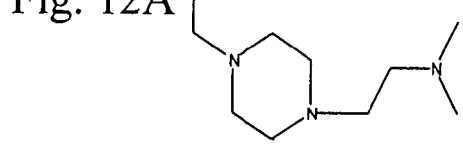
Figure 12E:
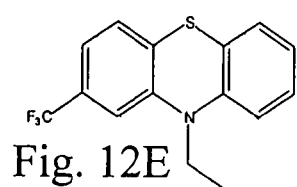
Figure 12C:
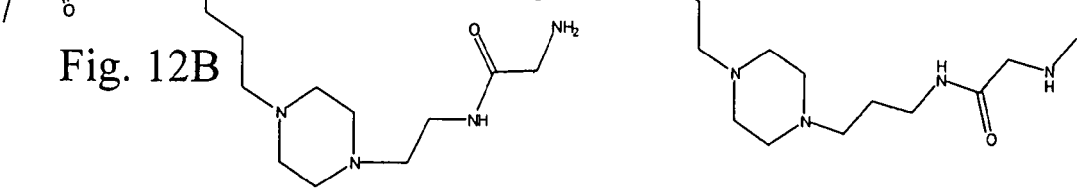
Figure 12F:
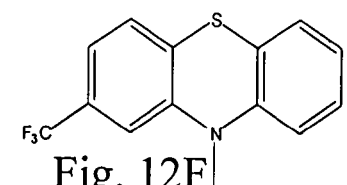
Figure 14A:
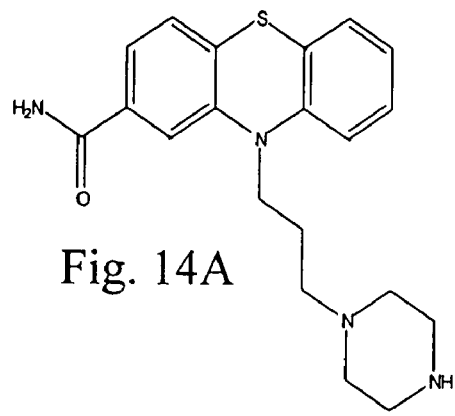
FIGS. 14A through 14E, is a series of images depicting the chemical structures of the following 5-HT receptor antagonists: ICI-891 (FIG. 14A), ICI-892 (FIG. 14B), ICI-893 (FIG. 14C), ICI-894 (FIG. 14D), and ICI-895 (FIG. 14E).
Figure 14D:
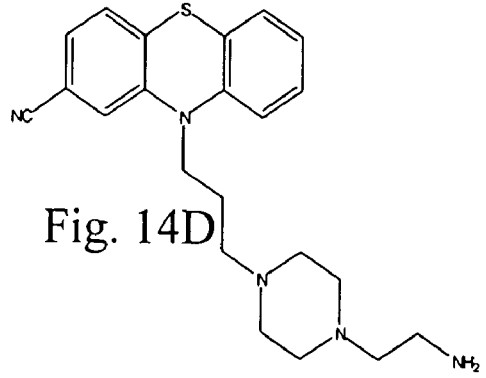
Figure 14B:
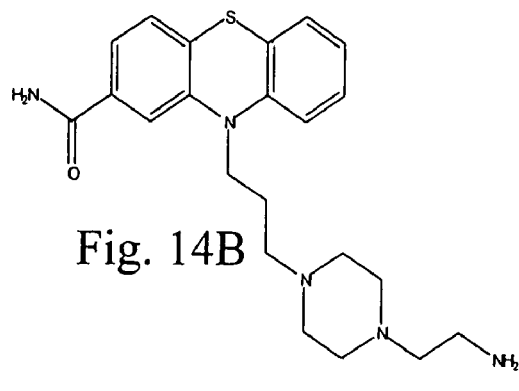
Figure 14E:
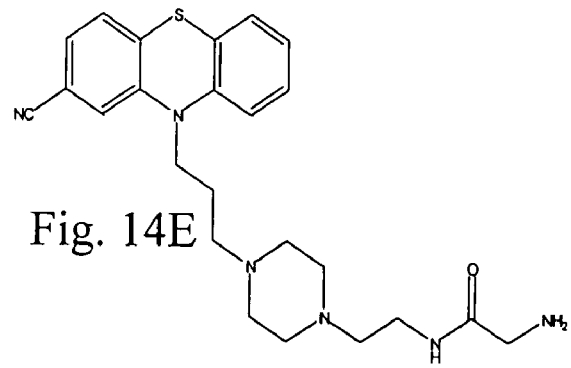
Figure 14C:
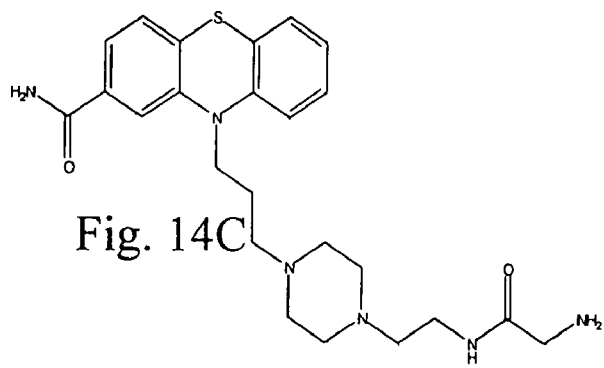
Figure 15:
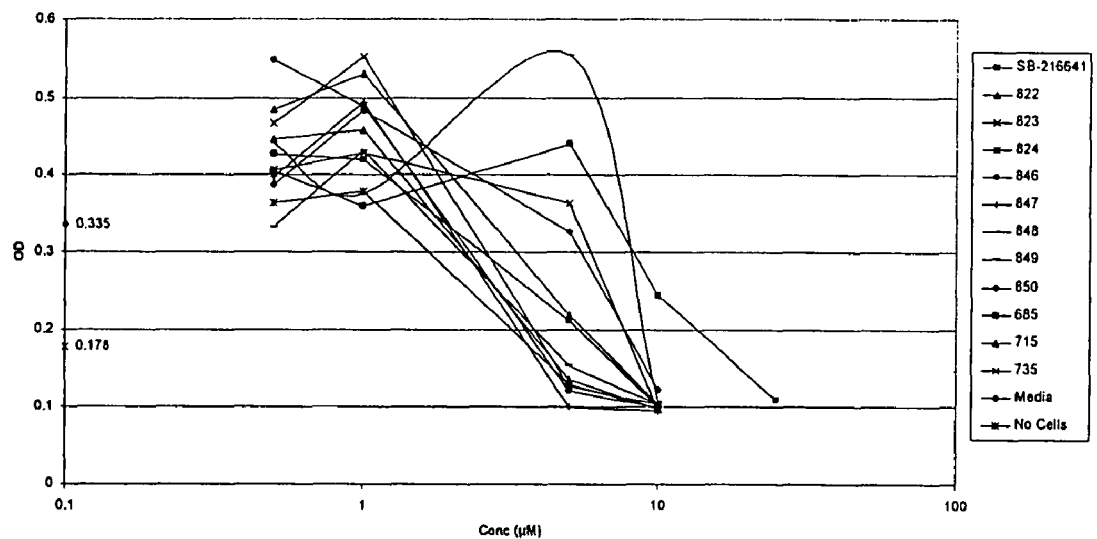
FIG. 15 is a graph depicting the results of an MTT assay demonstrating the inhibition of proliferation of RPMI-8226 cells using the indicated 5-HT receptor antagonists and the selective 5-HT1B receptor antagonist SB 216641.
Figure 16:
FIG. 16 is a graph depicting the results of an MTT assay demonstrating the inhibition of proliferation of CCRF-CEM cells using the indicated 5-HT receptor antagonists and the selective 5-HT1B receptor antagonist SB 216641.
Figure 17:
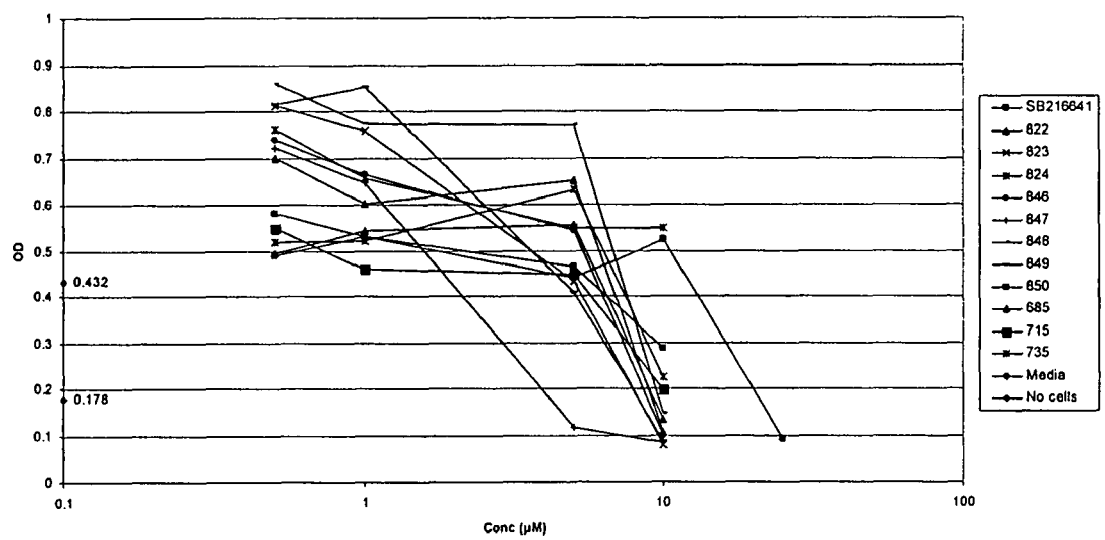
FIG. 17 is a graph depicting the results of an MTT assay demonstrating the inhibition of proliferation of HeLa cells using the indicated 5-HT receptor antagonists and the selective 5-HT1B receptor antagonist SB 216641.
Figure 18:
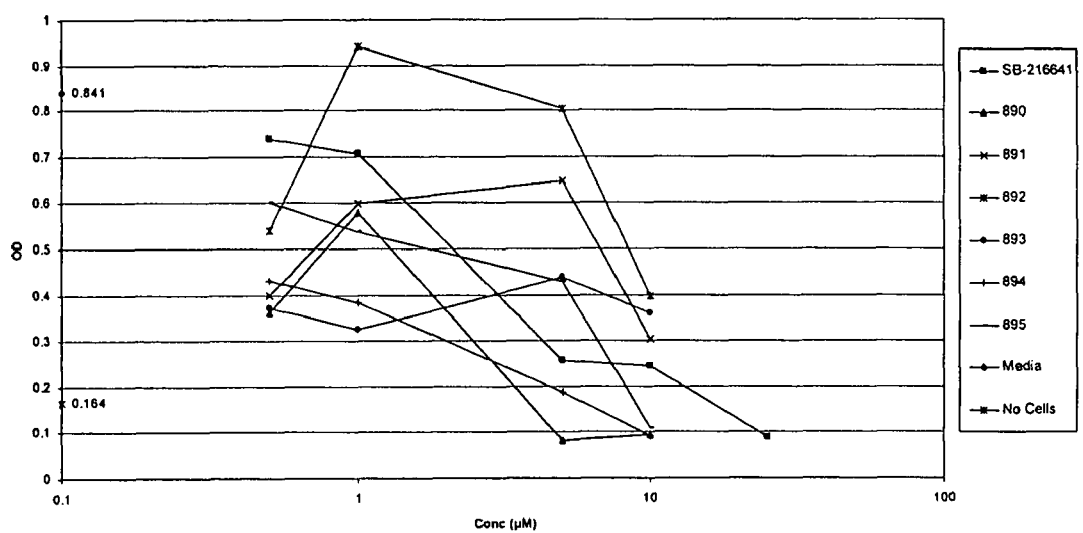
FIG. 18 is a graph depicting the results of an MTT assay demonstrating the inhibition of proliferation of RPMI-8226 cells using the indicated 5-HT receptor antagonists and the selective 5-HT1B receptor antagonist SB 216641.
Figure 19:
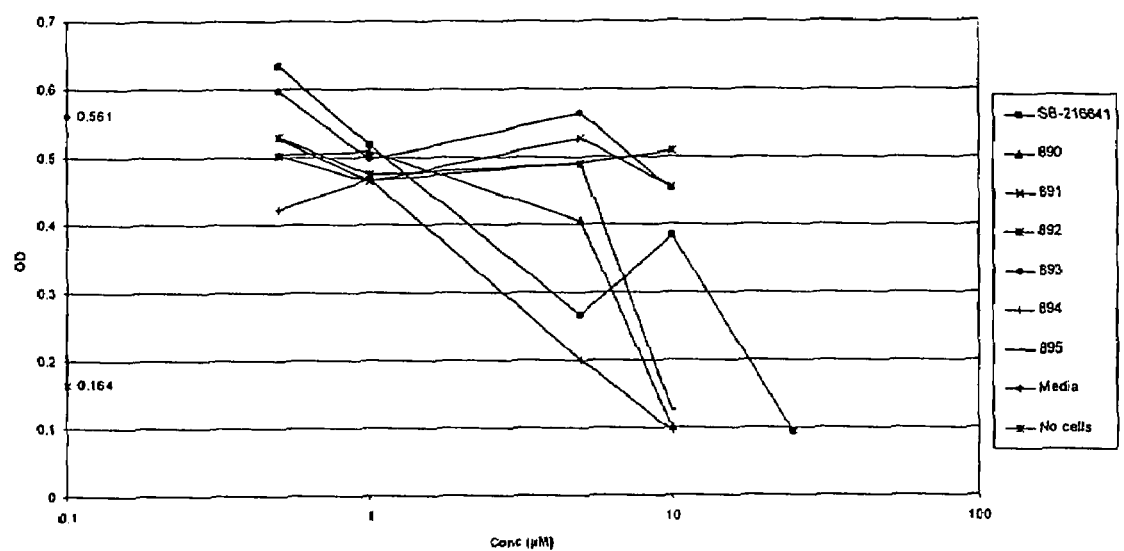
FIG. 19 is a graph depicting the results of an MTT assay demonstrating the inhibition of proliferation of CCRF-CEM cells using the indicated 5-HT receptor antagonists and the selective 5-HT1B receptor antagonist SB 216641.
Figure 20:
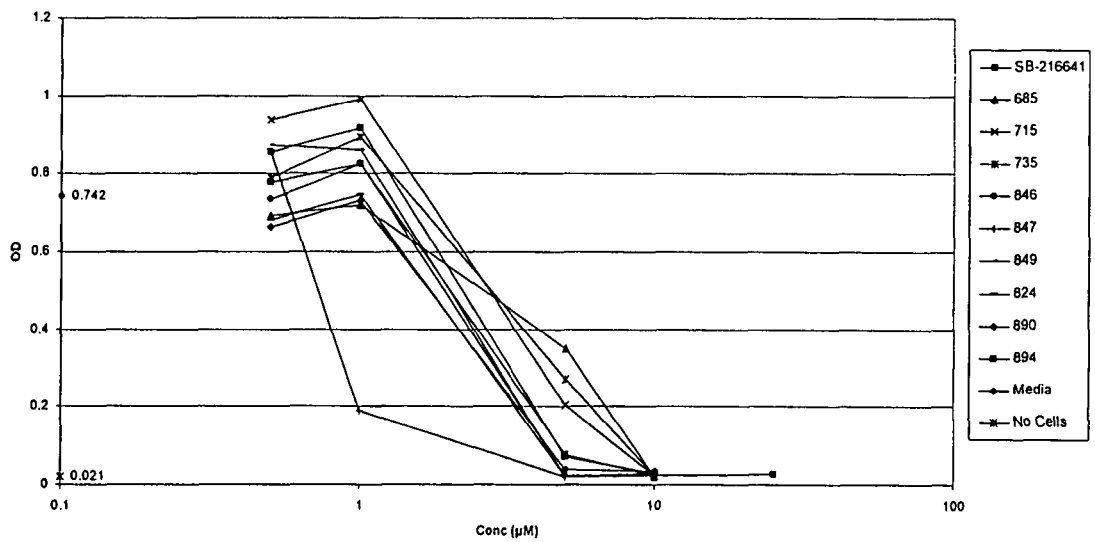
FIG. 20 is a graph depicting the results of an MTT assay demonstrating the inhibition of proliferation of RPMI-8226 cells using the indicated 5-HT receptor antagonists and the selective 5-HT1B receptor antagonist SB 216641.
Figure 21:
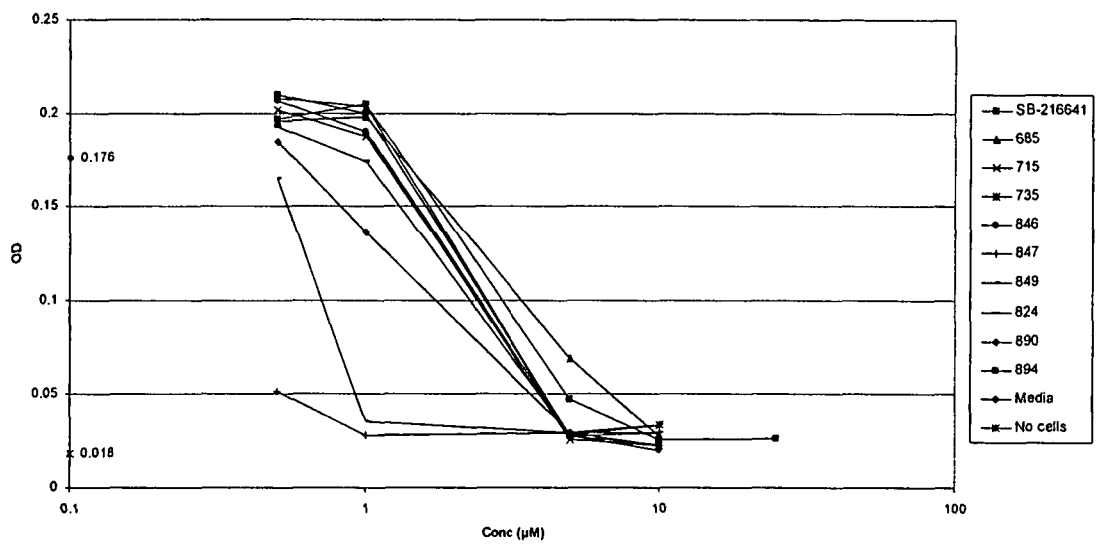
FIG. 21 is a graph depicting the results of an MTT assay demonstrating the inhibition of proliferation of CCRF-CEM cells using the indicated 5-HT receptor antagonists and the selective 5-HT1B receptor antagonist SB 216641.
Figure 22:
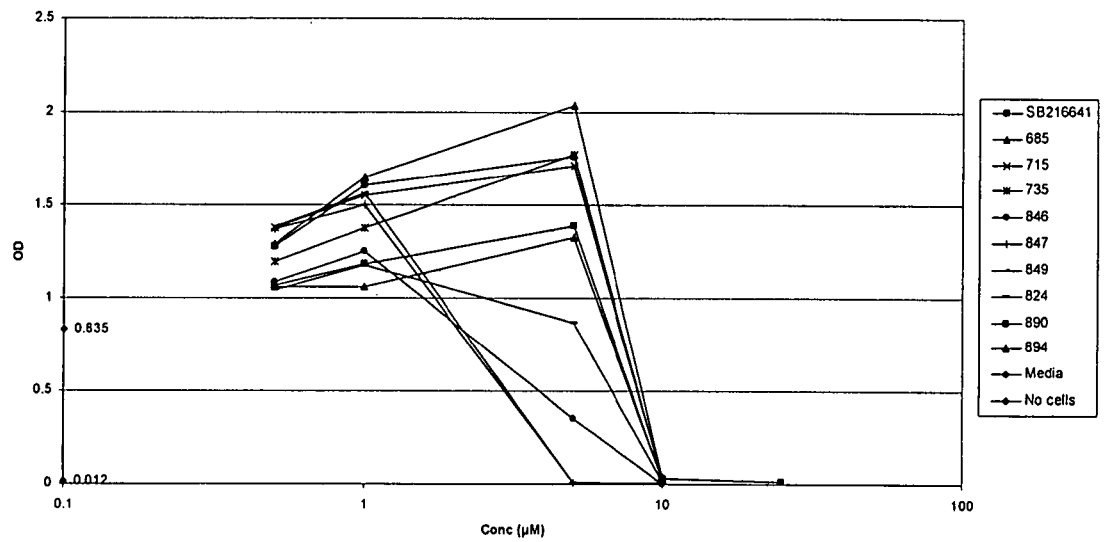
FIG. 22 is a graph depicting the results of an MTT assay demonstrating the inhibition of proliferation of HeLa cells using the indicated 5-HT receptor antagonists and the selective 5-HT1B receptor antagonist SB 216641.
Figure 23A:
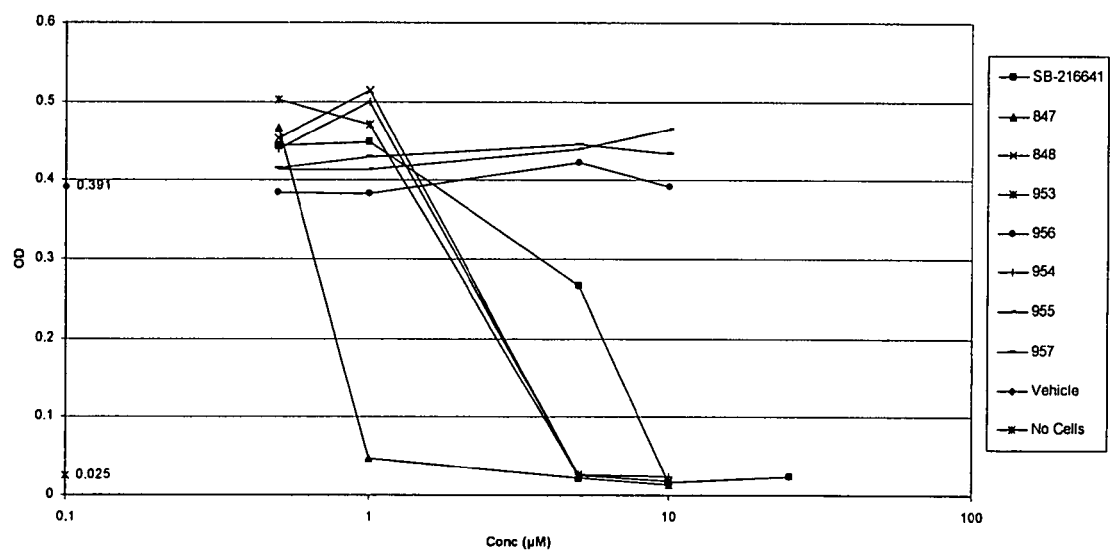
FIG. 23A is a graph depicting the results of an MTT assay demonstrating the inhibition of proliferation of RPMI-8226 cells using the indicated 5-HT receptor antagonists and the selective 5-HT1B receptor antagonist SB 216641.
Figure 23B:
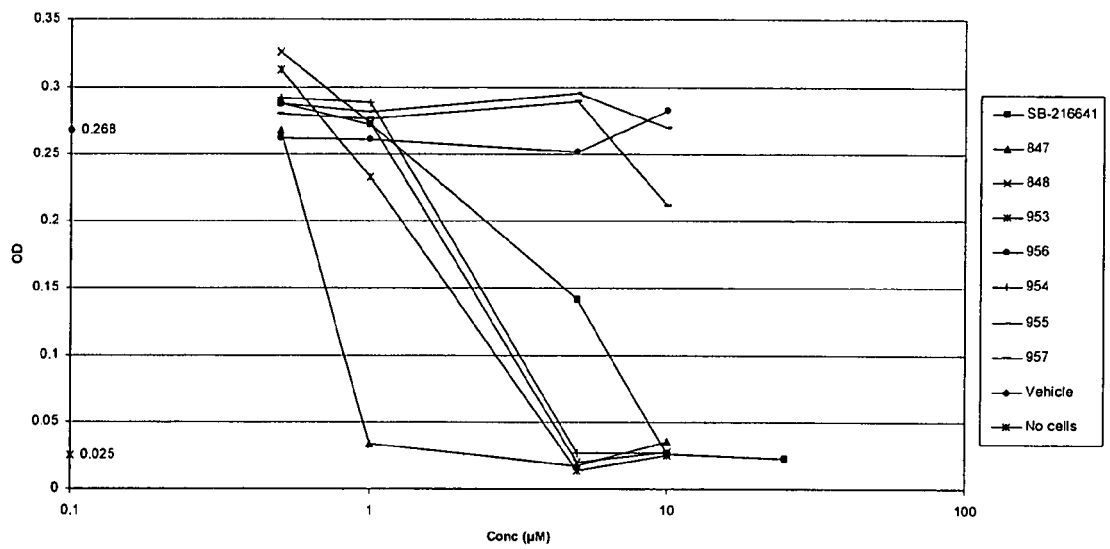
FIG. 23B, is a graph depicting the results of an MTT assay demonstrating the inhibition of proliferation of CCRF-CEM cells using the indicated 5-HT receptor antagonists and the selective 5-HT1B receptor antagonist SB 216641.
Figure 24:
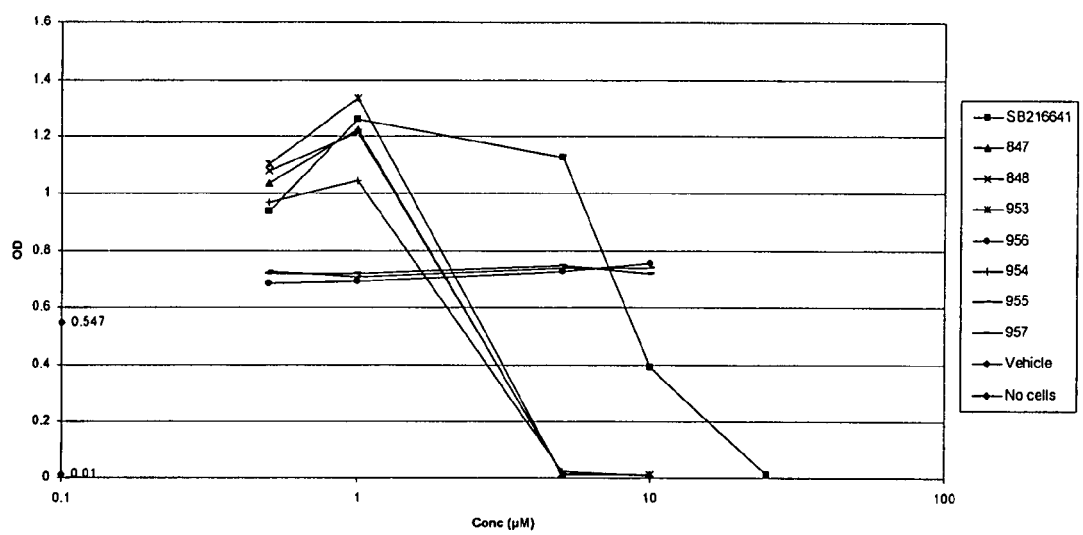
FIG. 24 is a graph depicting the results of an MTT assay demonstrating the inhibition of proliferation of HeLa cells using the indicated 5-HT receptor antagonists and the selective 5-HT1B receptor antagonist SB 216641.
Figure 25:
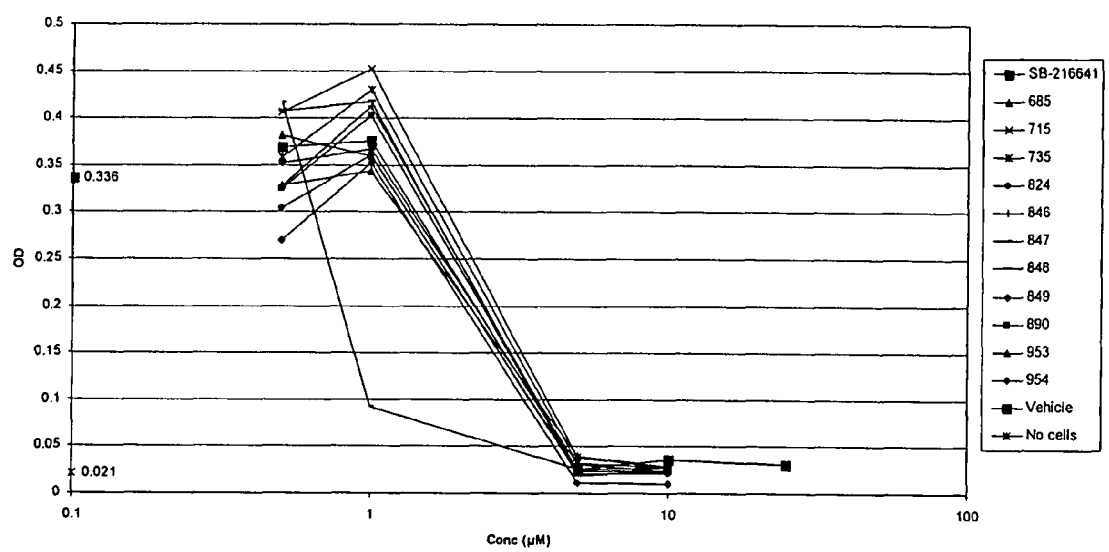
FIG. 25 is a graph depicting the results of an MTT assay demonstrating the inhibition of proliferation of RPMI-8226 cells using the indicated 5-HT receptor antagonists and the selective 5-HT1B receptor antagonist SB 216641.

The present invention relates to compositions and methods for inducing cell death and/or apoptosis in activated lymphocytes. In addition, the present invention relates to compositions and methods for inhibiting the proliferation of activated lymphocytes. As demonstrated by the data disclosed herein, the novel serotonin receptor antagonists disclosed herein inhibit proliferation and induce apoptosis in various lymphocyte cell lines, including neoplastic T cells and B cells. Thus, the present invention encompasses methods, compositions and kits for inhibiting the proliferation of lymphocytes and for inducing apoptosis in lymphocytes. The compositions and methods of the present invention are useful for treating various diseases associated with the proliferation and/or activation of lymphocytes, including, but not limited to lymphomas, myelomas, autoimmune diseases, transplant rejection, and the like.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

By T cell "activation," as the term is used herein, is meant that the T cell, when contacted with a compound, molecule, or cell capable of generating an immune response (e.g., a mitogen or antigen), detectably upregulates surface markers, such as CD25, i.e., the IL-2 receptor, initiates a phosphorylation cascade involving p56lck, causes the release of cytokines and interleukins, increases DNA synthesis which can be assessed by, among other methods, assessing the level of incorporation of $^3$H-thymidine into nascent DNA strands, and causes the cells to proliferate.

A "serotonin antagonist" is a composition of matter which, when administered to a mammal such as a human, detectably inhibits a biological activity attributable to the level or presence of serotonin.

A "serotonin receptor antagonist" is a composition of matter which, when administered to a mammal such as a human, detectably inhibits a biological activity attributable to the of serotonin to a serotonin receptor.

By the term "selective antagonist," as these terms are used herein, is meant a chemical agent that has at least about a 5-fold greater affinity for the target serotonin receptor type than for any other serotonin receptor family member.

As used herein, to "alleviate" a disease means reducing the severity of one or more symptoms of the disease.

By the term "allogeneic graft," as used herein, is meant grafting of any tissue within a species wherein there is a mismatch of an immunological marker, such as, but not limited to, the major histocompatibility complex (MHC), and/or a minor antigen.

The term "allogeneic graft response", as used herein, means any immune response directed against non-self tissue grafted into a recipient. Grafting procedures include, but are not limited to, administering non-self cells, tissue, or organs during, e.g., bone marrow transplantation, organ transplant, and the like.

The term "apoptosis," as used herein, means an active process, involving the activation of a preexisting cellular pathway, induced by an extracellular or intracellular signal, causing the death of the cell. In particular, the cell death involves nuclear fragmentation, chromatin condensation, and the like, in a cell with an intact membrane.

By the term "applicator," as the term is used herein, is meant any device including, but not limited to, a hypodermic syringe, a pipette, and the like, for administering the inhibitor of serotonin interaction with a serotonin receptor (e.g., a serotonin receptor antagonist) of the invention to a mammal.

A "cell cycle process," as used herein, means any cellular function or process associated with the cell cycle and the various phases thereof. Thus, a cell cycle process is one associated with, or which mediates or is involved in, the cell progressing through any portion of the cell cycle.

Inhibition of serotonin signaling is "deleterious" to a cell, as the term is used herein, where the inhibition mediates a detectable decrease in the viability of the cell. Cell viability can be assessed using standard methods that are well-known in the art, including, but not limited to, assessing the level of biomolecular synthesis (e.g., protein synthesis, nucleic acid synthesis, and the like), trypan blue exclusion, MTT reduction, uptake of propidium iodide, exposure of phosphatidylserine on the cell surface, DNA fragmentation and/or ladder formation, and the like.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By the term "does not substantially cross the blood-brain barrier", as used herein, means that the inhibitor does not detectably cross the blood-brain barrier as assessed using standard assays such as those disclosed herein, known in the art, or such assays as are developed in the future to determine the permeability of a compound across the blood-brain barrier. Such assays include, but are not limited to, assessing the neuro-psychotropic effects of the compound when administered to an animal. Further, the assays encompass, among other things, assessing the concentration of the compound beyond the barrier, or an art-recognized model of the blood-brain barrier, over time to determine the permeability of the compound through the barrier.

It would be understood by the artisan that an inhibitor can be ab initio impermeable and not cross the blood-brain barrier at a detectable level. Further, it would be understood that an inhibitor of interest can be modified, using techniques well-known in the art, such that it does not detectably cross the blood-brain barrier, or crosses it at a detectably lower level that it did before it was modified. In both instances, whether it loses its ability to cross the blood-brain barrier at a detectable level or loses the ability to cross it at a lower level than before it was modified, the compound is considered to "not substantially cross the blood-brain barrier" for purposes of this section.

By the term "effective amount", as used herein, is meant an amount of an inhibitor that is sufficient to mediate a detectable decrease in transmission of serotonin signaling via a serotonin receptor on a cell. Transmission of a serotonin signal can be assessed using standard methods well-known in the art, such as, but not limited to, those described elsewhere herein, including, for example, assessing the level of binding of serotonin with a receptor and/or assessing the level of activation of a cell.

The skilled artisan would understand that the amount varies and can be readily determined based on a number of factors such as the disease or condition being treated, the age and health and physical condition of the mammal being treated, the severity of the disease, the particular compound being administered, and the like. Generally, the dosage will be set between 1 mg/kg and 25 mg/kg. In one embodiment, the drug is administered through intravenous bolus injection. This type of bolus administration can be used to ensure that all of the immunologically relevant cells encounter sufficient quantity of the drug in order to block their receptor-mediated signals. However, the invention is not limited to this method of administration.

By the term "immune reaction," as used herein, is meant the detectable result of stimulating and/or activating an immune cell.

"Immune response," as the term is used herein, means a process that results in the activation and/or invocation of an effector function in either the T cells, B cells, natural killer (NK) cells, and/or antigen-presenting cells (APCs). Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, and the like.

"Immune cell," as the term is used herein, means any cell involved in the mounting of an immune response. Such cells include, but are not limited to, T cells, B cells, NK cells, antigen-presenting cells, and the like.

"Instructional material," as that term is used herein, includes a publication, a recording, a diagram, or any other medium of expression which can be used to communicate the usefulness of the nucleic acid, peptide, and/or compound of the invention in the kit for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the nucleic acid, peptide, and/or compound of the invention or be shipped together with a container which contains the nucleic acid, peptide, and/or compound. Alternatively, the instructional material may be shipped separately from the container with the intention that the recipient uses the instructional material and the compound cooperatively.

By the term "serotonin family receptor" is meant any receptor which can be classified as a serotonin, adrenergic, histamine, melatonin, or dopaminergic receptor. That is, the receptor specifically binds with any of these molecules and does not significantly bind with other molecules in a sample.

A "serotonin receptor" includes a polypeptide that specifically binds with serotonin.

"Serotonin signal," as the term is used herein, means a change in the balance of any intracellular biochemical pathway as a result of a receptor-mediated interaction with serotonin, a specific drug interaction with any serotonin-specific receptor, or both, that results in the change.

Similarly, "activation of a serotonin" receptor, as used herein, means that binding of serotonin with a serotonin receptor on a cell induces the typical cascade of intra and extracellular events associated with such binding.

A "receptor" is a compound that specifically binds with a ligand.

By the term "specifically binds," as used herein, is meant a receptor which recognizes and binds serotonin family molecules present in a sample (i.e., dopaminergic proteins, adrenergic protein, histamines, melatonin, and serotonin), but does not substantially recognize or bind other molecules in the sample.

To "treat" a disease as the term is used herein, means to reduce the frequency of the disease or disorder reducing the frequency with which a symptom of the one or more symptoms disease or disorder is experienced by an animal.

Description

The present invention relates to methods, compositions and kits for treating diseases and conditions associated with the proliferation of activated lymphocytes and the diseases resulting from the activation of lymphocytes. The present invention encompasses methods for inhibiting and killing activated lymphocytes, compositions that inhibit and/or kill activated lymphocytes, compositions that inhibit the proliferation of activated lymphocytes, and kits for using the methods and compositions of the invention.

The compositions of the present invention include 5-HT receptor antagonists having the chemical formulae disclosed elsewhere herein. The compositions disclosed herein further comprise combinations of these 5-HT receptor antagonists with additional compositions for inhibiting and/or killing activated lymphocytes. As demonstrated by the data disclosed herein, the compositions of the present invention inhibit and/or kill activated lymphocytes by, among other things, inducing apoptosis and cell death in activated lymphocytes. In addition, the compounds of the present invention inhibit proliferation of lymphocytes, such as T cells and B cells, and are therefore useful in the treatment of diseases where activated and/or proliferating lymphocytes cause pathology. Such diseases include, but are not limited to, lymphomas, myelomas, autoimmune diseases, and transplant rejection.

The methods of the present invention encompass methods of inhibiting and/or killing an activated lymphocyte, and methods of inhibiting the proliferation of a lymphocyte. This is because, as demonstrated by the data disclosed herein, the methods of the invention cause a dose and time dependent inhibition of proliferating lymphocytes, as well as dose and time dependent apoptosis in lymphocytes. The methods of the present invention further comprise methods of treating a patient suffering from a disease associated with an activated lymphocyte. Such diseases are known in the art and are disclosed elsewhere herein. The methods of the invention are based, in part, on the novel finding that 5-HT receptor antagonists, such as those disclosed herein, are useful in inhibiting and/or killing activated lymphocytes.

I. Compositions

The present invention comprises compositions for inhibiting and/or killing activated lymphocytes, for inhibiting proliferation in lymphocytes, and for treating diseases associated with such lymphocytes. One embodiment of the present invention, includes compositions which, as demonstrated by the data disclosed herein, induce cell death and apoptosis in various activated lymphocytes, including T cells and B cells. The compositions of the present invention include a composition of Formula I, as well as the compositions disclosed below.

The present invention comprises a compound according to formula I, as disclosed herein. As demonstrated by the data disclosed herein, 5-HT receptor antagonists having the structure of formula I are useful in the present invention for inhibiting the proliferation of lymphocytes, such as T cells and B cells, and for inducing apoptosis and/or cell death in lymphocytes. Thus, the compounds of the present invention is useful for treating, among other things, lymphomas, myelomas, autoimmune diseases, transplant rejection, and the like.

The present invention comprises administering an effective amount of a compound according to formula I, or a pharmaceutically acceptable salt of such a compound:

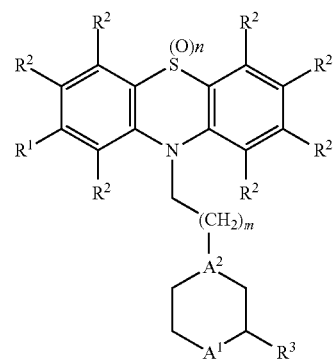

wherein:

$R^1$ is independently selected at each occurrence from hydrogen, halogen, $(C_1-C_6)$alkyl; $(C_1-C_6)$alkenyl; $(C_1-C_6)$alkoxy; OH; $NO_2$; C≡N; C(=O)OR$^7$; C(=O)NR$^7{}_2$; NR$^7{}_2$; NR$^7$C(=O)$(C_1-C_6)$alkyl; NR$^7$C(=O)O$(C_1-C_6)$alkyl; NR$^7$C(=O)NR$^7{}_2$; NR$^7$SO$_2$$(C_1-C_6)$alkyl; SO$_2$NR$^7{}_2$; OC(=O)$(C_1-C_6)$alkyl; O$(C_2-C_6)$alkylene-NR$^7{}_2$; $(C_2-C_6)$alkylene-OR$^7$; and $(C_1-C_3)$perfluoroalkyl;

$R_2$ is independently selected at each occurrence from hydrogen, halogen, $(C_1-C_6)$alkyl; $(C_1-C_6)$alkenyl; $(C_1-C_6)$alkoxy; OH; $NO_2$; C≡N; C(=O)OR$^7$; C(=O)NR$^7{}_2$; NR$^7{}_2$; NR$^7$C(=O)$(C_1-C_6)$alkyl; NR$^7$C(=O)O$(C_1-C_6)$alkyl; NR$^7$C(=O)NR$^7{}_2$; NR$^7$SO$_2$$(C_1-C_6)$alkyl; SO$_2$NR$^7{}_2$; OC(=O)$(C_1-C_6)$alkyl; O$(C_2-C_6)$alkylene-NR$^7{}_2$; $(C_2-C_6)$alkylene-OR$^7$; and $(C_1-C_3)$perfluoroalkyl;

$R^3$ is hydrogen, C(=O)OR$^7$, or C(=O)NR$^7{}_2$;

$A^1$ is $CH_2$ or NR$^4$;

$A_2$ is CH or N; provided that if $A^1$ is $CH_2$, then $A^2$ is N, and if $A^2$ is CH, then $A^1$ is NR$^4$;

$R^4$ is H, substituted or unsubstituted aryl, substituted or unsubstituted heteroaryl; $(C_1-C_6)$alkyl; $(CH_2)_pOR^7$; $(CH_2)_pNR^7{}_2$; $(CH_2)_pNHC(O)R^5$; $(CH_2)_pO(CH_2)_pOR^7$; $(CH_2)_pO(CH_2)_pNR^7{}_2$; $(CH_2)_pNR^4(CH_2)_pNR^7{}_2$; $(CH_2)_pO(CH_2)_pNHC(O)R^5$; $(CH_2)_pNR^7(CH_2)_pNHC(O)R^5$; $(CH_2)_qC(=O)OR^7$; $(CH_2)_qC(=O)NR^7{}_2$; $(CH_2)_pO(CH_2)_qC(=O)OR^7$; $(CH_2)_pO(CH_2)_qC(=O)NR^7{}_2$; $(CH_2)_pNR^7(CH_2)_qC(=O)OR^7$; $(CH_2)_pNR^7(CH_2)_qC(=O)NR^7{}_2$; or

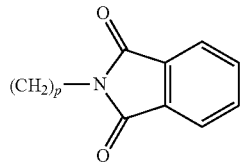

$R^5$ is $(C_1-C_6)$alkyl; NR$^7$C(=O)$(C_1-C_6)$alkyl; NR$^7$C(=O)O$(C_1-C_6)$alkyl; NR$^7$C(=O)NR$^7{}_2$; CH(R$^6$)NR$^7{}_2$; CH(R$^6$)NR$^7$C(=O)$(C_1-C_6)$alkyl; or CH(R$^6$)NR$^7$C(=O)O$(C_1-C_6)$alkyl.

$R^6$ is H, $(C_1-C_6)$alkyl; $(C_2-C_6)$alkylene-OR$^7$; $(CH_2)_qC(=O)OR^7$; or $(CH_2)_qC(=O)NR^{12}$;

$R^7$ is independently selected at each occurrence from the group consisting of hydrogen and $(C_1-C_6)$alkyl;

m is independently at each occurrence 1, 2, or 3;

n is 0, 1, or 2;

p is independently at each occurrence 2 or 3; and q is independently at each occurrence 1 or 2;

wherein the substituents for the substituted aryl and substituted heterocyclic groups comprising or included within $R^4$ are independently selected from the group consisting of halogen, $(C_1-C_6)$alkyl; $(C_1-C_6)$alkenyl; $(C_1-C_6)$alkoxy; OH; $NO_2$; C≡N; C(=O)OR$^7$; C(=O)NR$^7{}_2$; NR$^7{}_2$; NR$^7$C(=O)$(C_1-C_6)$alkyl; NR$^7$C(=O)O$(C_1-C_6)$alkyl; NR$^7$C(=O)NR$^7{}_2$; NR$^7$SO$_2$$(C_1-C_6)$alkyl; SO$_2$NR$^7{}_2$; OC(=O)$(C_1-C_6)$alkyl; O$(C_2-C_6)$alkylene-NR$^7{}_2$; $(C_2-C_6)$alkylene-OR$^7$; and $(C_1-C_3)$perfluoroalkyl.

In preferred embodiments, $R^1$ is hydrogen, halogen, $(C_1-C_6)$alkyl, preferably methyl, C≡N, C(=O)NR$^7{}_2$, preferably C(=O)NH$_2$, SO$_2$NR$^7{}_2$, preferably SO$_2$NMe$_2$, or $(C_1-C_3)$perfluoroalkyl, preferably CF$_3$. In more preferred embodiments, $R^1$ is hydrogen, C≡N, or CF$_3$.

In preferred embodiments one or fewer occurrences of $R^2$ are other than hydrogen, and in the most preferred embodiments, each occurrence of $R^2$ is hydrogen.

In preferred embodiments, $R^3$ is hydrogen.

In preferred embodiments, $A^1$ is NR$^4$.

In preferred embodiments, $A^2$ is N.

In more preferred embodiments, $A^1$ is NR$^4$ and $A^2$ is N.

In preferred embodiments, $R^4$ is H, $(CH_2)_pNR^7{}_2$, preferably $CH_2CH_2NH_2$ or $CH_2CH_2CH_2NH_2$, $(CH_2)_pNHC(O)R^5$, preferably $CH_2CH_2NC(O)R^5$, more preferably $CH_2CH_2NHC(O)Me$, $CH_2CH_2NHC(O)CH_2NH_2$, or $CH_2CH_2NHC(O)CH_2NMe$. In preferred embodiments, $R^5$ is $(C_1-C_6)$alkyl; or CH(R$^6$)NR$^7{}_2$, preferably CH(R$^6$)NH$_2$ or NHMe.

In preferred embodiments, $R^6$ is H.

In preferred embodiments, m is 2.

In preferred embodiments, n is 0.

In preferred embodiments, p is 2.

In preferred embodiments, q is 1.

In the definitions of each of the compounds of formula I above:

The term "alkyl", by itself or as part of another substituent means, unless otherwise stated, a straight, branched or cyclic chain hydrocarbon having the number of carbon atoms designated (i.e. $C_1-C_6$ means one to six carbons) and includes straight, branched chain or cyclic groups. Examples include: methyl, ethyl, propyl, isopropyl, butyl, isobutyl, tertbutyl, pentyl, neopentyl, hexyl, cyclohexyl and cyclopropylmethyl. Most preferred is $(C_1-C_3)$alkyl, particularly ethyl, methyl and isopropyl.

The term "alkenyl" employed alone or in combination with other terms, means, unless otherwise stated, a stable monounsaturated or di-unsaturated straight chain, branched chain or cyclic hydrocarbon group having the stated number of carbon atoms. Examples include vinyl, propenyl (allyl), crotyl, isopentenyl, butadienyl, 1,3-pentadienyl, 1,4-pentadienyl, cyclopentenyl, cyclopentadienyl and the higher homologs and isomers. A functional group representing an alkene is exemplified by CH=CHCH$_2$.

The term "alkylene", by itself or as part of another substituent means, unless otherwise stated, a divalent straight, branched or cyclic chain hydrocarbon.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are $(C_1-C_3)$alkoxy, particularly ethoxy and methoxy.

The term "aryl", employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

The term "heteroaryl" refers to a heterocycle having aromatic character. A polycyclic heteroaryl may include one or more rings which are partially saturated. Examples include tetrahydroquinoline and 2,3 dihydrobenzofuryl. For compounds of formula I, the attachment point is understood to be on an atom which is part of an aromatic monocyclic ring or a ring component of a polycyclic aromatic which is itself an aromatic ring.

Examples of heteroaryl groups include: pyridyl, pyrazinyl, pyrimidinyl, particularly 2 and 4 pyrimidinyl, pyridazinyl, thienyl, furyl, pyrrolyl, particularly 2 pyrrolyl, imidazolyl, thiazolyl, oxazolyl, pyrazolyl, particularly 3 and 5 pyrazolyl, isothiazolyl, 1,2,3 triazolyl, 1,2,4 triazolyl, 1,3,4 triazolyl, tetrazolyl, 1,2,3 thiadiazolyl, 1,2,3 oxadiazolyl, 1,3,4 thiadiazolyl and 1,3,4 oxadiazolyl.

Examples of polycyclic heterocycles include: indolyl, particularly 3,4,5,6 and 7 indolyl, indolinyl, quinolyl, tetrahydroquinolyl, isoquinolyl, particularly 1 and 5 isoquinolyl, 1,2,3,4 tetrahydroisoquinolyl, cinnolinyl, quinoxalinyl, particularly 2 and 5 quinoxalinyl, quinazolinyl, phthalazinyl, 1,8 naphthyridinyl, 1,4 benzodioxanyl, coumarin, dihydrocoumarin, benzofuryl, particularly 3,4,1,5 naphthyridinyl, 5,6 and 7 benzofuryl, 2,3 dihydrobenzofuryl, 1,2 benzisoxazolyl, benzothienyl, particularly 3,4,5,6, and 7 benzothienyl, benzoxazolyl, benzthiazolyl, particularly 2 benzothiazolyl and 5 benzothiazolyl, purinyl, benzimidazolyl, particularly 2 benzimidazolyl, benztriazolyl, thioxanthinyl, carbazolyl, carbolinyl, acridinyl, pyrrolizidinyl, and quinolizidinyl.

The aforementioned listing of heteroaryl moieties is intended to be representative and not limiting.

The term halogen means, unless otherwise stated, a fluorine, chlorine, bromine, or iodine atom, preferably, fluorine, chlorine, or bromine, more preferably, fluorine or chlorine.

The term "$(C_x-C_y)$perfluoroalkyl," wherein x<y, means an alkyl group with a minimum of x carbon atoms and a maximum of y carbon atoms, wherein all hydrogen atoms are replaced by fluorine atoms. Preferred is —$CF_3$.

The compounds of formula I can be prepared by a person skilled in the art of synthetic organic chemistry. The person skilled in the art knows how to select and implement appropriate synthetic routes. Suitable synthetic methods may be identified by reference to the literature describing synthesis of analogous compounds, and then performing the synthesis of the desired compound following the route used for the analogous compounds, modifying the starting materials, reagents, and reaction conditions as appropriate to synthesizing any particular desired compounds. In addition, reference may be made to sources such as Comprehensive Organic Synthesis, Ed. B. M. Trost and I. Fleming (Pergamon Press 1991), Comprehensive Organic Functional Group Transformations, Ed. A. R. Katritzky, O. Meth Cohn, and C. W. Rees (Pergamon Press, 1996), Comprehensive Organic Functional Group Transformations II, Ed. A. R. Katritzky and R. J. K. Taylor (Editor) (Elsevier, 2nd Edition, 2004), Comprehensive Heterocyclic Chemistry, Ed. A. R. Katritzky and C. W. Rees (Pergamon Press, 1984), and Comprehensive Heterocyclic Chemistry II, Ed. A. R. Katritzky, C. W. Rees, and E. F. V. Scriven (Pergamon Press, 1996), the entire disclosures of which are incorporated herein by reference.

It will be understood that when compounds of formula I contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention which are efficacious in the treatment of diseases associated with activated and/or proliferating lymphocytes, including, but not limited to, lymphomas, myelomas, autoimmune diseases, and transplant rejection.

The isomers resulting from the presence of a chiral center comprise a pair of non superimposable isomers that are called "enantiomers." Single enantiomers of a pure compound are optically active, i.e., they are capable of rotating the plane of plane polarized light.

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

By "isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well known chiral separation techniques. According to one such method, a racemic mixture of a compound having the structure of Formula I, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

The present invention further comprises compositions for inhibiting and/or killing activated lymphocytes, for inhibiting proliferating lymphocytes, and for treating diseases associated with such lymphocytes. One embodiment of the present invention includes compositions which, as demonstrated by the data disclosed herein, induce cell death and apoptosis in a variety of activated lymphocytes, including T cells and B cells. The compositions of the present invention include the compositions disclosed below.

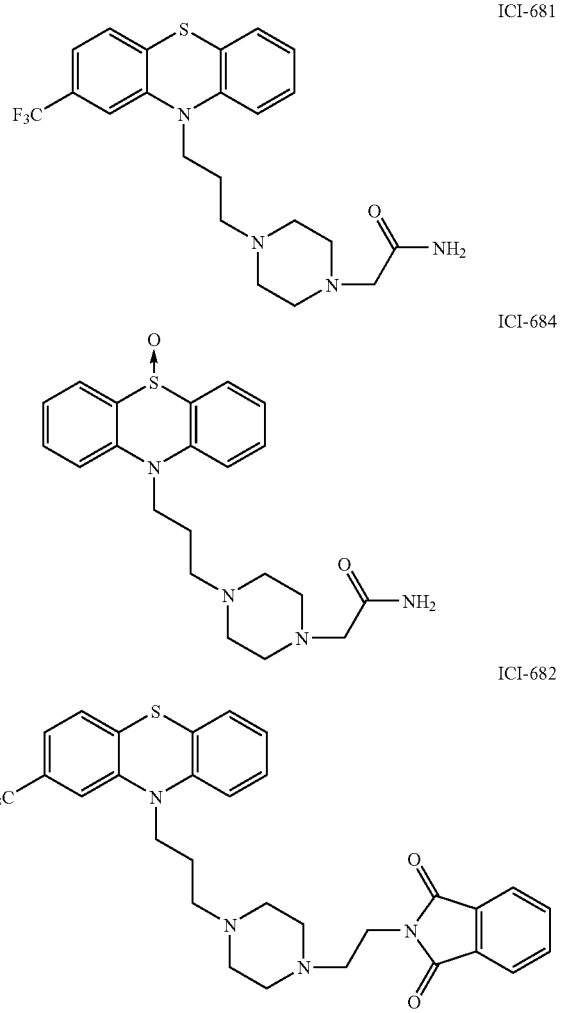

ICI-685
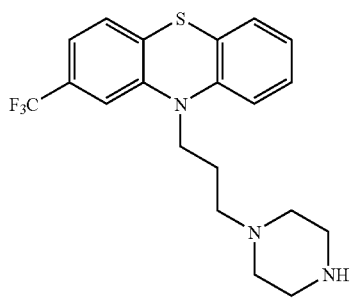
ICI-683
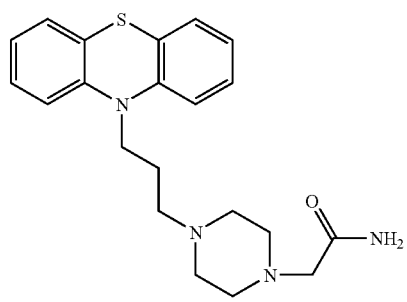
ICI-686
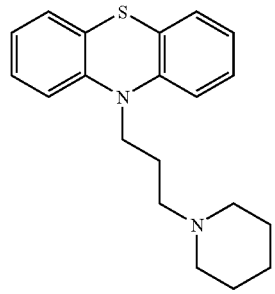
ICI-687
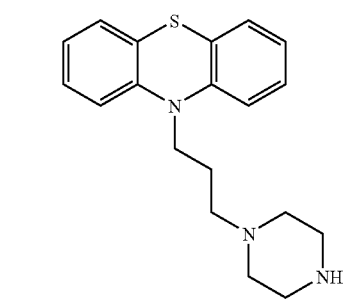
ICI-712
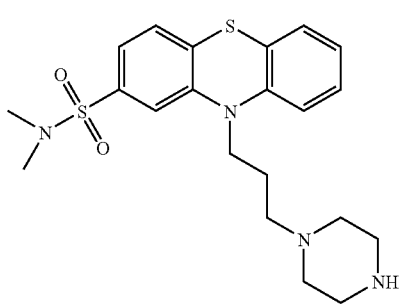
ICI-696
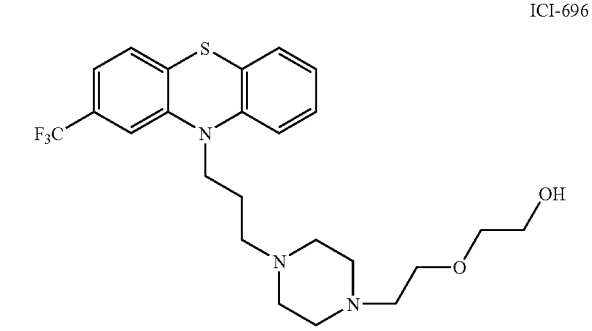
ICI-713
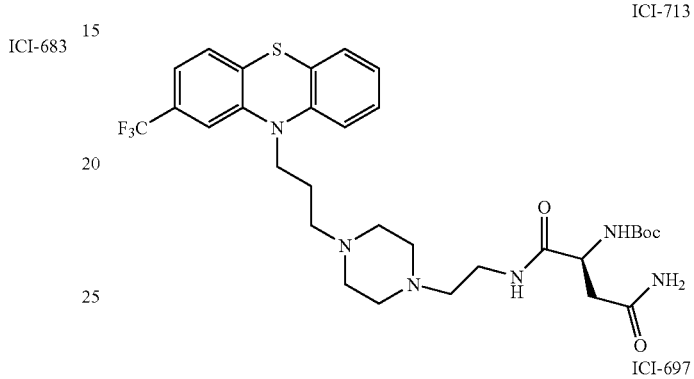
ICI-697
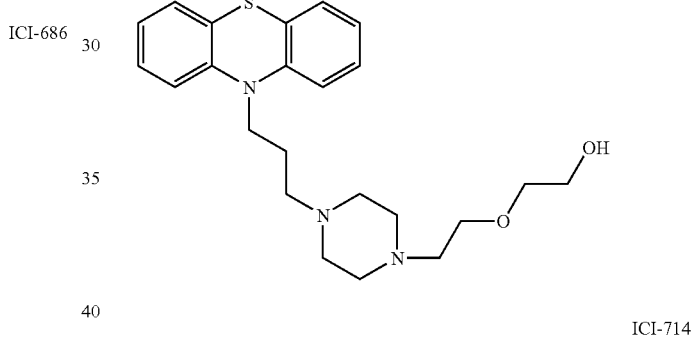
ICI-714
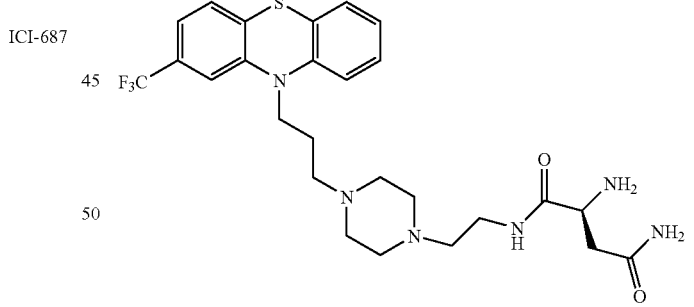
ICI-715
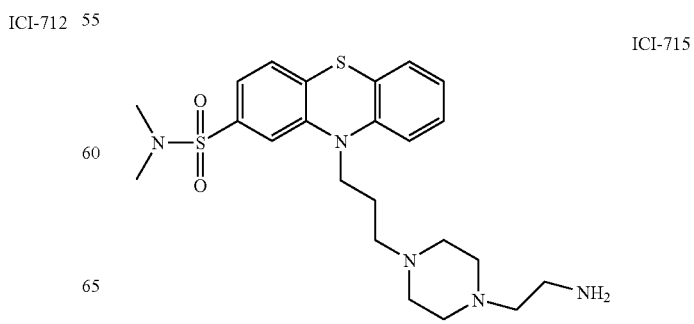

17
-continued
ICI-728
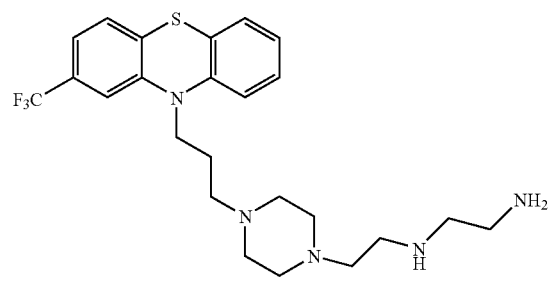
ICI-726
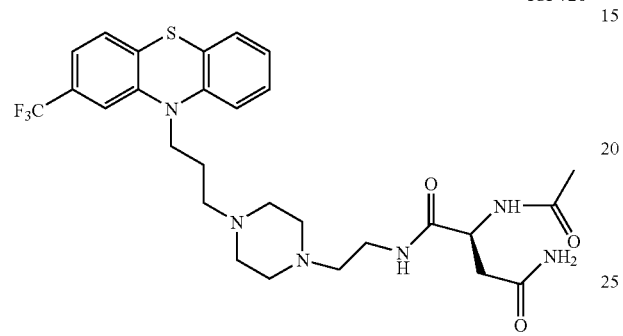
ICI-734
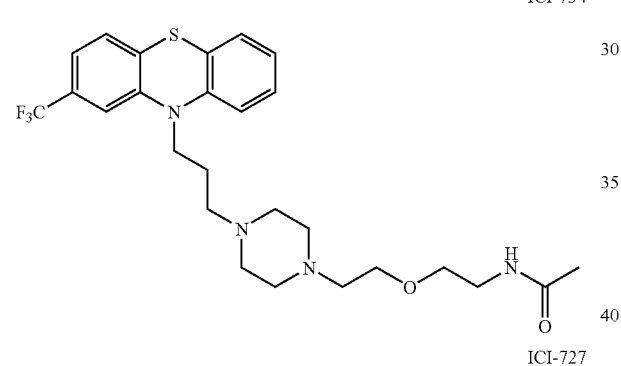
ICI-727
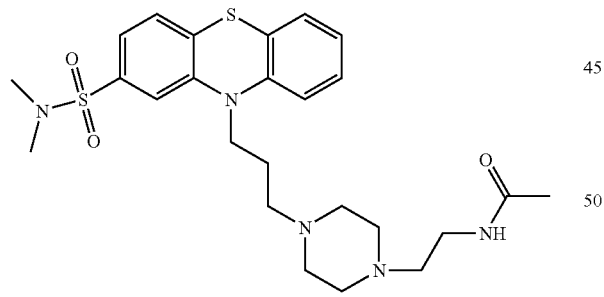
ICI-735
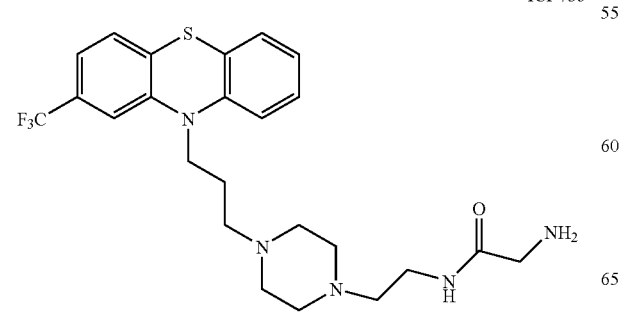
18
-continued
ICI-737
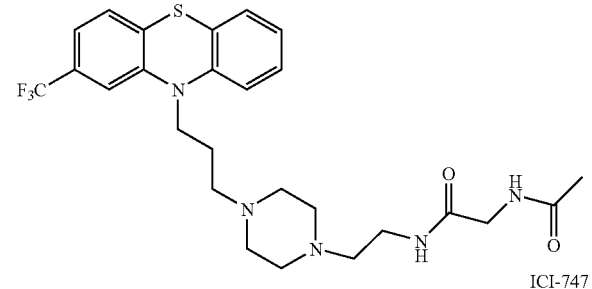
ICI-747
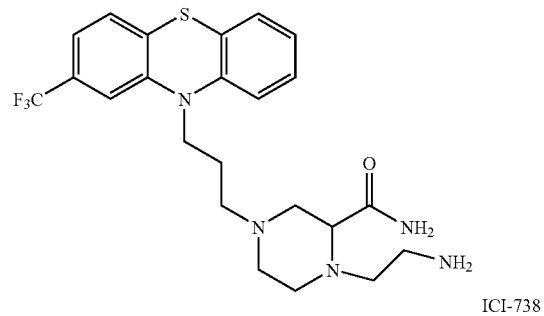
ICI-738
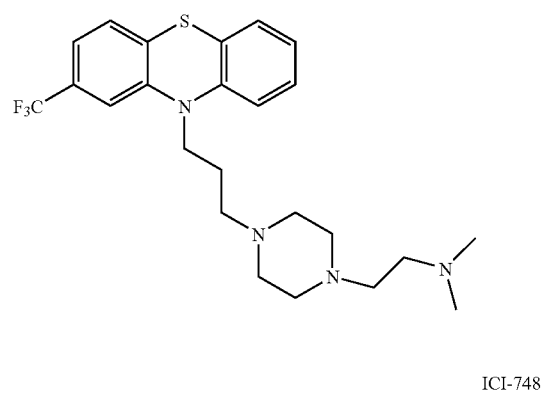
ICI-748
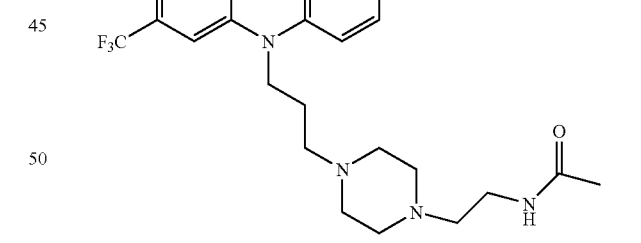
ICI-746
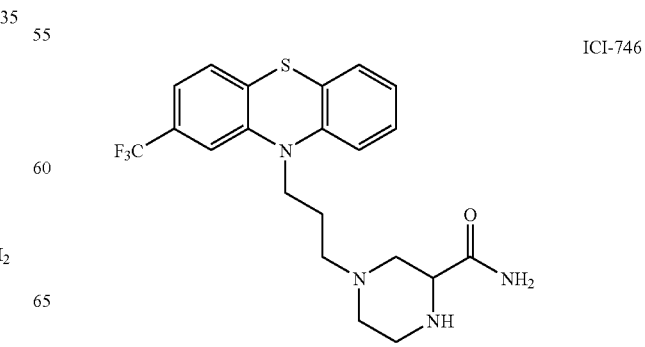

ICI-749
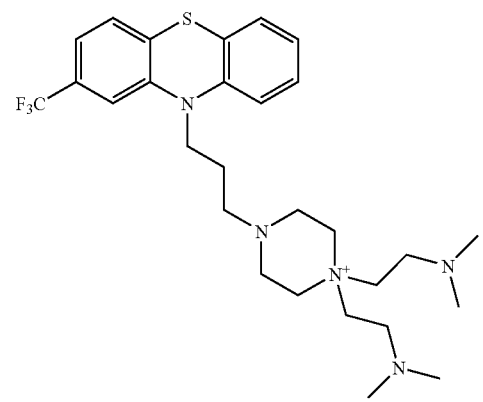
ICI-758
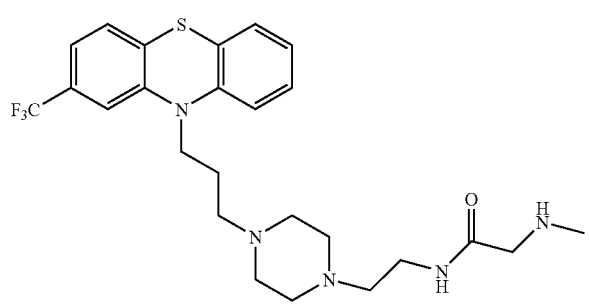
ICI-761
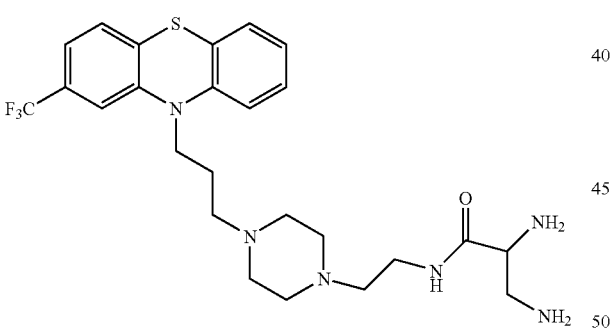
ICI-759
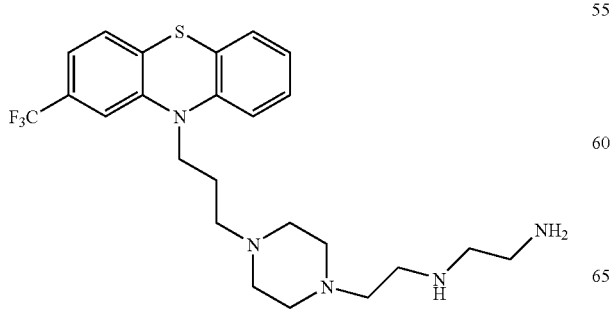
ICI-763
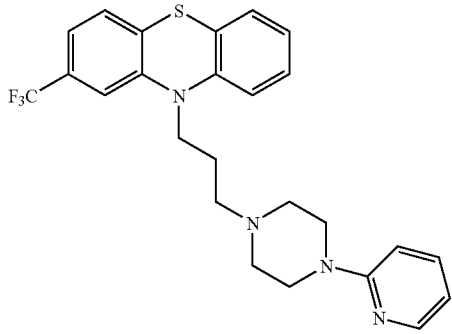
ICI-760, ICI-783, ICI-784, ICI-822
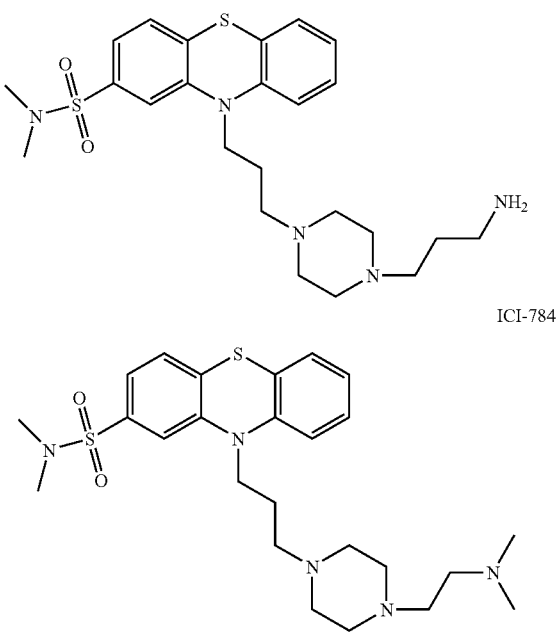

ICI-801
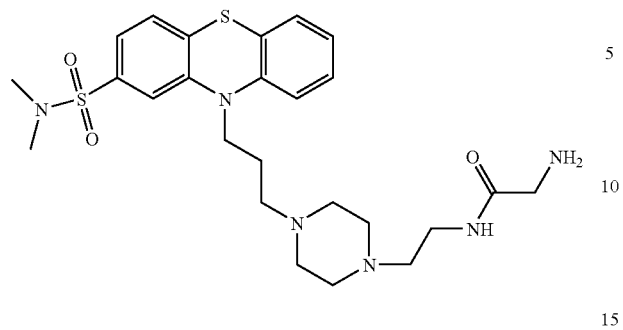
ICI-823
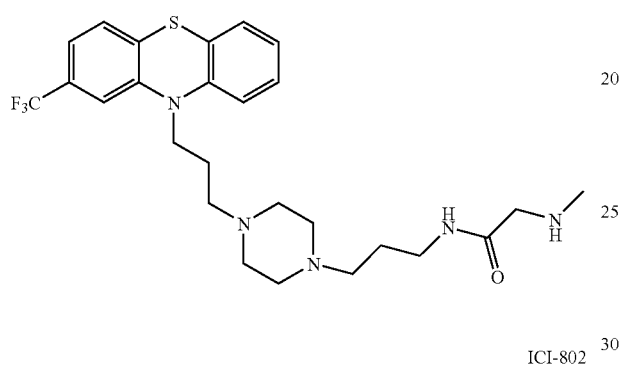
ICI-802
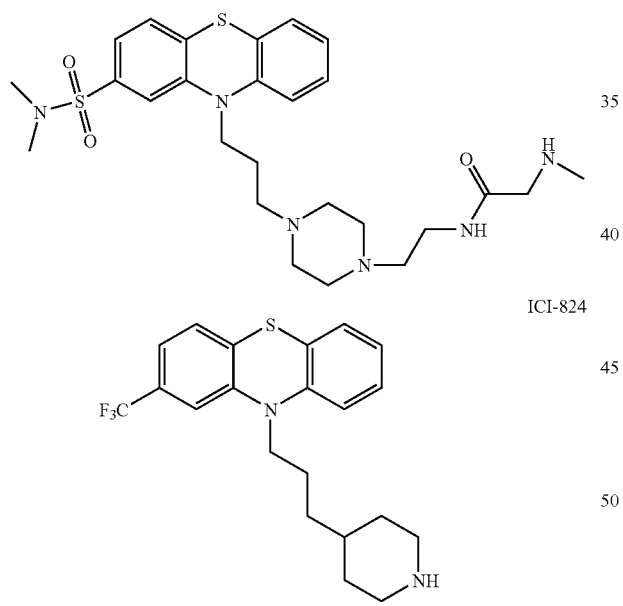
ICI-824
ICI-846
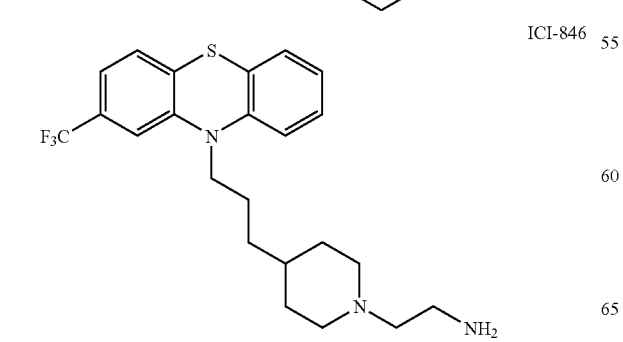
ICI-849
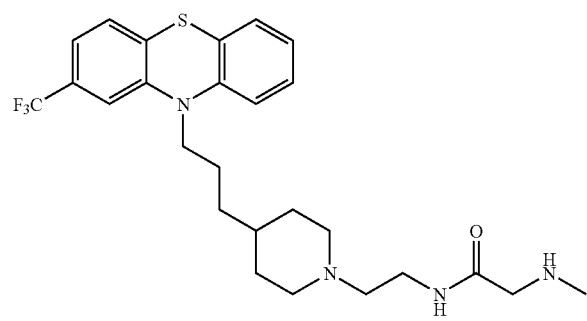
ICI-847
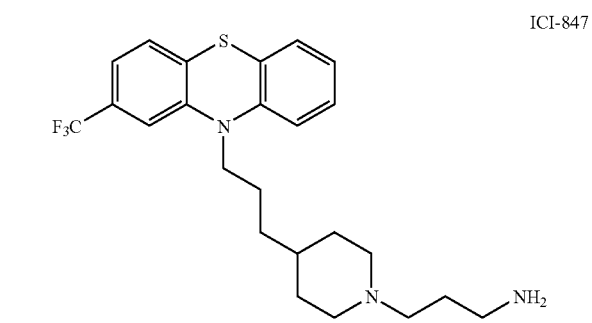
ICI-850
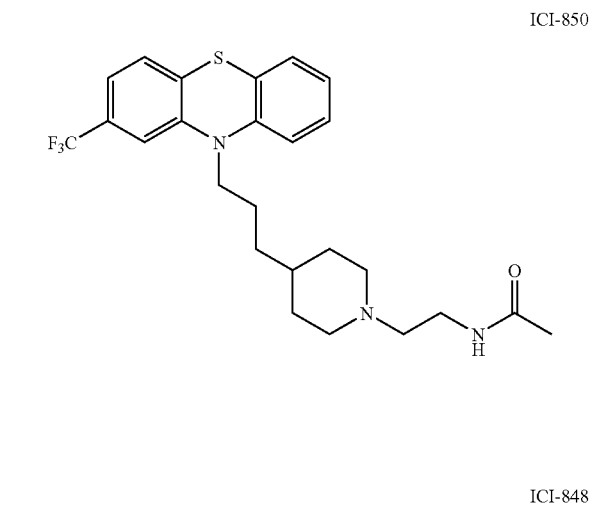
ICI-848
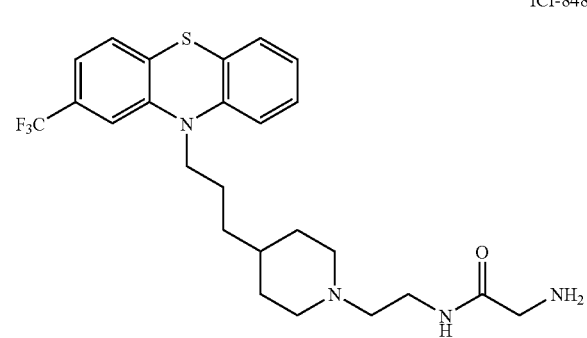

ICI-890

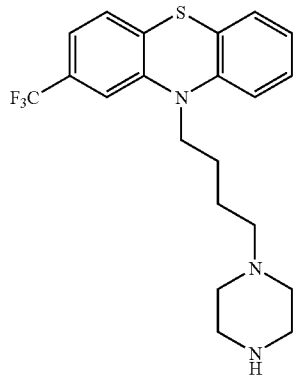

ICI-891

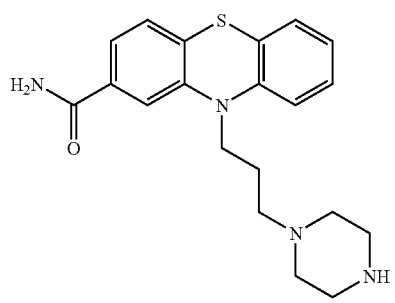

ICI-894

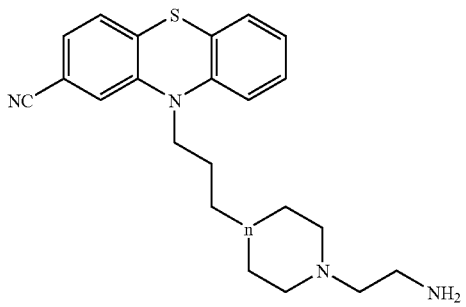

ICI-892

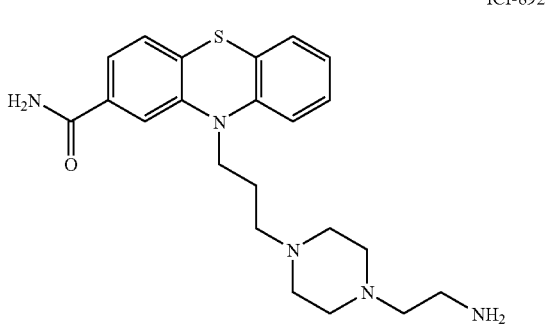

ICI-895

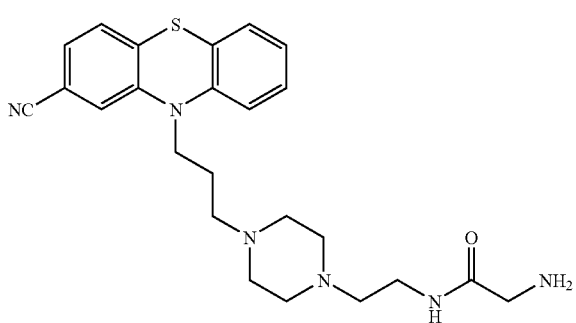

ICI-893

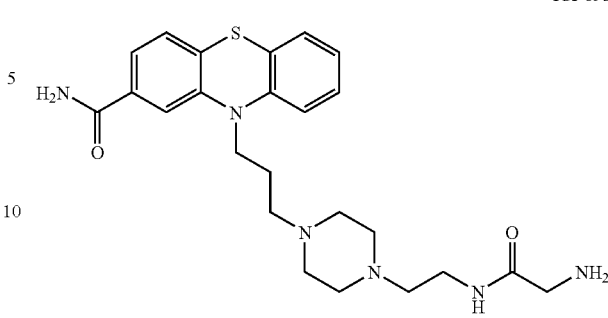

The compounds of the present invention can be used or administered as a pharmaceutically acceptable salt. The phrase "pharmaceutically acceptable salt(s)", as used herein, unless otherwise indicated, includes salts of acidic or basic groups which may be present in the compounds disclosed herein. The compounds disclosed herein that are basic in nature are capable of forming a wide variety of salts with various inorganic and organic acids. The acids that may be used to prepare pharmaceutically acceptable acid addition salts of such basic compounds of the present 5-HT receptor antagonists are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, dislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts. Since a single compound of the present invention may include more than one acidic or basic moieties, the compounds of the present invention may include mono, di or tri-salts in a single compound.

The 5-HT receptor antagonists of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

This invention also encompasses pharmaceutical compositions comprising prodrugs of the present 5-HT receptor antagonists. Compounds of formula I and the other 5-HT receptor antagonists disclosed herein having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds disclosed herein. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19: 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Free amines can also be derivatized as amides, sulfonamides or phosphonamides. All of these prodrug moieties may incorporate groups including but not limited to ether, amine and carboxylic acid functionalities.

The present invention also includes isotopically-labeled compounds, which are identical to those recited in the 5-HT receptor antagonists of the invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed herein and known in the art by substituting a readily available isotopically labeled reagent for a non-isotopically labeled reagent.

The compounds of the present invention can also be combined with other compounds useful in the treatment of diseases such as autoimmune diseases, lymphomas, myelomas, and transplant rejection. Such compounds include, but are not limited to, the following therapeutic agents: dexamethasone, melphalan, doxorubicin, bortezomib, lenalidomide, thalidomide, and other agents, such as, but not limited to, regulators of gene expression (e.g., steroids and glucocorticoids, alkylating agents that are known mutagens (e.g., cyclophosphamide), inhibitors of kinases and phosphatases which act on the calcineurin and JNK/p38 kinase pathways and the cyclin kinase cascade (e.g., CyclosporinA, Tacrolimus [FK506], and Rapamycin), inhibitors of de novo purine synthesis which act as inhibitors of guanosine nucleotide synthesis and are used to prevent allograft rejection and to treat ongoing rejection (e.g., Mycophenolate motefil), and inhibitors of de novo pyrimidine synthesis which are used to treat patients afflicted with rheumatoid arthritis (e.g., Leflunomide), TNF-α inhibitors, such as Adalimumab, Etanercept, Infliximab, and other immunomodulating agents, such as methotrexate, azathioprine, natalizumab, and mercaptopurine. Therefore, the invention encompasses a composition comprising a 5-HT receptor antagonist disclosed herein, such as a 5-HT receptor antagonist of formula I, and immunomodulating agent disclosed elsewhere herein.

A composition comprising a compound of the present invention, such as the 5-HT receptor antagonist of formula I or another compound disclosed herein, and a therapeutic agent are within the scope of the present invention, whether physically combined prior to administration to a patient or combined within a patient.

II. Methods

A. Methods of Inducing Apoptosis and Inhibiting Proliferation in a Lymphocyte

The present invention includes a method of inducing apoptosis in a lymphocyte. The method comprises inhibiting the interaction of serotonin with a serotonin receptor by contacting a lymphocyte with a 5-HT receptor antagonist, such as the 5-HT receptor antagonist of formula I or a 5-HT receptor antagonist disclosed elsewhere herein. In a preferred embodiment, the 5-HT receptor antagonist is a 5-HT receptor antagonist of formula I. More preferably, the 5-HT receptor antagonist is selected from, among others, ICI-685, ICI-715, ICI-735, ICI-824, ICI-846, ICI-847, ICI-848, ICI-849, ICI-890, ICI-894, ICI-953, and ICI-954. This is because, as demonstrated by the data disclosed herein, contacting a lymphocyte with a 5-HT receptor antagonist of the present invention results in, among other things, an inhibition of proliferation of a variety of lymphocytes, including T-cells and B-cells. In addition, the data disclosed herein demonstrates that contacting a lymphocyte with a 5-HT receptor antagonist of the present application results in apoptosis of the lymphocyte in a dose and time dependent manor. Thus, the present invention comprises inducing apoptosis in a lymphocyte and a method of inhibiting proliferation of a lymphocyte by contacting the lymphocyte with a 5-HT receptor antagonist.

The present invention further comprises a method of treating a mammal, preferably a human, having a disease characterized by abnormal lymphocyte proliferation where inhibiting lymphocyte proliferation or inducing apoptosis in the abnormally proliferating lymphocytes results in treatment of the disease. The method comprises administering an effective amount of a 5-HT receptor antagonist to a mammal, preferably a human, in need thereof. As demonstrated by the data disclosed herein, administration of a 5-HT receptor antagonist of the present invention results in, among other things, a rapid cessation of proliferation of various types of lymphocytes, including, but not limited to, T-cells and B-cells. In addition, according to the data presented herein, administration of a 5-HT receptor antagonist of the present invention results in apoptosis in the lymphocyte. Inducing apoptosis or inhibiting proliferation of a lymphocyte prevents or treats the generation of an immune response, such as those common to autoimmune diseases and transplant rejection, and also treats lymphatic neoplasias, including lymphomas and myelomas.

One of skill in the art would also appreciate, based upon the disclosure provided herein, that the invention encompasses using a 5-HT receptor antagonist that is water soluble and that does not substantially cross the blood-brain barrier. This is because one skilled in the art would understand that because serotonin receptors are found on neural cells and, as now disclosed, on cells of the immune system, including tumors derived from such cells (e.g., multiple myelomas, and the like), it is desirable, but not necessary, to inhibit signaling via serotonin receptor on an immune cell while not affecting serotonin signaling via a serotonin receptor on a neural cell. In such instances, administering a compound that inhibits signaling but does not cross the blood-brain barrier where it would affect serotonin signaling in neural cells is desirable.

Accordingly, the present invention encompasses using a compound that while inhibiting serotonin signaling via a serotonin receptor on a cell, does not substantially cross the blood-brain barrier. Such compounds are disclosed elsewhere herein and include the 5-HT receptor antagonist of formula I, as well as those disclosed elsewhere herein, but preferably includes ICI-685, ICI-715, ICI-735, ICI-824, ICI-846, ICI-847, ICI-848, ICI-849, ICI-890, ICI-894, ICI-953, and ICI-954.

One skilled in the art would understand, based upon the disclosure provided herein, that methods to modify a compound to affect its ability to cross the blood-brain barrier are well-known in the art, which also teaches a wide plethora of assays for assessing the ability of a substance to cross the barrier. One such method is disclosed herein, i.e., adding various sidegroups to a compound such as fluphenazine, thereby decreasing the ability of the modified fluphenazine to cross the blood-brain barrier. The modified fluphenazine compounds, designated, e.g., formula I, are disclosed herein, but the present application is in no way limited to these or any other particular derivatives of fluphenazine. Instead, the invention encompasses any compound having the desired immunomodulatory characteristics of the inhibitors of the invention, while also possessing the desired reduced ability to cross the blood-brain barrier. The production and identification of compounds having these characteristics are routine in the art, as are assays for assessing the permeability of a compound through the blood-brain barrier. Such assays are exemplified herein, as are methods of producing compounds of interest having the desired characteristics. Nonetheless, the present invention is in no way limited to these, or any other, methods in particular; rather, it includes methods of producing and identifying compounds that do not substantially cross the blood-brain barrier and still inhibit serotonin signaling via a serotonin receptor such as those disclosed herein, known in the art, or to be developed in the future.

The present invention can be used to treat a variety of autoimmune diseases, including, but not limited to, myasthenia gravis, idiopathic inflammatory myopathy, chronic neutropenia, rheumatoid arthritis, idiopathic thromcytopenia purpura, autoimmune hemolytic syndromes, antiphospholipid antibody syndromes, inflammatory bowel disease, Crohn's disease, ulcerative colitis, myocarditis, Guillian-Barre Syndrome, vasculitis, multiple sclerosis, neuromyelitis optica (devic's syndrome), lymphocytic hypophysitis, Graves disease, Addison's disease, hypoparathroidism, type 1 diabetes, systemic lupus erythematosus, pemphigus vulgaris, bullous pemphigoid, psoriasis, psoriatic arthritis, endometriosis, autoimmune orchitis, dystrophic epidermolysis, sarcoidosis, Wegener's granulomatosis, autoimmune deafness, Sjögren's disease, autoimmune uveoretinitis, interstitial cystitis, Goodpasture's syndrome, and fibromyalgia. This is because, as demonstrated by the data disclosed herein, the 5-HT receptor antagonists of the present invention inhibit the proliferation of both T cells and B cells, and additionally induce apoptosis in such lymphocytes. Thus, the methods of the present invention comprise administering an effective amount of a 5-HT receptor antagonist to a mammal, preferably a human, having an autoimmune disease, e.g. psoriasis.

The invention further comprises compounds and methods for treating asthma.

The present invention also comprises compositions and methods for the treatment of immune-cell related diseases and disorders. In an aspect, the disease or disorder is not autoimmune-related.

The present invention further comprises a method of treating organ transplant rejection in a mammal in need thereof. Specifically contemplated in the present invention are methods of treating graft versus host disease (GVHD) and organ transplant rejection by administering a 5-HT receptor antagonist disclosed herein to a patient suffering from GVHD and/or organ transplant rejection. The present invention comprises methods of treating, for example, transplant rejection of thoracic organs, such as heart transplants, lung transplants and en bloc heart/lung transplants. The methods of the invention further comprise treating rejection of abdominal organs, such as liver, kidney, pancreas, small bowel and combined transplants, such as kidney/pancreas transplants, liver/kidney transplants, and combined liver/small bowel transplants. The methods of the present invention further comprise treatment after rejection of a hand, cornea, skin or face transplant. In addition, the methods of the present invention can be used to treat rejection of tissues, cells and fluids that are commonly transplanted, including, but not limited to, pancreatic islet cells (islets of Langerhans), bone marrow transplants, adult stem cell transplants, blood transfusions, blood vessel grafts, heart valve grafts, where autologous, allogenic or xenogenic, and bone grafts. This is because, as demonstrated by the data disclosed herein, administering the 5-HT receptor antagonists of the present invention results in inhibited proliferation of T cells, one of the effector cells in transplant and graft rejection, and induces apoptosis in B cells, which produce anti-graft antibodies. Thus, the invention encompasses a method of treating transplant rejection by administering an effective amount of the 5-HT receptor antagonists of the present invention to a mammal, preferably a human, in need thereof.

The methods of the present invention further comprise treating a mammal having an autoimmune disease or a mammal rejecting an organ or tissue transplant with a combination of a 5-HT receptor antagonist with another immunomodulatory agent. Such immunomodulatory agents include, but are not limited to, other agents, such as, but not limited to, regulators of gene expression (e.g., steroids and glucocorticoids, alkylating agents that are known mutagens (e.g., cyclophosphamide), inhibitors of kinases and phosphatases which act on the calcineurin and JNK/p38 kinase pathways and the cyclin kinase cascade (e.g., CyclosporinA, Tacrolimus [FK506], and Rapamycin), inhibitors of de novo purine synthesis which act as inhibitors of guanosine nucleotide synthesis and are used to prevent allograft rejection and to treat ongoing rejection (e.g., Mycophenolate motefil), and inhibitors of de novo pyrimidine synthesis which are used to treat patients afflicted with rheumatoid arthritis (e.g., Leflunomide), TNF-α inhibitors, such as Adalimumab, Etanercept, Infliximab, and other immunomodulating agents, such as methotrexate, azathioprine, natalizumab, and mercaptopurine.

The immunomodulatory agents of the present invention can be combined with a 5-HT receptor antagonist of the present invention, such as the 5-HT receptor antagonist of formula I, ICI-685, ICI-715, ICI-735, ICI-824, ICI-846, ICI-847, ICI-848, ICI-849, ICI-890, ICI-894, ICI-953, or ICI-954 to treat a patient having an autoimmune disease or a patient experiencing transplant rejection. The immunomodulatory agent can be combined with a 5-HT receptor antagonist and delivered as one dose or a series of doses, either together or separately. Methods for the combinations of drugs and dosages are described elsewhere herein.

The present invention further comprises a method of treating neoplasias in a human, preferably lymphomas and myelomas. This is because, as demonstrated by the data disclosed herein, neoplastic lymphoma and myeloma cells, when contacted with a 5-HT receptor antagonist of the present invention, cease proliferating and apoptose. Thus, the present invention comprises methods for treating a mammal, preferably a human, having a lymphoma or a myeloma, the method comprising administering to the mammal an effective amount of a 5-HT receptor antagonist of the present invention. Such 5-HT receptor antagonists include, but are not limited to the 5-HT receptor antagonist of formula I, ICI-685, ICI-715, ICI-735, ICI-824, ICI-846, ICI-847, ICI-848, ICI-849, ICI-890, ICI-894, ICI-953, and ICI-954.

A mammal having a lymphoma can be treated using the methods of the present invention by administering to the mammal an effective amount of a 5-HT receptor antagonist of the present invention. Lymphomas that can be treated using the methods of the present invention include, but are not limited to, non-Hodgkin lymphomas, such as T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/Sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, and anaplastic large cell lymphoma. The present invention further comprises methods of treating Hodgkin's lymphomas by administering to a patient having a Hodgkin's lymphoma an effective amount of a 5-HT receptor antagonist of the present invention. Such Hodgkin's lymphomas include, but are not limited to, nodular lymphocyte-predominant Hodgkin lymphoma and classical Hodgkin lymphoma, including nodular sclerosis, mixed cellularity Hodgkin's lymphoma, lymphocyte-rich Hodgkin's lymphoma and lymphocyte depleted Hodgkin's lymphoma.

The methods of the present invention further comprise treating a mammal, preferably a human, with myeloma. This is because, as demonstrated by the data disclosed herein, the 5-HT receptor antagonists of the present invention inhibit the proliferation and induce apoptosis in a variety of common myeloma cells, including primary multiple myeloma cells from treated and untreated patients, and multiple myeloma cells resistant to conventional multiple myeloma therapeutics, such as dexamethasone and melphalan.

The methods of the present invention are used to treat multiple myeloma in a patient in need thereof. The method comprises administering to a patient in need thereof a fluphenazine inhibitor of the present invention. This is because, as disclosed elsewhere herein, contacting a multiple myeloma cell with a 5-HT receptor antagonist of the present invention, such as the 5-HT receptor antagonist of formula I, ICI-685, ICI-715, ICI-735, ICI-824, ICI-846, ICI-847, ICI-848, ICI-849, ICI-890, ICI-894, ICI-953, or ICI-954 causes an inhibition of proliferation of the multiple myeloma cell as well as induces apoptosis in a multiple myeloma cell. Thus, the present invention comprises a method of treating multiple myeloma in a mammal, preferably a human. Further, as demonstrated by the data herein, the present invention comprises a method of inducing apoptosis in a multiple myeloma cell, whether in a patient or isolated from the patient, by contacting the multiple myeloma cell with a fluphenazine inhibitor of the present invention.

The present invention is used to treat multiple myeloma of all stages on the International Staging System (ISS), including Stage I: $\beta$2-microglobulin <3.5 mg/L, albumin $\geq$3.5 g/dL; Stage II: $\beta$2-microglobulin <3.5 mg/L and albumin <3.5 g/dL or $\beta$2-microglobulin between 3.5 and 5.5 mg/L; and Stage III: $\beta$2-microglobulin >5.5 mg/L. In addition, the methods of the present invention comprise combination therapy for treating multiple myeloma. The combinations of the present invention comprise a 5-HT receptor antagonist, such as the 5-HT receptor antagonist of formula I, ICI-685, ICI-715, ICI-735, ICI-824, ICI-846, ICI-847, ICI-848, ICI-849, ICI-890, ICI-894, ICI-953, or ICI-954 combined with an additional agents and therapies used for treating multiple myeloma. Specifically contemplated combination therapies include a 5-HT receptor antagonist administered before or after allogeneic or autologous stem cell transplantation, a 5-HT receptor antagonist and a bisphosphonate (e.g. pamidronate) to prevent fractures, and a 5-HT receptor antagonist and erythropoietin to treat anemia associated with multiple myeloma.

Additional combination therapies specifically contemplated in the present invention include a 5-HT receptor antagonist and dexamethasone with or without thalidomide, a 5-HT receptor antagonist and thalidomide, a 5-HT receptor antagonist and vincristine, a 5-HT receptor antagonist and doxorubicin, a 5-HT receptor antagonist and melphalan, and a 5-HT receptor antagonist with melphalan and prednisone. In relapsed patients, or patients otherwise not responding to conventional multiple myeloma therapies, the invention encompasses methods of treating multiple myeloma in a patient comprising administering combinations of a 5-HT receptor antagonist and cyclophosphamide, a 5-HT receptor antagonist and bortezomib or a 5-HT receptor antagonist and lenalidomide. The renal failure that often accompanies multiple myeloma can be treated using a 5-HT receptor antagonist of the present invention and kidney dialysis.

The combinations of a 5-HT receptor antagonist- and another multiple myeloma therapy are, as demonstrated by the data disclosed herein, effective at inhibiting proliferation and inducing apoptosis in multiple myeloma cells. As a non-limiting example, nanomolar concentrations of the present 5-HT receptor antagonists and other multiple myeloma therapies resulted in, among other things, increased apoptosis and decreased proliferation when compared to conventional multiple myeloma therapies alone.

As further demonstrated by the data disclosed herein, the 5-HT receptor antagonists of the present invention induce apoptosis and inhibit proliferation in a variety of lymphocytes, and thus are useful in the treatment of various immune system related diseases. Thus, the present invention further comprises a method of inhibiting an immune response in a mammal, preferably a human, by inhibiting serotonin binding with a serotonin receptor by administering a 5-HT receptor antagonist of the present invention, thereby inhibiting an immune reaction by the cell, which in turn inhibits an immune response mediated by that cell. The invention further comprises a method of inhibiting an immune reaction by an immune cell. This is because, as set forth elsewhere herein, inhibition of serotonin binding with a serotonin receptor on the immune cell inhibits activation of the cell, which in turn inhibits an immune reaction by that cell when compared to the immune reaction by that cell in the absence of inhibition of serotonin binding and/or when compared with the immune reaction of an otherwise identical cell wherein serotonin binding with its receptor is not inhibited. The present invention further encompasses a method of inhibiting activation of an immune cell, such as a lymphocyte, in a mammal, preferably, a human, wherein the activation is mediated by activation of a serotonin receptor on the cell. Again, this is because, as more fully set forth elsewhere herein, the data disclosed herein demonstrate that inhibiting serotonin signaling via a serotonin receptor on an immune cell by contacting the cell with a 5-HT receptor antagonist inhibits activation of the cell, and therefore, also inhibits the immune response that would otherwise be produced by that cell.

The 5-HT receptor antagonist, alone or in combinations described herein, that inhibits the serotonin receptor-mediated signals can be administered to a cell, a tissue, or an animal to inhibit interaction of serotonin with a serotonin type receptor on a cell, a tissue, or in an animal. Methods for the safe and effective administration of the 5-HT receptor antagonists described herein are know to those skilled in the art. For instance, the administration of serotonin antagonists is described in the standard literature. That is, the administration of many serotonin-affecting agents, serotonin receptor antagonists, and fluphenazine is set forth in the Physician's Desk Reference (1996 edition, Medical Economics Co., Montvale, N.J.), the disclosure of which is incorporated by reference as if set forth in its entirety herein.

For administration of a 5-HT receptor antagonist of the present invention to a mammal, the compound can be suspended in any pharmaceutically acceptable carrier, for example, sterile water or a buffered aqueous carriers, such as glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, bolus injection, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration.

Compounds which are identified using any of the methods described herein may be formulated and administered to a mammal for treatment of immune system conditions (i.e., autoimmune diseases and allograft rejection), are now described.

The invention encompasses the preparation and use of pharmaceutical compositions comprising a compound useful for treatment of a wide variety of disorders such as T cell lymphomas, autoimmune disorders (see infra), complications arising from solid organ transplants, skin graft rejection, graft versus host disease in bone marrow transplants, multiple myeloma, and the like.

The pharmaceutical compositions described herein can be prepared alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, bolus injections, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, and the like. Preferably, the compound is, but need not be, administered as a bolus injection that provides lasting effects for at least one day following injection. The bolus injection can be provided intraperitoneally.

Thus, the skilled artisan would appreciate, once armed with the teachings provided herein, that the invention encompasses administration of a bolus comprising an inhibitor of the interaction of serotonin with a serotonin receptor, preferably the inhibitor is a 5-HT receptor antagonist of formula I, ICI-685, ICI-715, ICI-735, ICI-824, ICI-846, ICI-847, ICI-848, ICI-849, ICI-890, ICI-894, ICI-953, or ICI-954. Without wishing to be bound by any particular theory, administration of a bolus dose mediates apoptosis of certain cells, such as, among others, an activated T cell or a cancerous B cell (such as, e.g., a multiple myeloma cell), such that repeated doses of the inhibitor is not necessary since the bolus mediates the death of memory, or other, cells that would otherwise mediate the immune response that would otherwise cause the transplanted cell or tissue to be rejected. This effect can be mediated by a localized concentration of a 5-HT receptor antagonist at the 5HTR1B receptor, which concentration is sufficient to inhibit transmission of the serotonin signal, thereby mediating cell death and/or inhibition of an immune response by the cell.

III. Kits

The invention encompasses various kits relating to inhibiting the interaction of serotonin with a serotonin receptor because, as disclosed elsewhere herein, inhibiting this interaction in turn inhibits activation of an immune cell thereby inhibiting an immune response. Thus, in one aspect, the invention includes a kit for modulating an immune response in a mammal. The kit comprises an effective amount of an inhibitor of the interaction of serotonin with a serotonin receptor. Such an inhibitor includes, preferably, a serotonin receptor antagonist. And the kit further comprises an applicator and an instructional material for the use thereof.

Additionally, one skilled in the art would appreciate, based upon the disclosure provided herein, that the inhibitor can be a compound that does not cross the blood-brain barrier and is preferably water soluble. This is because, as more fully discussed elsewhere herein, it may be desirable to inhibit serotonin signaling in a non-neural cell, while not affecting such signaling in a neural cell, which would be protected beyond the blood-brain barrier.

In a specific embodiment, the kit of the present invention comprises a 5-HT receptor antagonist, an applicator, and an instructional material for the use thereof. In another embodiment, the kit can comprise a 5-HT receptor antagonist, such as those described elsewhere herein, a container holding the 5-HT receptor antagonist, and an instructional material. The skilled artisan can provide the applicator.

Preferably, the kit of the present invention comprises a 5-HT receptor antagonist of formula I, ICI-685, ICI-715, ICI-735, ICI-824, ICI-846, ICI-847, ICI-848, ICI-849, ICI-890, ICI-894, ICI-953, or ICI-954. Additionally, the kit can comprise an instructional material and an applicator for the administration of a 5-HT receptor antagonist of the present invention.

The kits of the present invention can be used to treat the diseases and conditions disclosed elsewhere herein. Specifically, the kits of the present invention can be used to treat, among other things, autoimmune diseases, such as psoriasis, organ transplant rejection, such as kidney transplant rejection, lymphoma, such as Hodgkin's lymphoma or non-Hodgkin's lymphoma, and B-cell neoplasias, such as multiple myeloma. The kits described in the present invention are not limited to the uses above however, and can be used in any method derived from the teachings disclosed herein.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Example 1

Efficacy of 5-HT Receptor Antagonists in Cell Lines

Cell Lines

Cell lines used in these studies were obtained from the American Type Culture Collection (ATCC; Manassas, Va.) or were otherwise obtained as indicated and were maintained under standard laboratory growth conditions. The neoplastic T-cell lines used in the studies included CCRF-CEM cells, a CD4+ lymphoblastic T-cell leukemia line (Foley et al., 1965, Cancer 18: 522-529). The B-cell neoplastic cell lines used were as follows: RPMI 8226 (a plasmacytoma derived from a multiple myeloma patient (Matsuoka, et al., 1967, Proc. Soc. Exp. Biol. Med. 125: 1246-1250), U266 (established from an IgE-secreting myeloma patient (Nilsson, et al., 1970, Clin. Exp. Immunol., 7: 477-489) and ARH77 (an EBV transformed plasma cell leukemia (Burk, et al., 1978, Cancer Res. 38: 2508-2513). The MM1 S cells, a dexamethasone sensitive cell line derived from the MM1 cell clone, isolated from an IgA-secreting myeloma patient in the leukemic phase, (Goldman-Leikin, et al., 1989, Lab. Clin. Med., 113: 335-345), were a kind gift from Dr. Kenneth Anderson. BE(2)-C is a clone of the SK-N-BE(2) neuroblastoma cell line (see ATCC CRL-2271) that was established in November of 1972 from a bone marrow biopsy taken from child with disseminated neuroblastoma after repeated courses of chemotherapy and radiotherapy. BE(2)-C was deposited at the ATCC by June L. Biedler, Memorial Sloan-Kettering Cancer Center. The RPMI-Dox 40 cell line (Dalton and Salmon, 1992, Hematol. Oncol. Clin. North Am., 6: 383-393) and the RPM1-LR5 (Hideshema, et al., 2005, Proc. Nat'l. Acad. Sci. USA, 102: 8567-8572 are doxorubicin-resistant and melphalan-resistant multiple myeloma cell lines, respectively. Dexamethasone-sensitive (MMIS) and -resistant (MM1R) human multiple myeloma cell lines, as well as the dexamethasone-sensitive (OPM-2) and -resistant (OPM-1) multiple myeloma cell lines were used (Gomi, et al., 1990, Cancer Res. 50: 1873-1878). All multiple myeloma cell lines were cultured in RPMI medium 1640 containing 10% FBS (Sigma, St. Louis, Mo.), 2 µM L-glutamine, 100 units/ml penicillin, and 100 µg/ml streptomycin (Gibco, La Jolla, Calif.).

Primary multiple myeloma patient plasma cells were purified from bone marrow aspirates by negative selection by using an antibody mixture (RosetteSep Separation System, StemCell Technologies, Vancouver) as described in Hideshima, et al., (2003, Blood 101: 1530-1534). The purity of MM cells was >90%, as confirmed by flow cytometric analysis using anti-CD138 Ab (Pharmingen, San Jose, Calif.).

[$^3$H]-Thymidine Incorporation Assays

Cells were harvested from culture media and washed three times in 20 mL room temperature Hanks Balanced Salt Solution (HBSS) by centrifugation. Cells were plated in 96-well plates (Corning-Costar, Acton, Mass.) at a density of 5×10$^4$ cells per 180 µL complete growth media. Following addition of cells, test agents were added to culture wells in a volume not exceeding 20 µL for aqueous vehicle or a 0.05% final concentration of DMSO vehicle. Untreated samples contained an equivalent concentration of vehicle as a control. Proliferation assays were carried out for the time indicated following drug addition and pulsed with 1 µCi [$^3$H]-thymidine (NEN-Life Sciences, Boston, Mass.) during the final 6 hours of culture. At the completion of the assay, cells were harvested on glass fiber filters using a PHD harvester (Brandel, Gaithersburg, Md.). Filters were soaked overnight in 3 mL CytoScint scintillation fluid (ICN Biomedicals, Irvine, Calif.) and counted using a β-counter (Becton Dickinson, San Jose, Calif. All samples were performed in at least triplicate.

Colorimetric MTT Assays for Cell Viability

Cells were harvested and treated with the indicated concentrations of drug as described for [$^3$H]-thymidine incorporation assays and trypan-blue exclusion studies, except that the volume contained in each well was reduced to 100 μL. Assays were carried out for the indicated time following drug addition. Prior to the completion of assays, 50 mg MTT reagent (3-(4,5-dimethylthiazon-2-ly)-2,5-diphenyl tetrasodium bromide) was dissolved in 10 mL PBS, pH 7.4, as per the manufacture's directions. At the completion of assays, 10 μL dissolved MTT reagent was added to each well, mixed by gentle agitation and incubated at 37° C. in tissue culture incubators for 4 hours. 100 μL isopropanol/0.04N HCl was added to each well and mixed thoroughly by repeated pipetting. Absorbance was measured using an ELISA plate reader at wavelength of 570 nm. All samples were plated in at least quadruplicate for MTT assays.

Trypan Blue Exclusion Studies

Cells were harvested and treated with indicated concentrations of drug as described above for [$^3$H]-thymidine incorporation assays. Assays were carried out for the indicated number of hours following drug addition. At the completion of the assay cells were harvested from 96-well plates and washed and re-suspended in HBSS. Cell suspensions were then stained with a 1:2 dilution of 0.4% (w/v) trypan-blue solution for approximately 15 minutes. Viable cells (un-stained with trypan-blue) were enumerated using a hemocytometer.

Assessing Apoptosis by Annexin V Binding

Cells are harvested, washed twice in cold PBS (4° C.) and resuspended at a concentration of 1×10$^6$ cells/ml in binding buffer (10×; 0.1M HEPES/NaOH, pH 7.4; 140 mM NaCl; 25 mM CaCl$_2$). Cells (100 μl) are aliquoted into FACS tubes and Annexin V die is added. Tubes are mixed gently and incubated at room temperature for 15 minutes in the dark. Binding buffer (400 μl) is added to each tube and analyzed via flow cytometry.

The results of the experiments presented in this Example are now described.

The MTT assay was employed for measuring cellular proliferation, or lack thereof, in several lines, including several strains of multiple myeloma cells. MTT assays measure the amount of yellow MTT (3-(4,5-Dimethylthiazol-2-yl)-2,5-diphenyltetrazolium bromide) reduced to purple formazan when mitochondrial reductase enzymes are active, thus directly measuring the number of viable cells (Mosmann, 1993, J. Immunol. Meth., 65: 55-63). The production of formazan in cells treated with a 5-HT receptor antagonist was measured relative to the production in control cells, and a dose-response curve was generated.

HeLa cells, the T cell lymphoma line CCRF-CEM, and the multiple myeloma cell line RPMI-8226 were treated with the selective 5-HT1B antagonists SB 216641, ICI-822, ICI-823, ICI-824, ICI-846, ICI-847, ICI-848, ICI-849, ICI-850, ICI-685, ICI-715, ICI-735, ICI-890, ICI-891, ICI-892, ICI-893, ICI-894, ICI-895, ICI-953, ICI-956, ICI-954, ICI, 955 and ICI-957 and cell viability and proliferation were then measured using an MTT assay (FIGS. 1-6 and 15-25). Loss of viability and proliferation inhibition were pronounced in the T cell and multiple myeloma cell lines (FIGS. 2-3,5-6, 15-16, 18-21, and 23-25) compared to HeLa cells.

Treatment of Arthritis Using Compounds of the Invention

Figure 26:
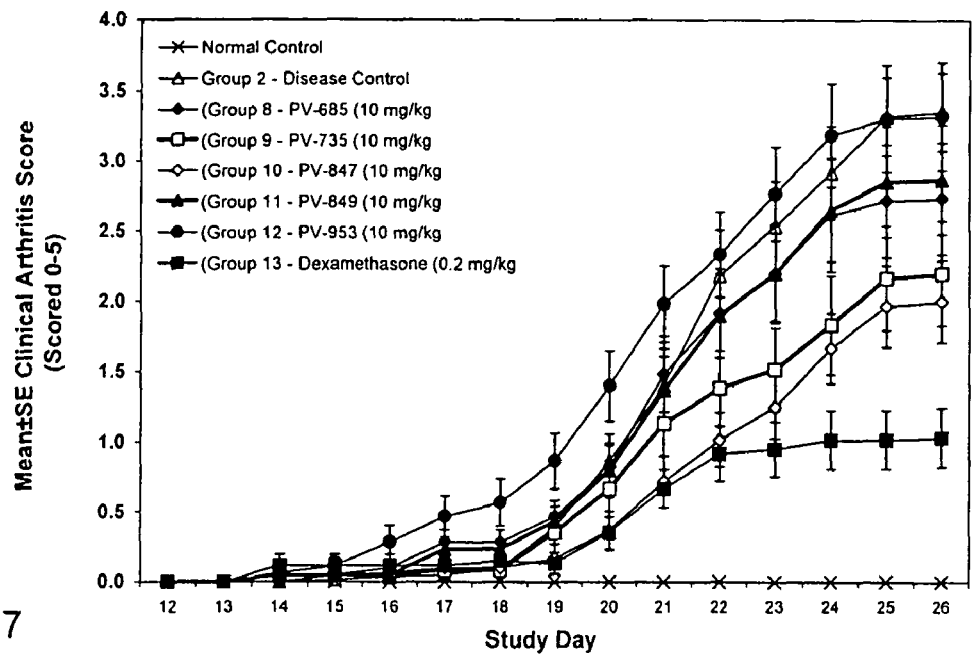
FIG. 26 is a graph depicting the clinical arthritis score over time for mice treated with various compounds of the invention.
Figure 27:
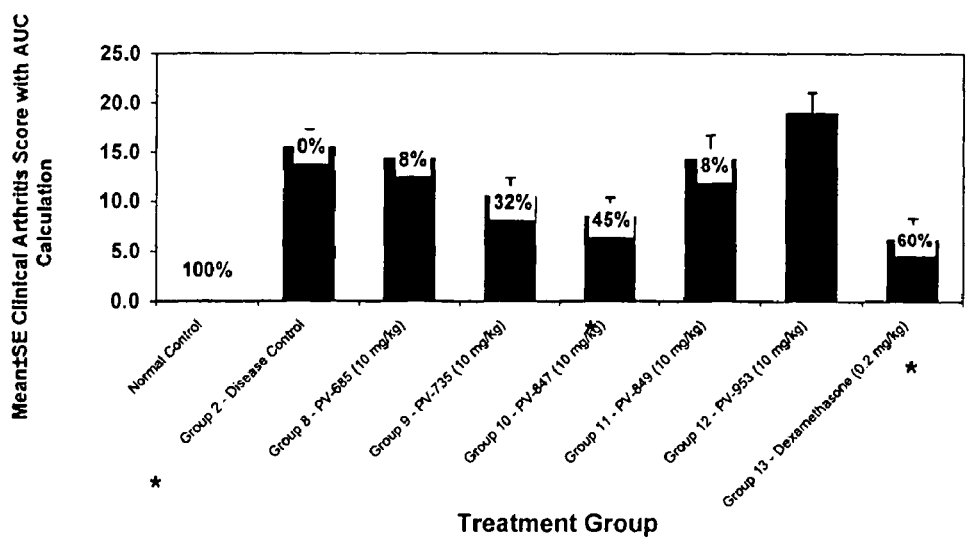
FIG. 27 is a graph depicting the clinical arthritis score, with AUC calculation, for mice treated with various compounds of the invention.
Figure 28:
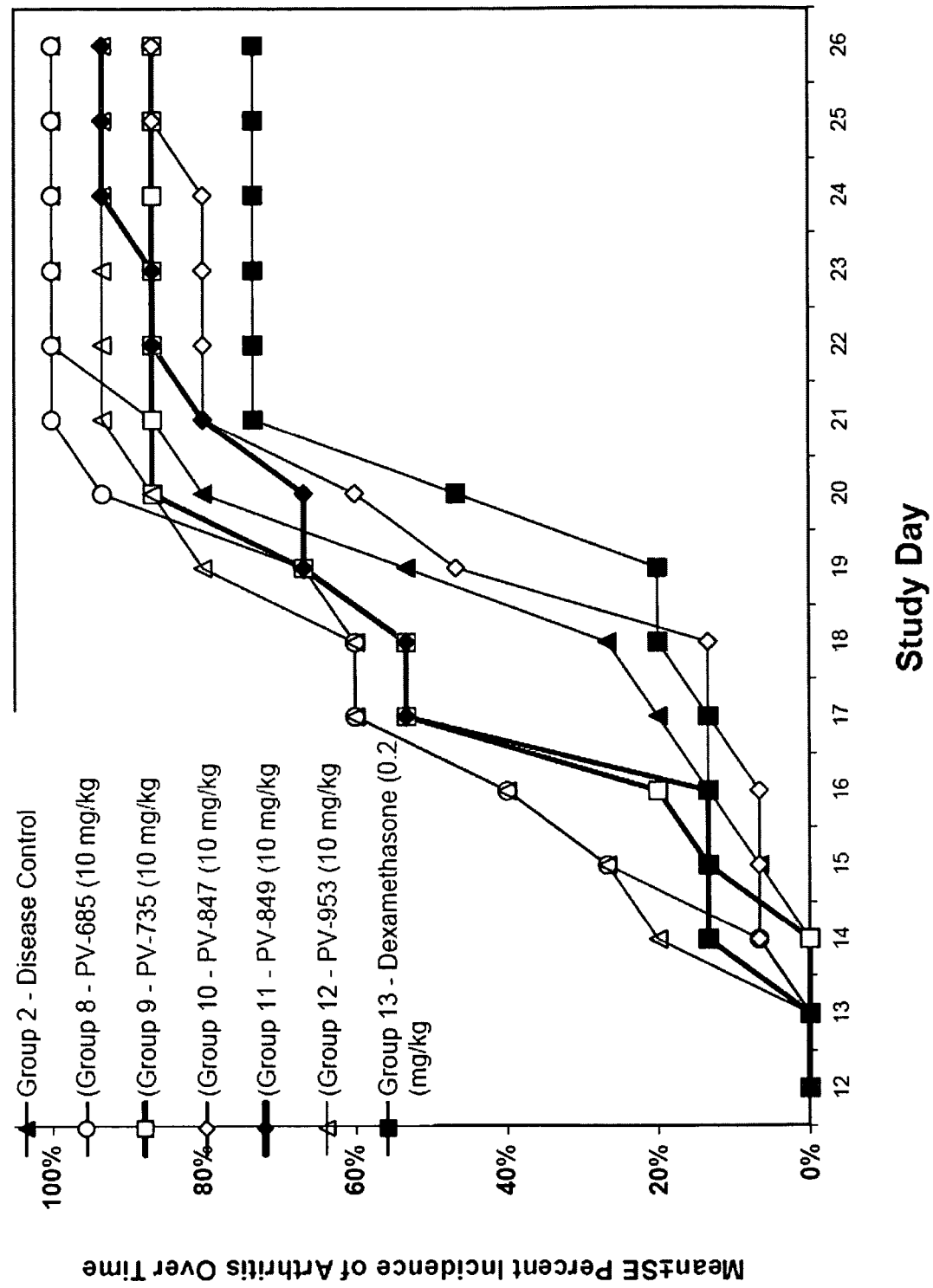
FIG. 28 is a graph depicting the incidence of arthritis over time for mice treated with various compounds of the invention.

FIGS. 26-28 illustrate the effect of various compounds of the invention on the clinical arthritis score of mice treated with various compounds of the invention. Notably, FIG. 26 illustrates that ICI-847, delivered orally at 10 mg/kg daily, for about 21 days, is as effective as dexamethasone in mice sensitized with collagen injections, resulting in the same clinical arthritis score as dexamehtasone, a standard rheumatoid arthritis (RA) animal model.

Figure 29:
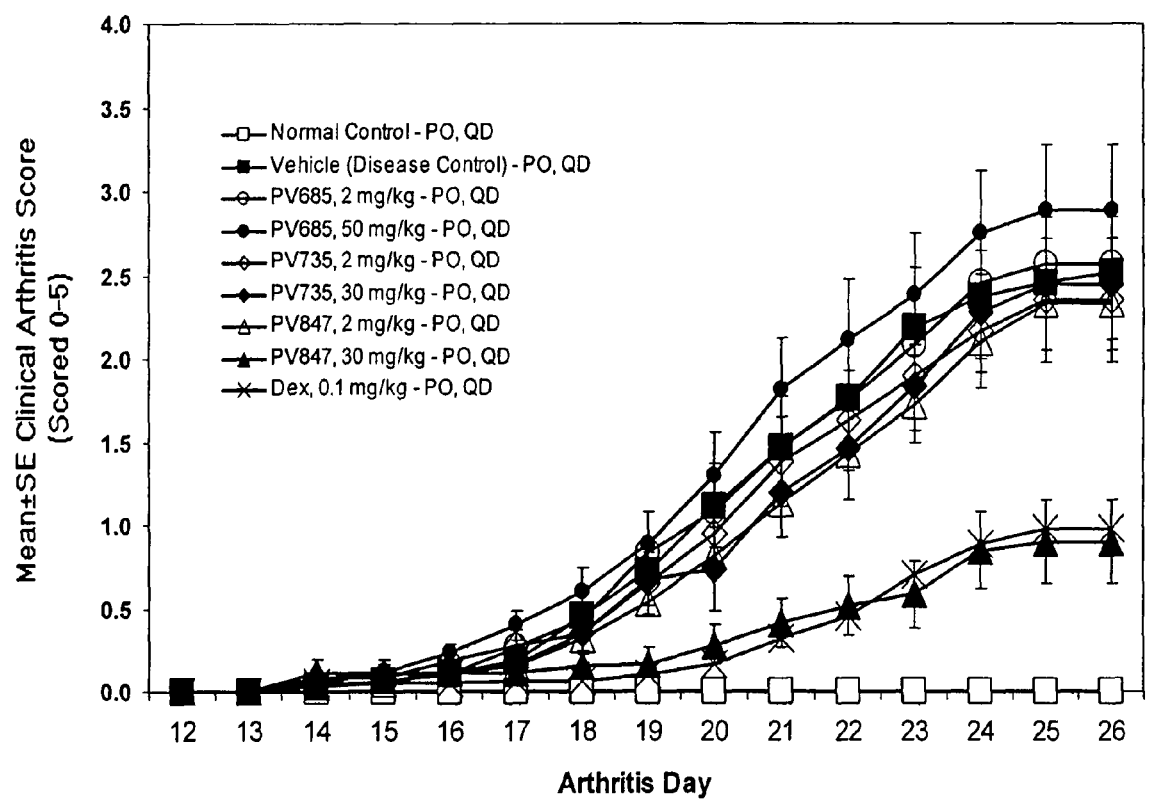
FIG. 29 is a graph depicting the clinical arthritis score over time for mice treated with various concentrations of selected compounds of the invention.

Additional testing of the effectiveness of compounds ICI-685, ICI-735 and ICI-847 at higher and lower concentrations were conducted, as illustrated in FIG. 29. These data illustrate the effectiveness of ICI-847 at treating rheumatoid arthritis (RA), and the symptoms of RA, and illustrates that at 30 mg/kg, ICI-847 is as effective for the length of the study as is dexamethasone.

Dexamethasone is a well-known compound used for treatment of arthritis, among other inflammatory diseases. The present experimental results therefore suggest that compounds of the invention can be useful for treating arthritis and related conditions.

Treatment of Asthma Using Compounds of the Invention

Compounds of the invention were also tested for efficacy in an asthma model. Table 1 demonstrates the efficacy of compounds of the invention in treating asthma in an asthma model. Table 1 illustrates that both ICI-847 and ICI-735, delivered intraperitoneally at a dose of 20 mg/ml, were at least as effective as dexamethasone at decreasing lung resistance in an *Aspergillus fumigatus*-based mouse asthma model.

A cohort of mice were administered intraperitoneal injections of *Aspergillus fumigatus* on days 0, 14, 26, 27, and 28. Lung resistance was tested on day 29 immediately following a tracheotomy/methacholine procedure. Animals receiving dexamethasone were administered dexamethasone on days 26, 27 and 28. Animals receiving a compound of the invention were administered the compound just hours before the lung resistance test. As a control, all test compounds, as well as dexamethasone, were also administered to mice in the absence of an *A. fumigatus* insult. All animals treated with compound but not with *A. fumigatus* had a baseline value of about 3 in the lung resistance test.

Dexamethasone is a well-known compound used for treatment of asthma, among other inflammatory diseases. The present experimental results therefore suggest that compounds of the invention can be useful for treating asthma and related conditions.

TABLE 1

Treatment of Asthma Mouse Model using Compounds of the Invention

| Compound | Concentration (mg/ml) | Lung resistance (cm H$_2$O/ml/s) |
| --- | --- | --- |
| ICI-847 | 20 | 7.25 |
| ICI-735 | 20 | 8.5 |
| ICI-685 | 20 | 12 |
| Dexamethasone | 20 | 7.75 |
| *A. fumigatus* insult, no therapeutic compound | 0 | 13.5 |
| No *A. fumigatus* insult | 0 | 3 |

Compounds and Synthesis

Figure 30:
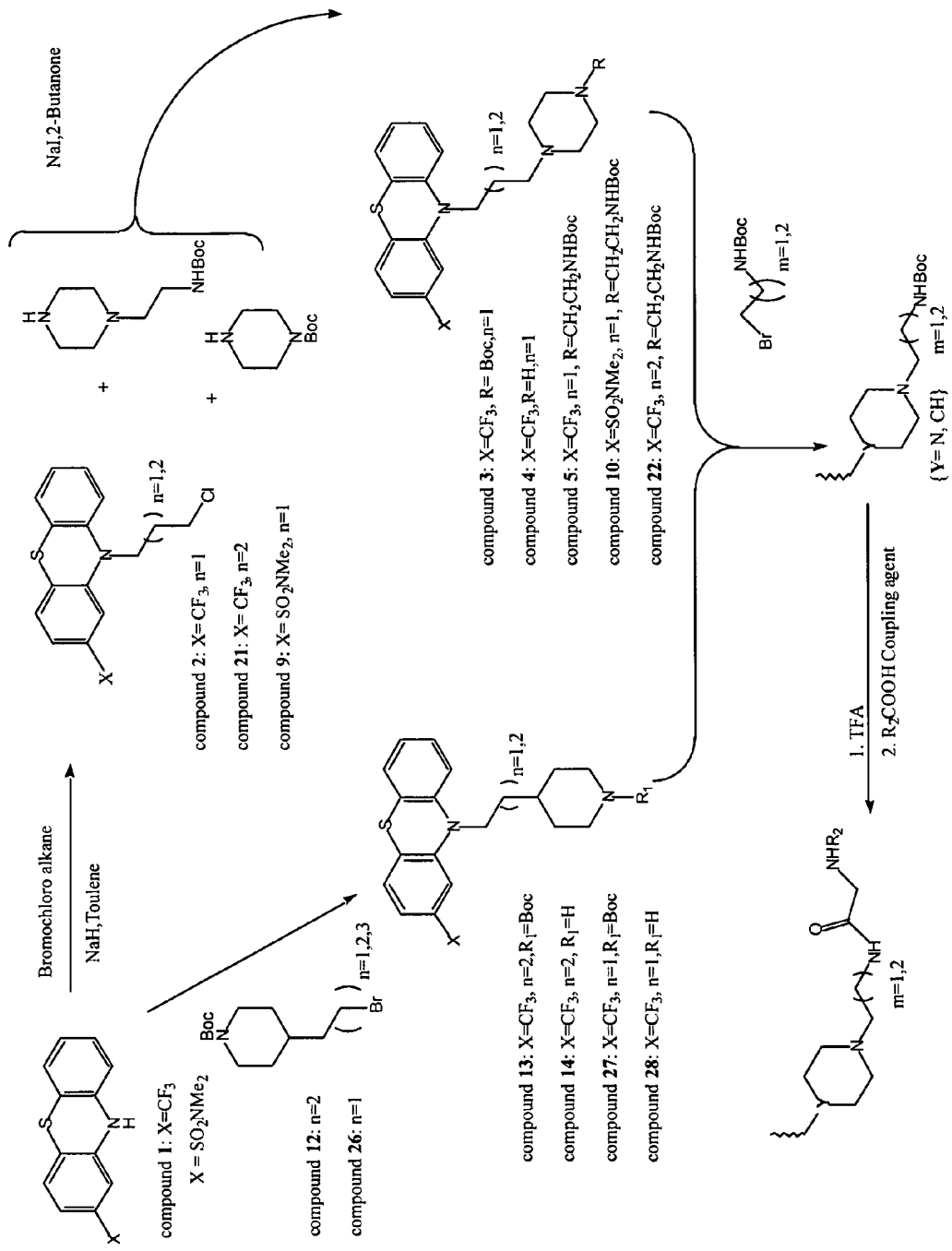
FIG. 30 hela
Figure 31:
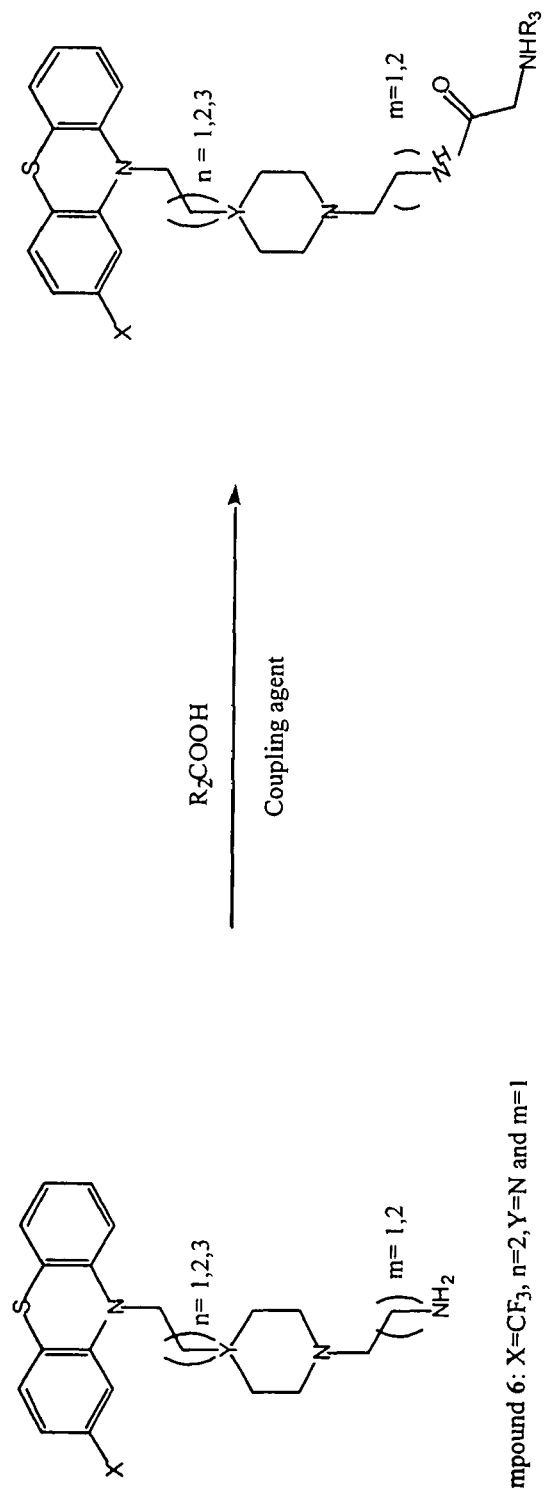
FIG. 31 is a schematic illustrating synthetic schemes for additional number of compounds of the invention.
Figure 32:
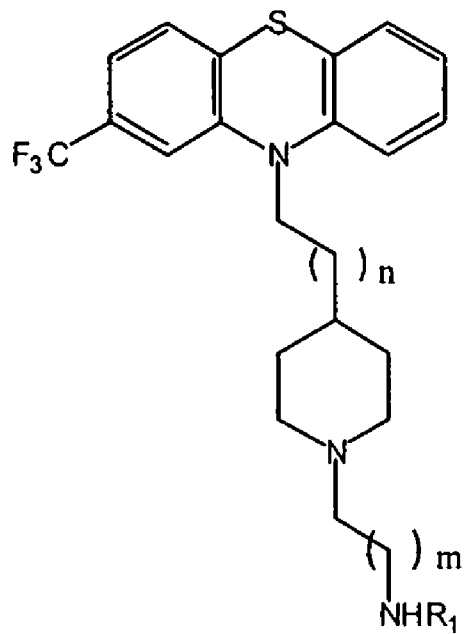
FIG. 32 is a schematic illustrating a number of intermediates for compounds of the invention.
Figure 33:
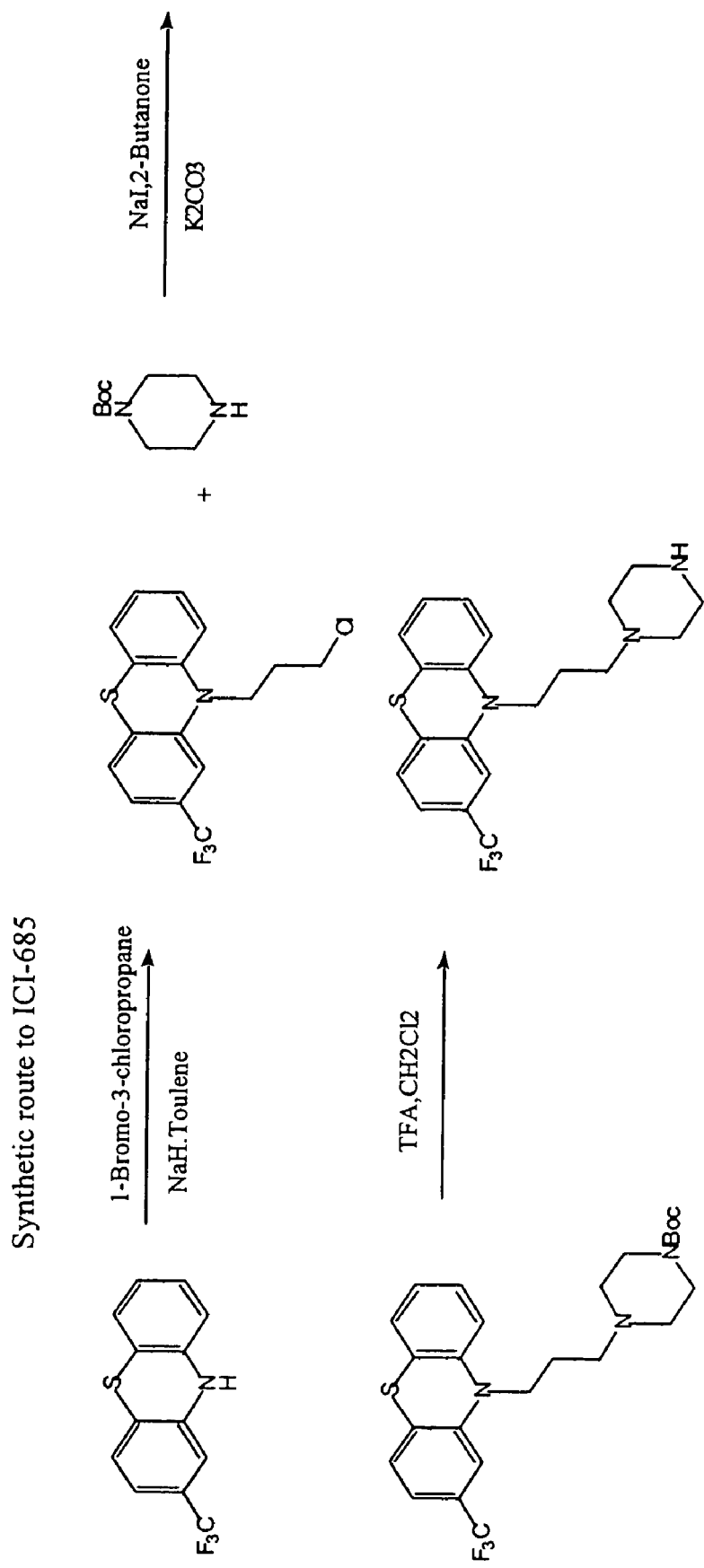
FIG. 33 is a schematic illustrating the synthesis of ICI-685.
Figure 34:
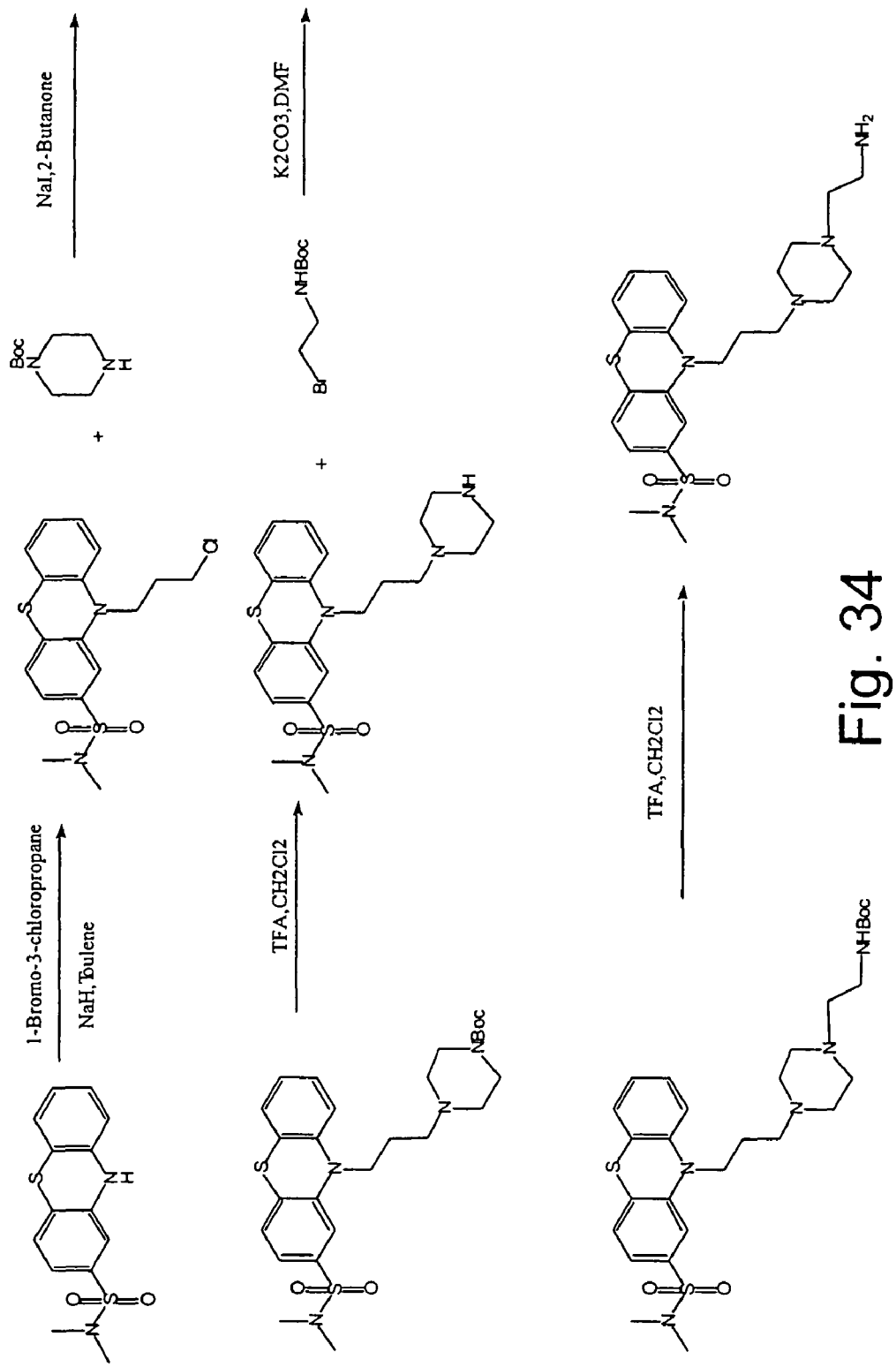
FIG. 34 is a schematic illustrating one synthesis of ICI-715.
Figure 35:
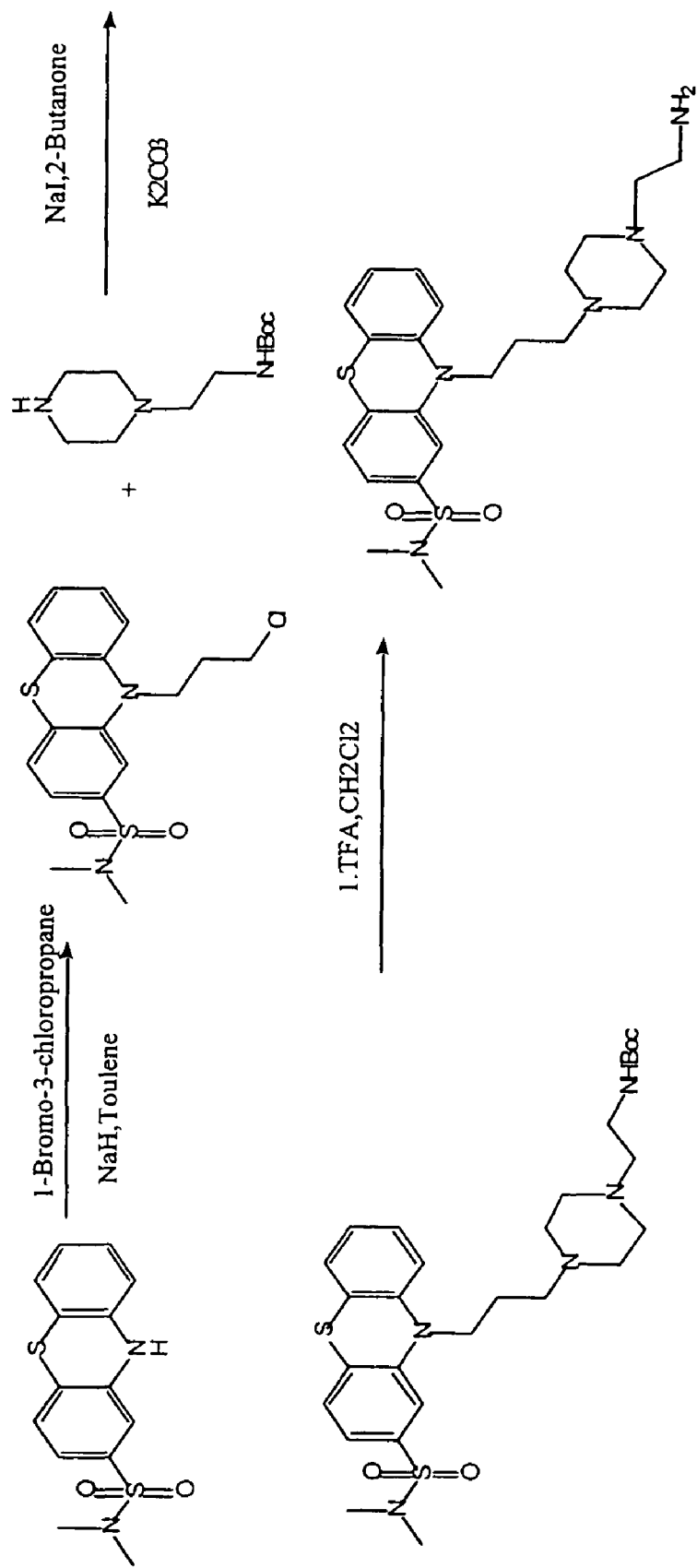
FIG. 35 is a schematic illustrating an alternate synthesis of ICI-715.
Figure 36:
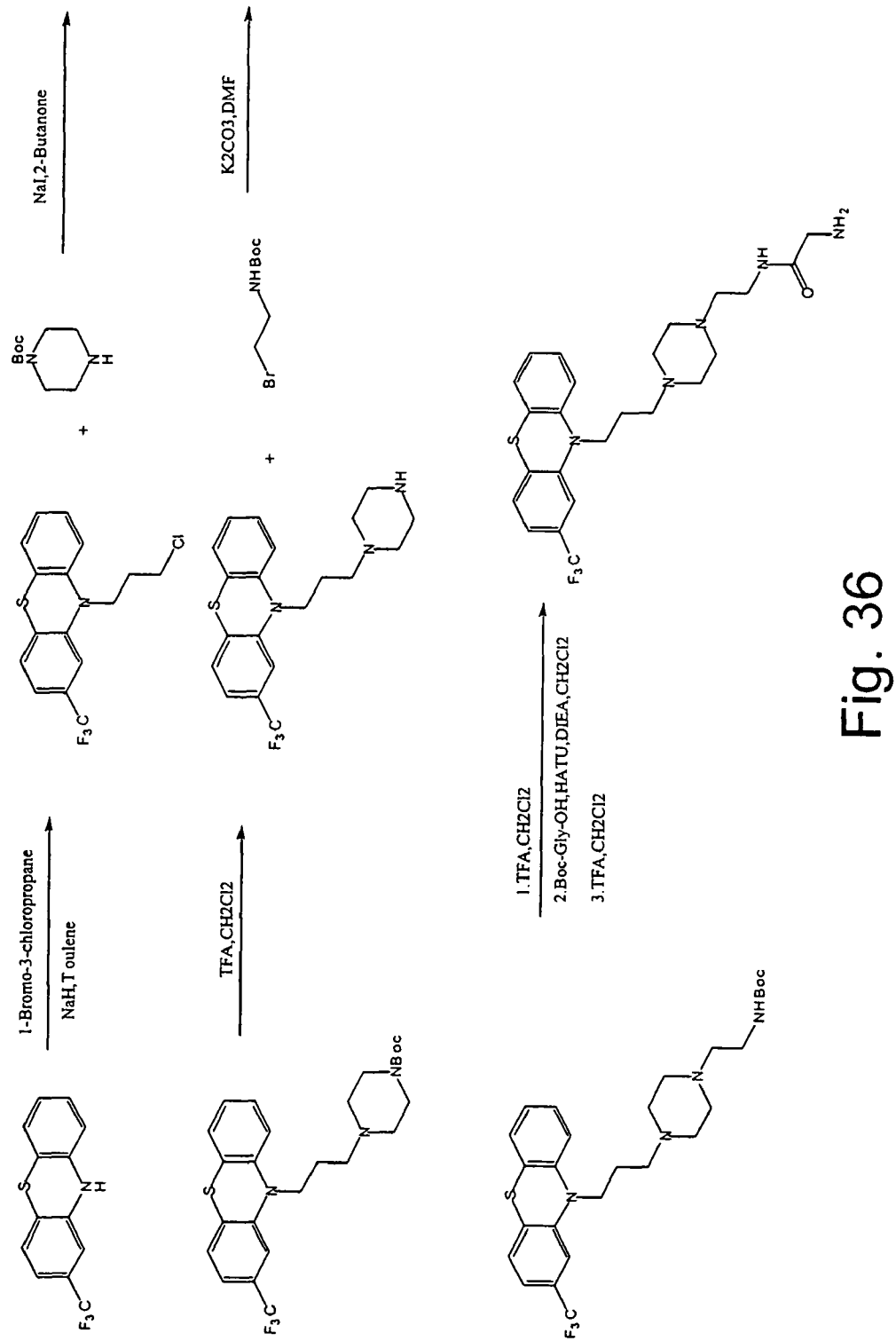
FIG. 36 is a schematic illustrating a synthesis of ICI-735.
Figure 37:
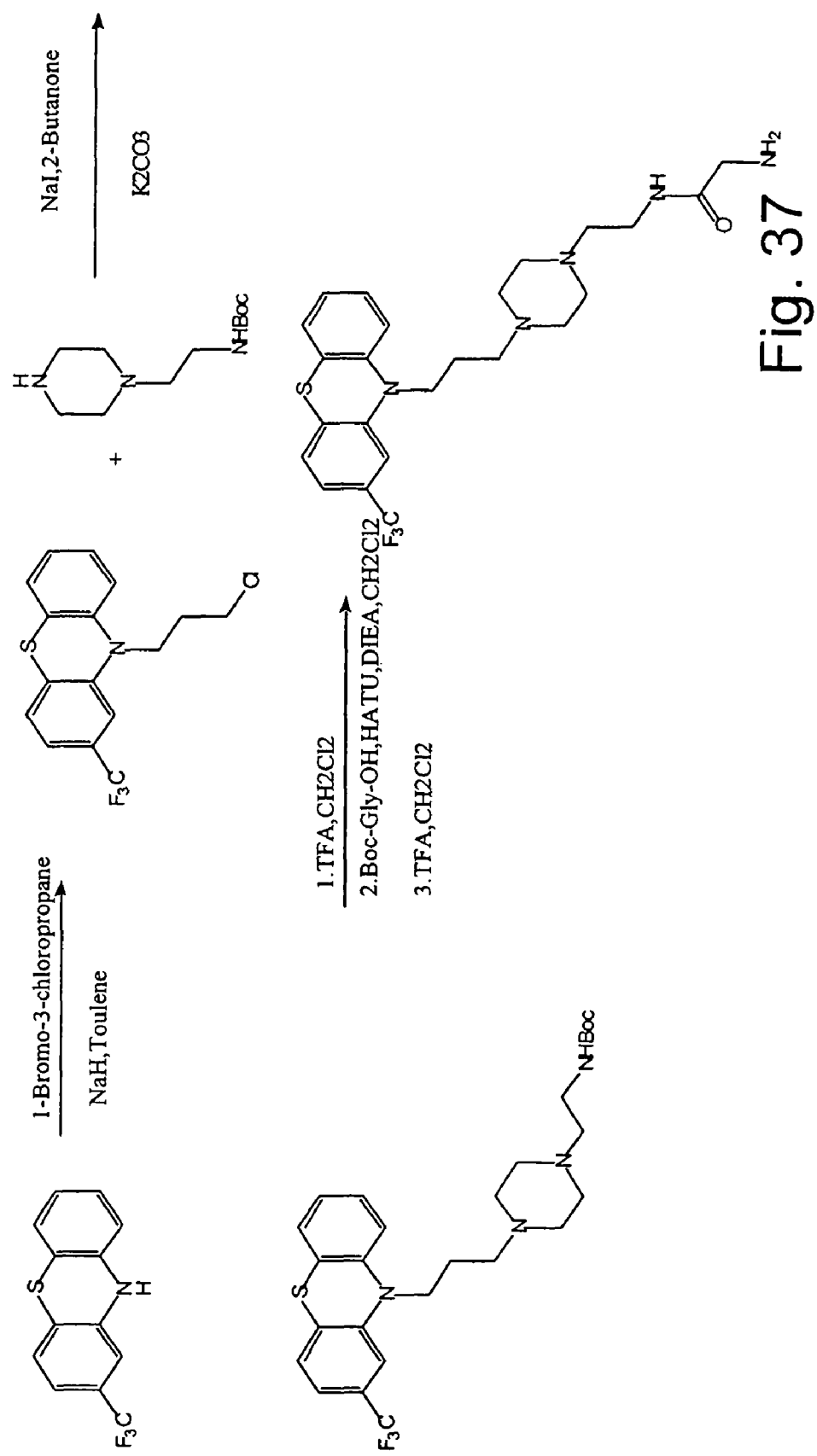
FIG. 37 is a schematic illustrating an alternate synthesis of ICI-735.
Figure 38:
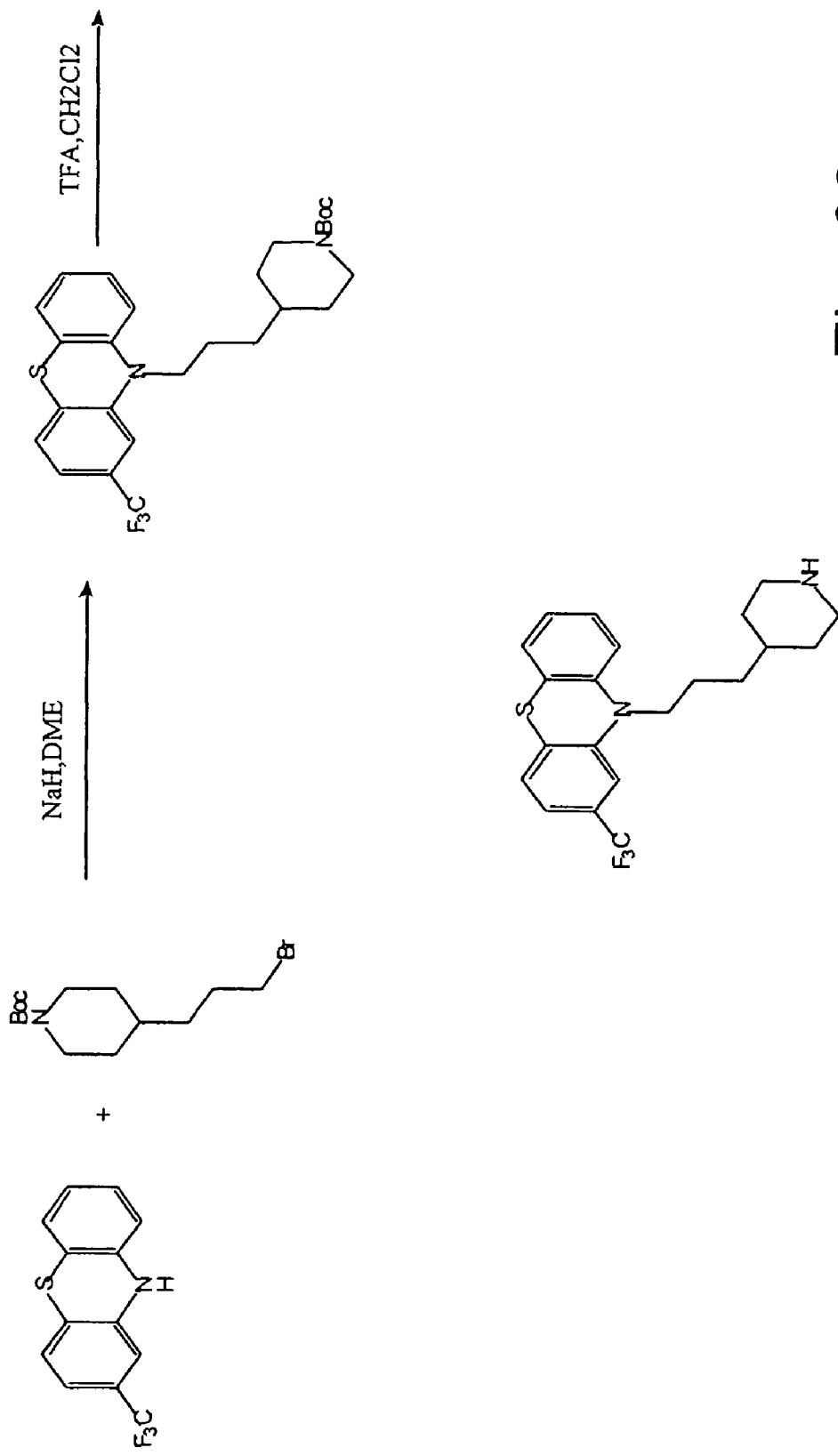
FIG. 38 is a schematic illustrating the synthesis of ICI-824.
Figure 39:
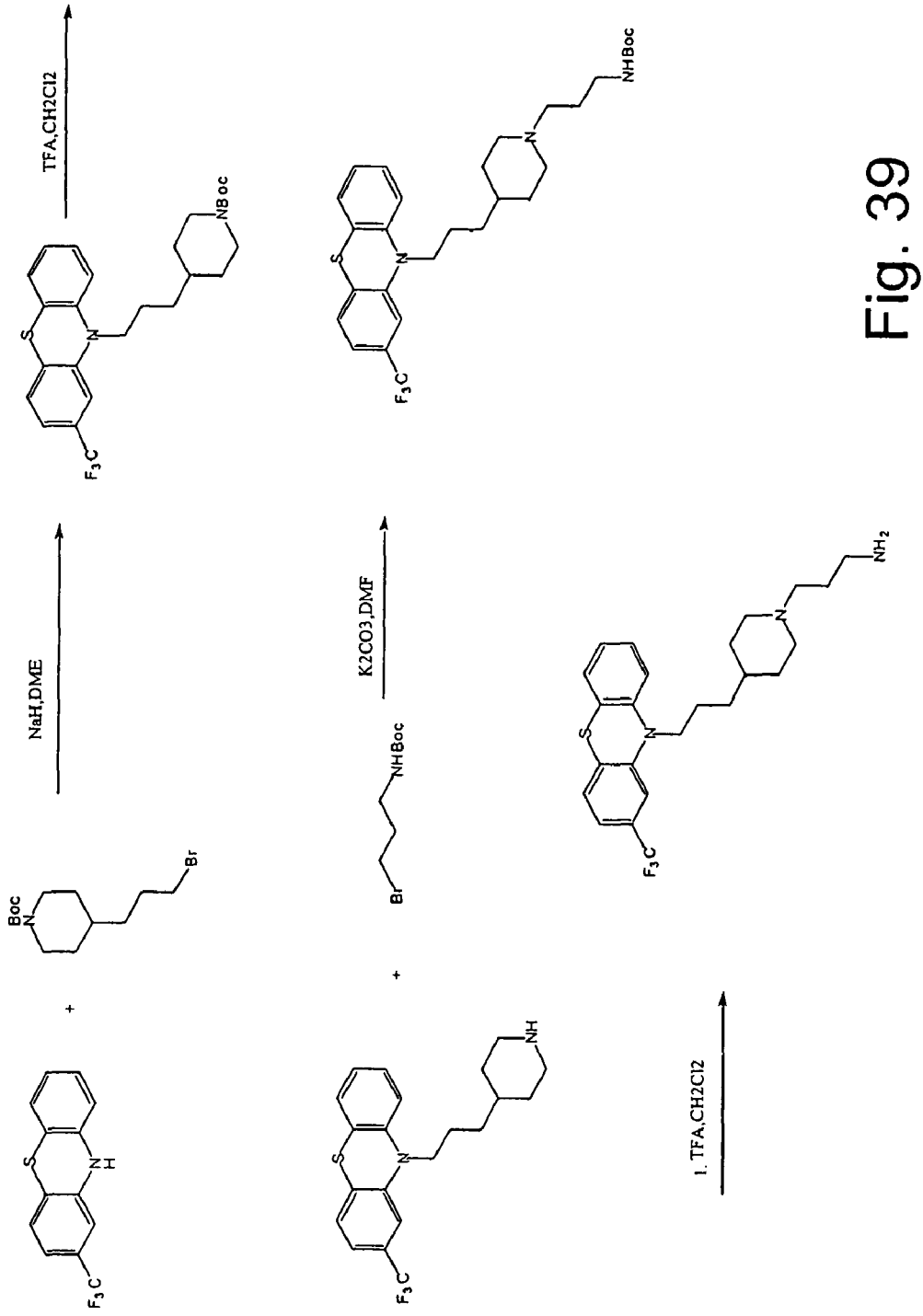
FIG. 39 is a schematic illustrating the synthesis of ICI-847.
Figure 40:
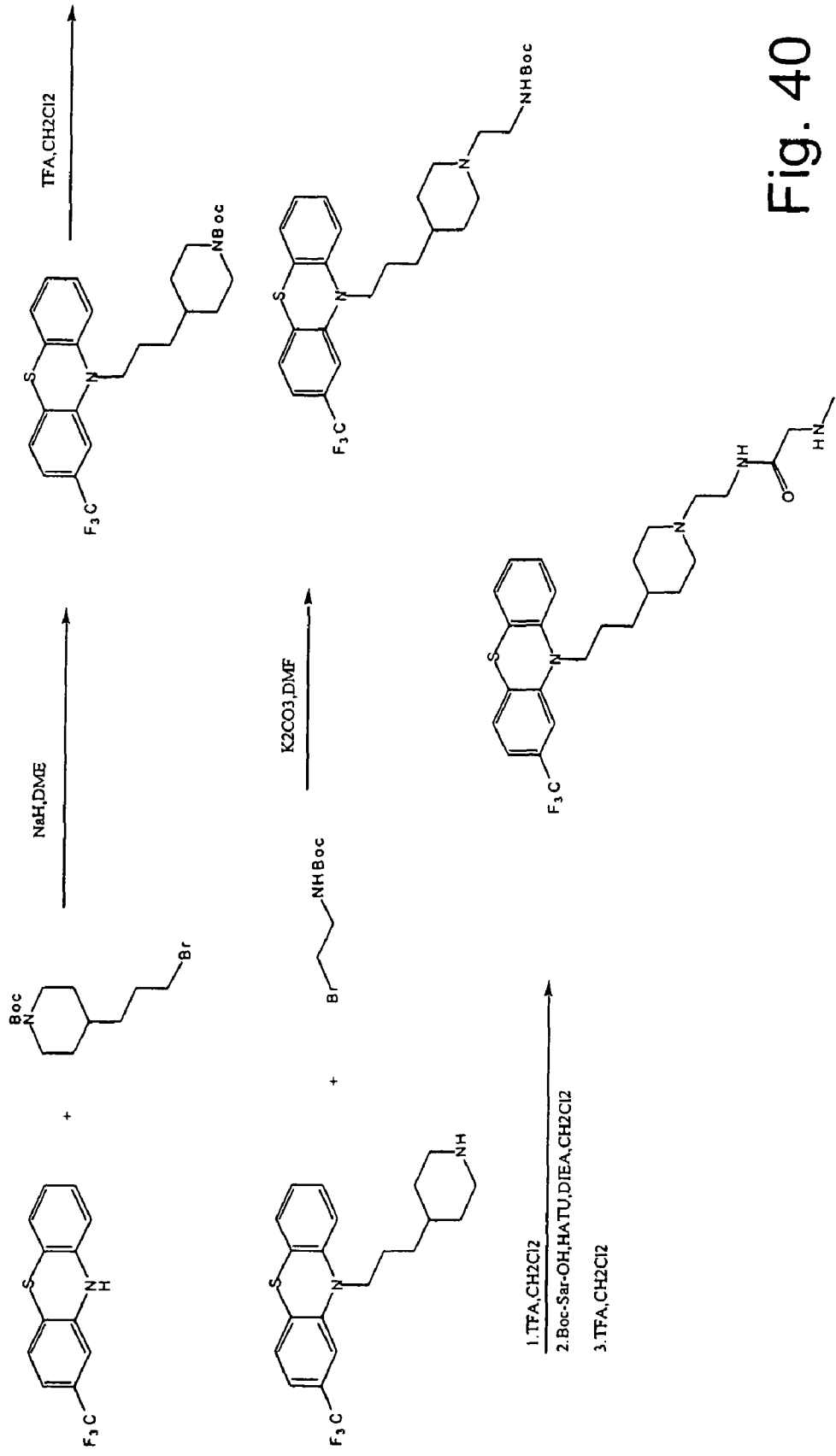
FIG. 40 is a schematic illustrating the synthesis of ICI-849.
Figure 41:
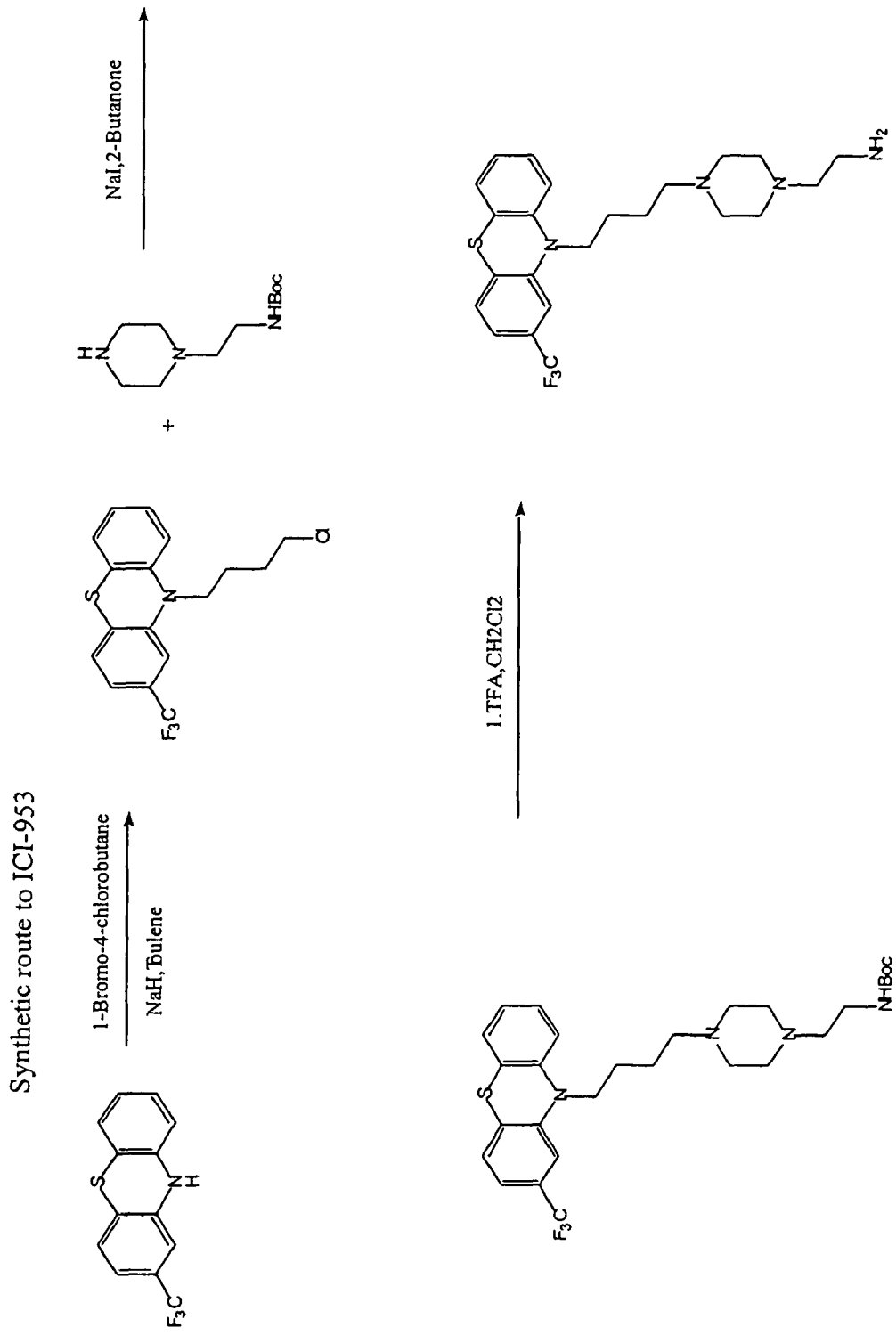
FIG. 41 is a schematic illustrating the synthesis of ICI-953.
Figure 42:
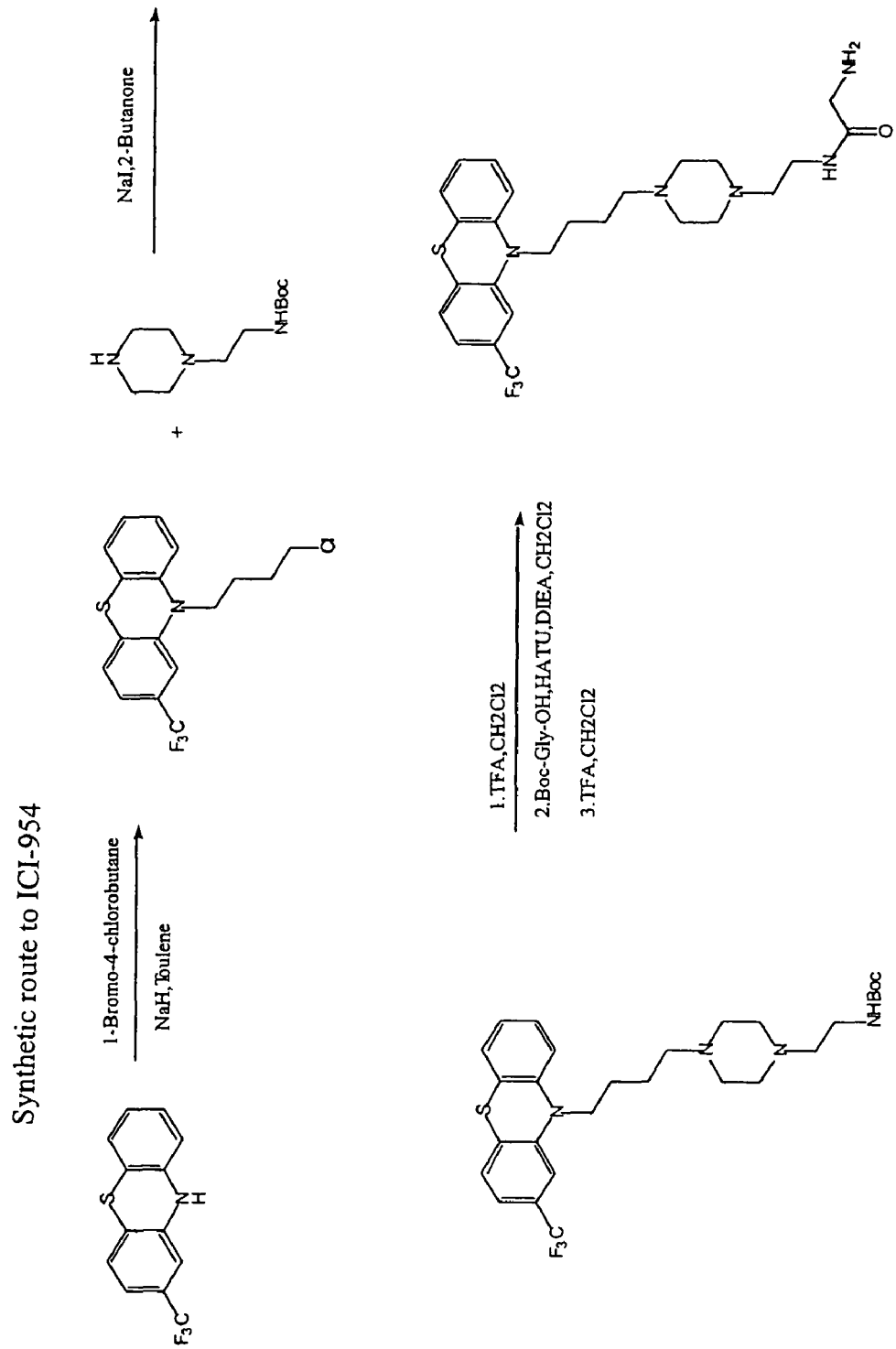
FIG. 42 is a schematic illustrating the synthesis of ICI-954.
Figure 43:
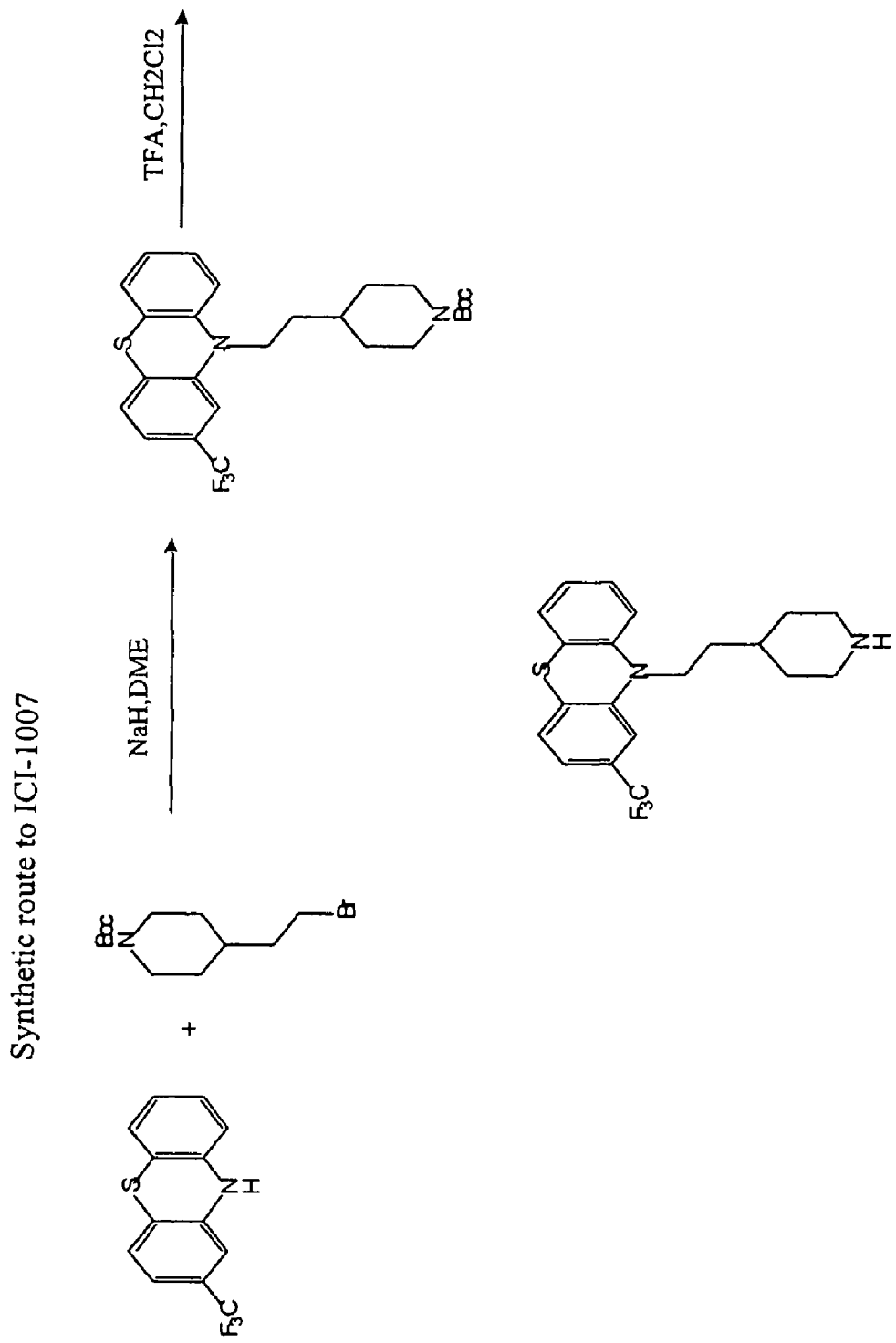
FIG. 43 is a schematic illustrating the synthesis of ICI-1007.
Figure 44:
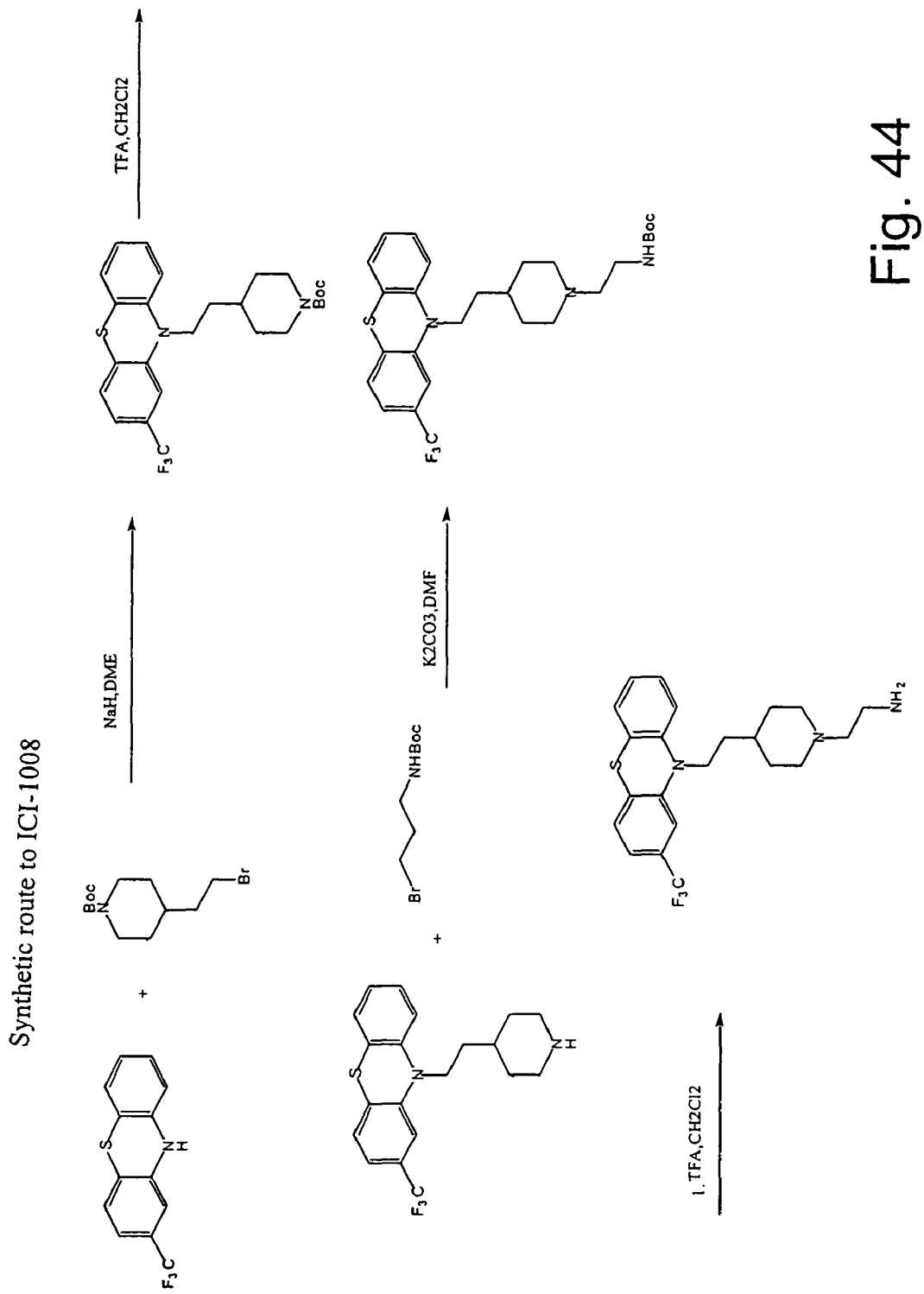
FIG. 44 is a schematic illustrating the synthesis of ICI-1008.

Following is a synthesis of a number of compounds according to the invention, some of which compounds are set forth in the synthetic schematics illustrated in FIGS. 30-32. Furthermore, each of FIGS. 33-44 provides a detailed synthetic pathway for a subset of compounds of the invention.

Compound 2

10-(3-Chloropropyl)-2-trifluoromethylphenothiazine

To a stirred solution of 2-trifluoromethyl phenothiazine (compound 1) (2 g, 7.49 mmol) and sodium hydride (0.5 g, 10.42 mmol) in dry toluene (30 mL) was added 1-bromo-3-chloropropane (1.57 g, 10 mmol). The reaction mixture was stirred for 18 hours at 110° C. under an atmosphere of argon. The solution was cooled to room temperature and poured into an ice-water mixture, the crude product was extracted with ethyl acetate (3×50 mL) and the combined organic phase dried over anhydrous sodium sulphate. Final purification was performed by column chromatography (9:1 hexane:ethyl acetate) on silica gel to give 10-(3-chloropropyl)-2-trifluoromethylphenothiazine (1.5 g, 58%) as a solid.

Compound 3

10-[3-(4-N-Boc-1-piperazinyl)propyl)]-2-trifluoromethylphenothiazine

To a stirred solution of chloro compound 2 (2.57 g, 7.5 mmol) and 1-Boc-piperazine (1.4 g, 7.5 mmol) in methyl ethyl ketone (40 mL) was added sodium iodide (1.5 g, 10 mmol). The reaction mixture was stirred for 24 h at reflux under an atmosphere of argon. The reaction mixture was filtered and the filtrate concentrated under vacuum. The residue was partitioned between ethyl acetate (100 mL) and brine (50 mL). The organic layer was dried over anhydrous sodium sulphate, filtered and evaporated. The resulting residue was purified by silica gel column chromatography (9:1 $CH_2Cl_2$:MeOH) to give 3 (2.7 g, 73%) as a solid. MS (ESI): m/z 494 (M+H).

Compound 4

ICI-685

Compound 3 (750 mg, 1.52 mmol) was dissolved in dry $CH_2Cl_2$ (10 mL) and TFA (0.75 mL, 6.57 mmol) was added dropwise to this solution at 0° C. The solution was stirred at room temperature overnight. The reaction mixture was evaporated and the residue was purified by reversed phase HPLC on a C18 column (acetonitrile:water:TFA, gradient elution) to give the desired product (650 mg, 69%) as a white solid after lyophilization. MS (ESI): m/z 394 (M+H).

Compound 5

10-{3-[4-(N-Boc-2-amino)ethylpiperazinyl]propyl}-2-trifluoromethylphenothiazine

To a stirred suspension of the chloropropyl derivative 2 (1.2 g, 3.5 mmol), potassium carbonate (1.5 g, 10.86 mmol), 1-(2-N-Boc-aminoethyl)piperazine (0.78 g, 3.5 mmol) in methyl ethyl ketone (30 mL), was added sodium Iodide (0.9 g, 6 mmol). The reaction mixture was stirred for 24 h at reflux under an atmosphere of argon. The reaction mixture was filtered, and filtrate was concentrated under vacuum. The residue was partitioned between ethyl acetate (30 mL) and brine (15 mL). The organic layer was dried over anhydrous sodium sulphate, filtered and evaporated. The resulting residue was purified by silica gel chromatography (9:1 $CH_2Cl_2$:MeOH) to give 5 (1.2 g, 64%) as a foam. MS (ESI): m/z 537 (M+H).

Compound 6

10-{3-[4-(2-Amino)ethylpiperazinyl]propyl}2-trifluoromethylphenothiazine

Compound 5 (1.20 g, 2.23 mmol) was dissolved in dry $CH_2Cl_2$ (15 mL) and TFA (1.2 mL, 10.5 mmol) was added dropwise to this solution at 0° C. The solution was stirred at room temperature overnight. The reaction mixture was diluted with $CH_2Cl_2$ and pH adjusted to 8 by addition of saturated aqueous sodium bicarbonate. The layers were separated, and the aqueous layer was extracted with $CH_2Cl_2$ (2×20 mL). The combined organic layers were washed with saturated sodium chloride solution (10 mL), dried over anhydrous sodium sulphate and evaporated. The resulting residue 6, was taken on without any further purification. MS (ESI): m/z 437 (M+H).

Compound 7

N-Boc protected ICI-735

To a solution of N-Boc glycine (0.48 g, 2.75 mmol), HATU (1.1 g, 2.89 mmol) and the phenothiazine piperazine 6 (11.0 g, 2.29 mmol) in $CH_2Cl_2$ (15 mL) was added DIPEA (1 mL) and the mixture was stirred at room temperature for 12 h. The reaction mixture was evaporated and the residue was purified by a silica gel column chromatography (9:1 $CH_2Cl_2$:MeOH) to give amide 7 (0.75 g, 55%) as a foam. MS (ESI): m/z 594 (M+H).

Compound 8

ICI-735

Compound 7 (640 mg, 1.07 mmol) was dissolved in dry $CH_2Cl_2$ (10 mL) and TFA (0.6 mL, 5.26 mmol) was added dropwise to this solution at 0° C. The solution was stirred at room temperature overnight. The reaction mixture was evaporated and residue was purified by reverse phase HPLC on a C18 column (acetonitrile:water:TFA, gradient elution) to give the desired product 8 (620 mg 70%) as a white solid after lyophilization. MS (ESI): m/z 494 (M+H).

Compound 9

10-(3-Chloropropyl)-2-dimethylsulfamidophenothiazine

To a stirred solution of 2-dimethylaminosulfonyl phenothiazine (3.06 g, 10 mmol) and sodium hydride (0.6 g, 12 mmol) in dry toluene (35 mL) was added 1-bromo-3-chloropropane (1.8 g, 1.15 mmol). The reaction mixture was stirred for 12 h at 110° C. under an atmosphere of argon. The solution was cooled to room temperature and poured into an ice-water mixture, the crude product was extracted with ethyl acetate (2×25 mL) and the organic phase was dried over anhydrous sodium sulphate. Final purification was performed by column chromatography (7:3 hexane:ethyl acetate) on silica gel to give 9 (2.5 g, 65%) as an oil.

Compound 10

10-{3-[4-(N-Boc-2-amino)ethylpiperazinyl]propyl}-2-dimethylsulfamidolphenothiazine To a stirred solution of the phenothiazine chloro derivative 9 (382 mg, 1.0 mmol), potassium carbonate (500 mg, 3.62 mmol), and 1-(2-N-Boc-aminoethyl)piperazine (229 mg, 1.0 mmol) in methyl ethyl ketone (20 mL) was added sodium iodide (150 mg, 1 mmol). The reaction mixture was stirred for 24 h at reflux under an atmosphere of argon. The reaction mixture was filtered, and the filtrate was concentrated under vacuum. The residue was partitioned between ethyl acetate (20 mL) and brine (10 mL). The organic layer was dried over anhydrous sodium sulphate, filtered, and evaporated. The resulting residue was purified by silica gel chromatography (9:1 $CH_2Cl_2$:MeOH) to give 10 (410 mg, 71%) as a foam. MS (ESI): m/z 576 (M+H).

Compound 11

ICI-715

Compound 10 (410 mg, 0.71 mmol) was dissolved in dry $CH_2Cl_2$ (5 mL) and TFA (0.4 mL, 3.5 mmol) was added dropwise to this solution at 0° C. The solution was stirred at room temperature overnight. The reaction mixture was evaporated and residue was purified by reversed phase HPLC on a C18 column (acetonitrile:water:TFA, gradient elution) to give the desired product 11 (325 mg, 56%) as a white solid after lyophilization. MS (ESI): m/z 476 (M+H).

Compound 12

N-Boc-4-(3-bromopropyl)piperidine

N-Boc-4-(3-hydroxypropyl)piperidine (160 mg, 0.658 mmol) was dissolved in dry THF (5 mL), and carbon tetrabromide (265 mg, 0.79 mmol) was added. Then a solution of triphenylphosphine (207 mg, 0.79 mmol) in dry tetrahydrofuran (2 mL) was added dropwise over 2 h. The mixture was stirred at room temperature for 18 h, and then diluted with diethyl ether (5 mL). The reaction mixture was filtered, the filtrate concentrated under vacuum, and the resulting residue was purified by silica gel column chromatography (9:1 hexane:ethyl acetate) to give 12 (143 mg, 72%) as an oil.

Compound 13

10-[3-(N-Boc-4-piperidyl)propyl]-2-trifluoromethylphenothiazine

To a stirred solution of 2-trifluoromethylphenothizine 1 (400 mg, 1.5 mmol), sodium hydride (100 mg, 2 mmol) in DME (10 mL) at 90° C. was added N-Boc-4-(3-bromopropyl) piperidine 12 (380 mg, 1.24 mmol) dropwise under an atmosphere of argon. The reaction mixture was stirred for 12 h at reflux. The reaction mixture was filtered and the filtrate was concentrated under vacuum. The residue was partitioned between ethyl acetate (25 mL) and brine (10 mL). The organic layer was dried over anhydrous sodium sulphate, filtered, and evaporated. The resulting residue was purified by silica gel column chromatography (8:2 hexane:ethyl acetate) on silica gel to give phenothiazine derivative 13 (425 mg, 70%) as a solid. MS (ESI): m/z 493 (M+H).

Compound 14

ICI-824

Compound 13 (200 mg, 0.4 mmol) was dissolved in dry $CH_2Cl_2$ (5 mL) and TFA (0.2 mL, 1.75 mmol) was added dropwise to this solution at 0° C. The solution was stirred at room temperature overnight. The reaction mixture was evaporated and residue was purified by reversed phase HPLC on a C18 column (acetonitrile:water:TFA, gradient elution) to give the desired product 14 (125 mg, 61%) as a white solid after lyophilization. MS (ESI): m/z 393 (M+H).

Compound 15

10-{3-[1-(N-boc-2-amino)ethyl-4-piperidyl]propyl}-2-trifluoromethylphenothiazine To a solution of piperidine derivative 14 (160 mg, 0.4 mmol) and potassium carbonate (500 mg, 3.62 mmol) in dry DMF (5 mL) was added N-Boc-2-aminoethylbromide (137 mg, 0.6 mmol), and the solution was stirred for 24 h at room temperature. The mixture was diluted with ethyl ether (20 mL), washed with water (2×10 mL), and brine (5 mL), dried over anhydrous sodium sulphate, and then concentrated under vacuum. The residue was purified by silica gel column chromatography (9:1 $CH_2Cl_2$:MeOH) to give 15 (152 mg, 70%) as an oil. MS (ESI): m/z 536 (M+H).

Compound 16

10-{3-[1-(N-Boc-3-amino)propyl-4-piperidyl]propyl}-2-trifluoromethylphenothiazine To a solution of piperidine derivative 14 (526 mg, 1.34 mmol) and potassium carbonate (1.0 g, 7.25 mmol) in dry DMF (5 mL) was added N-Boc-3-aminopropylbromide (627 mg, 2.63 mmol) and the solution was stirred for 24 h at room temperature. The mixture was diluted with diethyl ether (10 mL), washed with water (2×10 mL), and brine (5 mL), dried over anhydrous sodium sulphate, and then concentrated under vacuum. The residue was purified by silica gel column chromatography (9:1 $CH_2Cl_2$:MeOH) to give 16 (325 mg, 44%) as an oil. MS (ESI): m/z 550 (M+H).

Compound 17

ICI-847

Compound 16 (120 mg, 0.22 mmol) was dissolved in dry $CH_2Cl_2$ (5 mL) and TFA (0.2 mL, 1.75 mmol) was added dropwise to this solution at 0° C. The solution was stirred at room temperature overnight. The reaction mixture was evaporated and residue was purified by reversed phase HPLC on a C18 column (acetonitrile:water:TFA, gradient elution) to give the desired product 17 (52 mg, 35%) as a white solid after lyophilization. MS (ESI): m/z 450 (M+H).

Compound 18

10-{3-[1-(2-Amino)ethyl-4-piperidyl]propyl}-2-trifluoromethylphenothiazine

Compound 15 (600 mg, 1.12 mmol) was dissolved in dry $CH_2Cl_2$ (10 mL) and TFA (0.75 mL, 6.57 mmol) was added dropwise to this solution at 0 C. The solution was stirred at room temperature overnight. The reaction mixture was diluted with $CH_2Cl_2$ and pH adjusted to 8 by addition of saturated aqueous sodium bicarbonate. The layers were separated, and aqueous layer was extracted with $CH_2Cl_2$ (2×20 mL). The combined organic layers were washed with saturated sodium chloride solution (10 mL), dried over anhydrous sodium sulphate and evaporated. The resulting amine 18, was taken on without any further purification. MS (ESI): m/z 436 (M+H).

Compound 19

N-Boc protected ICI-849

To a solution of N-Boc sarcosine (286 mg, 1.51 mmol), HATU (574 mg, 1.51 mmol) and the propyl ethylpiperidine amine 18 (550 mg, 1.26 mmol) in CH$_2$Cl$_2$ (15 mL) was added DIPEA (0.5 mL) and the mixture was stirred at room temperature for 12 h. The reaction mixture was evaporated and residue was purified by a silica gel column chromatography (9:1 CH$_2$Cl$_2$:MeOH) to give amide 19 (400 mg, 52%) as a foam. MS (ESI): m/z 607(M+H).

Compound 20

ICI-849

Compound 19 (200 mg, 0.33 mmol) was dissolved in dry CH$_2$Cl$_2$ (5 mL) and TFA (0.2 mL, 1.75 mmol) was added dropwise to this solution at 0 C. The solution was stirred at room temperature overnight. The reaction mixture was evaporated and residue was purified by reversed phase HPLC on a C18 column (acetonitrile:water:TFA, gradient elution) to give the desired product 20 (110 mg, 45%) as a white solid after lyophilization. MS (ESI): m/z 507 (M+H).

Compound 21

10-(4-chlorobutyl)-2-trifluoromethylphenothiazine

To a stirred solution of 2-trifluoromethylphenothiazine 1 (4.0 g, 15 mmol), sodium hydride (1.2 g, 24 mmol) in dry toluene (40 mL), 1-bromo 4-chlorobutane (3.0 g, 17.6 mmol) was added. The reaction mixture was stirred for 18 hours at 110° C. under an atmosphere of argon. The solution was cooled to room temperature and poured into an ice-water mixture. The crude product was extracted with ethyl acetate (3×50 mL) and the organic phase was dried over sodium sulphate. Final purification was performed by column chromatography (9:1 hexane:ethyl acetate) on silica gel to give 21 (3.5 g, 65%) as an oil.

Compound 22

10-{4-[4-(N-Boc-2-amino)ethylpiperazinyl]butyl}-2-trifluoromethylphenothiazine

To a stirred suspension of the chlorobutyl derivative 21 (3.57 g, 10 mmol), potassium carbonate (4.0 g, 28.98 mmol), 1-(2-N-Boc-aminoethyl)piperazine (2.6 g, 11.35 mmol) in methyl ethyl ketone (40 mL) was added sodium Iodide 2.5 g, 16 mmol). The reaction mixture was stirred for 24 h at reflux under an atmosphere of argon. The reaction mixture was filtered, and the filtrate was concentrated under vacuum. The residue was partitioned between ethyl acetate (50 mL) and brine (25 mL). The organic layer was dried over anhydrous sodium sulphate, filtered and evaporated. The resulting residue was purified by silica gel chromatography (9:1 CH$_2$Cl$_2$:MeOH) to give 22 (4.0 g, 72%) as a foam. MS (ESI): m/z 551 (M+H).

Compound 23

ICI-953

Compound 22 (152 mg, 0.28 mmol) was dissolved in dry CH$_2$Cl$_2$ (5 mL) and TFA (0.2 mL, 1.75 mmol) was added dropwise to this solution at 0° C. The solution was stirred at room temperature overnight. The reaction mixture was evaporated and residue was purified by reversed phase HPLC on a C18 column (acetonitrile:water:TFA, gradient elution) to give the desired product 23 (150 mg, 68%) as a white solid after lyophilization. MS (ESI): m/z 451 (M+H).

Compound 24

N-Boc protected ICI-954

To a solution of N-Boc-glycine (0.7 g, 4.0 mmol), HATU (1.6 g, 4.2 mmol) and amine 23 (1.5 g, 3.3 mmol) in CH$_2$Cl$_2$ (20 mL) was added DIPEA (1.5 mL) and the mixture was stirred at room temperature for 12 h. The reaction mixture was evaporated and residue was purified by a silica gel column chromatography (9:1 CH$_2$Cl$_2$:MeOH) to give amide 24 (1.2 g, 60%) as a foam.

Compound 25

ICI-954

Compound 24 (250 mg, 0.41 mmol) was dissolved in dry CH$_2$Cl$_2$ (5 mL) and TFA (0.2 mL, 1.75 mmol) was added dropwise to this solution at 0° C. The solution was stirred at room temperature overnight. The reaction mixture was evaporated and residue was purified by reversed phase HPLC on a C18 column (acetonitrile:water:TFA, gradient elution) to give the desired product 25 (210 mg, 60%) as a white solid after lyophilization. MS (ESI): m/z 508 (M+H).

Compound 26

N-Boc-4-(2-bromoethyl)piperidine

N-Boc-4-(2-hydroxyethyl)piperidine (0 95 g, 4.17 mmol) was dissolved in dry THF (20 mL), and carbon tetrabromide (1.34 g, 4.0 mmol) was added. Then a solution of triphenylphosphine (1.15 g, 4.38 mmol) in dry tetrahydrofuran (2 mL) was added dropwise over 2 h. The mixture was stirred at room temperature for 18 h, and then diethyl ether (50 mL) added to the mixture. The reaction mixture was filtered, and filtrate concentrated under vacuum. The resulting residue was purified by silica gel column chromatography (9:1 hexane: ethyl acetate) to give 26 (1.05 g, 86%) as an oil.

Compound 27

10-[2-(N-Boc-4-piperidyl)ethyl]-2-trifluoromethylphenothiazine

To a stirred solution of 2-trifluoromethylphenothizine 1 (0.91 g, 3.42 mmol), sodium hydride (0.2 g, 4.0 mmol) in DME (20 mL) at 90° C. was added N-Boc-4-(2-bromoethyl) piperidine 26 (1.0 g, 3.42 mmol) dropwise under an atmosphere of argon. The reaction mixture was stirred for 12 h at reflux temperature. The reaction mixture was filtered, and filtrate was concentrated under vacuum. The residue was partitioned between ethyl acetate (25 mL) and brine (10 mL). The organic layer was dried over anhydrous sodium sulphate, filtered, and evaporated. The resulting residue was purified by column chromatography (8:2 n-hexane:ethyl acetate) on silica gel to give phenothiazine derivative 27 (0.3 g, 18%) as a foam. MS (ESI): m/z 479(M+H).

Compound 28

ICI-1007

Compound 27 (70 mg, 0.15 mmol) was dissolved in dry CH$_2$Cl$_2$ (5 mL) and TFA (0.1 mL, 0.88 mmol) was added dropwise to this solution at 0° C. The solution was stirred at room temperature overnight. The reaction mixture was evaporated and residue was purified by reversed phase HPLC on a C18 column (acetonitrile:water:TFA, gradient elution) to give the desired product 28 (50 mg, 69%) as a white solid after lyophilization. MS (ESI): m/z 379 (M+H).

Compound 29

10-{2-[1-(N-Boc-2-amino)ethyl-4-piperidyl]ethyl}-2-trifluoromethylphenothiazine

To a solution of the piperidine derivative 28 (145 mg, 0.38 mmol) and potassium carbonate (500 mg, 3.62 mmol) in dry DMF (5 mL) was added N-Boc-2-aminoethylbromide (102 mg, 0.45 mmol), and the solution was stirred for 24 h at room temperature. The mixture was diluted with diethyl ether (20 mL), washed with a water (2×10 mL), brine (5 mL), dried over anhydrous sodium sulphate, and then concentrated under vacuum. The residue was purified by silica gel column chromatography (9:1 $CH_2Cl_2$:MeOH) to give 29 (145 mg, 73%) as an oil. MS (ESI): m/z 522 (M+H).

Compound 30

ICI-1008

Compound 29 (100 mg, 0.19 mmol) was dissolved in dry $CH_2Cl_2$ (5 mL) and TFA (0.2 mL, 1.75 mmol) was added dropwise to this solution at 0° C. The solution was stirred at room temperature overnight. The reaction mixture was evaporated and residue was purified by reversed phase HPLC on a C18 column (acetonitrile:water:TFA, gradient elution) to give the desired product 30 (52 mg, 42%) as a white solid after lyophilization. MS (ESI): m/z 422 (M+H).

Additional Biological Assays

Serotonin-receptor Binding Assays

The methods employed in this study have been adapted from the scientific literature to maximize reliability and reproducibility. Reference standards were run as an integral part of each assay to ensure the validity of the results obtained. Assays were performed under conditions as described below. Where presented, $IC_{50}$ values were determined by a non-linear, least squares regression analysis using the DATA ANALYSIS TOOLBOX (MDL Information Systems, San Leandro, Calif., USA). Where inhibition constants ($K_i$) are presented, the $K_i$ values were calculated using the equation of Cheng and Prusoff (Cheng, Y., Prusoff, W. H., Biochem. Pharmacol. 22:3099-3108, 1973) using the observed $IC_{50}$ of the tested compound, the concentration of radioligand employed in the assay, and historical values for the $K_D$ of the ligand. Where presented, the Hill coefficient ($n_H$), defining the slope of the competitive binding curve, was calculated using the DATA ANALYSIS TOOLBOX. Hill coefficients that differ by more than 10 may suggest that the binding displacement does not follow the laws of mass action with a single binding site.

Tables 4-7 illustrate the results for the biochemical assays set forth in Tables 2 and 3. The experiments measure the ability of compounds of the invention to displace known ligands from serotonin receptors. The data for 5-HTR-1A and 5-HTR-1B, set forth in Tables 4-7, demonstrate effectiveness of compounds of the invention in specific displacement of ligands.

TABLE 2

Experimental data for experiments 271000 (Table 4) and 271110 (Table 5)

| | 271000 Serotonin (5-Hydroxytryptamine) 5-$HT_1$, Non-Selective | | 271000 Serotonin (5-Hydroxytryptamine) 5-$HT_{1A}$ |
|---|---|---|---|
| Source: | Wistar Rat cerebral cortex | Source: | Human recombinant CHO cells |
| Ligand: | 2 nM [$^3$H] Serotonin (5-HT) | Ligand | 1.5 nM [$^3$H] 8-OH-DPAT |
| Vehicle: | 1% DMSO | Vehicle: | 1% DMSO |
| Incubation Time/Temp: | 10 minutes @ 37° C. | Incubation Time/Temp: | 60 minutes @ 25° C. |
| Incubation Buffer: | 50 mM Tris-HCl, pH 7.4, 0.1% Ascorbic Acid, 10 μM Pargyline, 4 mM $CaCl_2$ | Incubation Buffer: | 50 mM Tris-HCl, pH 7.4, 0.1% Ascorbic Acid, 0.5 mM EDTA, 10 mM $MgSO_4$ |
| Non-Specific Ligand: | 10 μM Serotonin (5-HT) | Non-Specific Ligand: | 10 μM Metergoline |
| $K_D$: | 0.61 nM * | $K_D$: | 2 nM * |
| $B_{MAX}$: | 0.58 pmole/mg Protein * | $B_{MAX}$: | 1.3 pmole/mg Protein * |
| Specific Binding: | 80% * | Specific Binding: | 75%* |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

TABLE 3

Experimental data for experiments 271200 (Table 6) and 271600 (Table 7).

| | 271000 Serotonin (5-Hydroxytryptamine) 5-$HT_{1B}$ | | 271000 Serotonin (5-Hydroxytryptamine) 5-$HT_2$, Non-Selective |
|---|---|---|---|
| Source: | Wistar Rat cerebral cortex | Source: | Wistar Rat brain |
| Ligand: | 10 pM [$^{125}$I] Cyanopindolol | Ligand | 0.5 nM [$^3$H] Ketanserin |
| Vehicle: | 1% DMSO | Vehicle: | 1% DMSO |
| Incubation Time/Temp: | 90 minutes @ 37° C. | Incubation Time/Temp: | 40 minutes @ 25° C. |

TABLE 3-continued

Experimental data for experiments 271200 (Table 6) and 271600 (Table 7).

| 271000 Serotonin (5-Hydroxytryptamine) 5-HT$_{1B}$ | | 271000 Serotonin (5-Hydroxytryptamine) 5-HT$_2$, Non-Selective | |
|---|---|---|---|
| Incubation Buffer: | 50 mM Tris-HCl, pH 7.4, 154 mM NaCl, 10 μM Pargyline, 30 μM Isoprenaline | Incubation Buffer: | 50 mM Tris-HCl, pH 7.4 |
| Non-Specific Ligand: | 10 μM Serotonin (5-HT) | Non-Specific Ligand: | 1 μM Ketanserin |
| K$_D$: | 0.19 nM * | K$_D$: | 0.82 nM* |
| B$_{MAX}$: | 0.14 pmole/mg Protein * | B$_{MAX}$: | 0.52 pmole/mg Protein * |
| Specific Binding: | 70% * | Specific Binding: | 92% * |
| Quantitation Method: | Radioligand Binding | Quantitation Method: | Radioligand Binding |
| Significance Criteria: | ≧50% of max stimulation or inhibition | Significance Criteria: | ≧50% of max stimulation or inhibition |

TABLE 4

Assay 271000 - Serotonin (5-Hydroxytryptamine) 5-HT$_1$, Non Selective

| COMPOUND CODE | CONC. | % INHIBITION |
|---|---|---|
| ICI-685 | 10 μM | 32 |
|  | 0.1 μM | -3 |
| ICI-715 | 10 μM | 62 |
|  | 0.1 μM | 15 |
| ICI-735 | 10 μM | 63 |
|  | 0.1 μM | 16 |
| ICI-824 | 10 μM | 11 |
|  | 0.1 μM | -14 |
| ICI-847 | 10 μM | -7 |
|  | 0.1 μM | -11 |
| ICI-849 | 10 μM | 10 |
|  | 0.1 μM | -2 |
| ICI-953 | 10 μM | -1 |
|  | 0.1 μM | -10 |
| ICI-954 | 10 μM | 18 |
|  | 0.1 μM | -3 |
| ICI-1007 | 10 μM | 24 |
|  | 0.1 μM | -12 |
| ICI-1008 | 10 μM | 3 |
|  | 0.1 μM | -20 |
| ICI-1175 | 10 μM | 69 |
|  | 0.1 μM | 18 |
| ICI-1176 | 10 μM | 75 |
|  | 0.1 μM | 32 |

TABLE 5

Assay 271000 - Serotonin (5-Hydroxytryptamine) 5-HT$_{1A}$

| COMPOUND CODE | CONC. | % INHIBITION |
|---|---|---|
| ICI-685 | 10 μM | 26 |
|  | 0.1 μM | 1 |
| ICI-715 | 10 μM | 87 |
|  | 0.1 μM | 5 |
| ICI-735 | 10 μM | 89 |
|  | 0.1 μM | 14 |
| ICI-824 | 10 μM | 53 |
|  | 0.1 μM | 2 |
| ICI-847 | 10 μM | 74 |
|  | 0.1 μM | -8 |
| ICI-849 | 10 μM | 65 |
|  | 0.1 μM | 18 |
| ICI-953 | 10 μM | 54 |
|  | 0.1 μM | 5 |
| ICI-954 | 10 μM | 56 |
|  | 0.1 μM | 6 |
| ICI-1007 | 10 μM | 48 |
|  | 0.1 μM | 2 |
| ICI-1008 | 10 μM | 69 |
|  | 0.1 μM | 4 |
| ICI-1175 | 10 μM | 89 |
|  | 0.1 μM | 21 |
| ICI-1176 | 10 μM | 93 |
|  | 0.1 μM | 32 |

TABLE 6

Assay 271200 - Serotonin (5-Hydroxytryptamine) 5-HT$_{1B}$

| COMPOUND CODE | CONC. | % INHIBITION |
|---|---|---|
| ICI-685 | 10 μM | 10 |
|  | 0.1 μM | 6 |
| ICI-715 | 10 μM | 90 |
|  | 0.1 μM | 23 |
| ICI-735 | 10 μM | 86 |
|  | 0.1 μM | 13 |
| ICI-824 | 10 μM | 6 |
|  | 0.1 μM | 2 |
| ICI-847 | 10 μM | -33 |
|  | 0.1 μM | -5 |
| ICI-849 | 10 μM | -2 |
|  | 0.1 μM | -7 |
| ICI-953 | 10 μM | 2 |
|  | 0.1 μM | 7 |
| ICI-954 | 10 μM | -1 |
|  | 0.1 μM | 4 |
| ICI-1007 | 10 μM | 48 |
|  | 0.1 μM | 8 |
| ICI-1008 | 10 μM | 0 |
|  | 0.1 μM | -3 |
| ICI-1175 | 10 μM | 29 |
|  | 0.1 μM | 1 |
| ICI-1176 | 10 μM | 103 |
|  | 0.1 μM | 92 |

TABLE 7

Assay 271600 - Serotonin (5-Hydroxytryptamine) 5-HT$_2$, Non-Selective

| COMPOUND CODE | CONC. | % INHIBITION |
|---|---|---|
| ICI-685 | 10 μM | 82 |
|  | 0.1 μM | 31 |

TABLE 7-continued

Assay 271600 - Serotonin (5-Hydroxytryptamine) 5-HT$_2$, Non-Selective

| COMPOUND CODE | CONC. | % INHIBITION |
|---|---|---|
| ICI-715 | 10 μM | 83 |
|  | 0.1 μM | 18 |
| ICI-735 | 10 μM | 91 |
|  | 0.1 μM | 62 |
| ICI-824 | 10 μM | 84 |
|  | 0.1 μM | 28 |
| ICI-847 | 10 μM | 82 |
|  | 0.1 μM | 3 |
| ICI-849 | 10 μM | 85 |
|  | 0.1 μM | 15 |
| ICI-953 | 10 μM | 71 |
|  | 0.1 μM | 16 |
| ICI-954 | 10 μM | 89 |
|  | 0.1 μM | 21 |
| ICI-1007 | 10 μM | 87 |
|  | 0.1 μM | 51 |
| ICI-1008 | 10 μM | 94 |
|  | 0.1 μM | 38 |
| ICI-1175 | 10 μM | 82 |
|  | 0.1 μM | 67 |
| ICI-1176 | 10 μM | 79 |
|  | 0.1 μM | 19 |

Pharmacological Evaluation of Compounds ICI-685 and ICI-735 in Model of LPS-Mediated Cytokine Production.

Bolus injection of lethal or sub-lethal doses of lipopolysaccharide (LPS; the major component of bacterial cell walls) results in a rapid and transient rise in serum cytokine levels (e.g. TNF-α) in mammals. This animal model was originally developed to mirror certain aspects of septic shock in humans; however, there is poor correlation between efficacy in LPS-rodent models and clinical efficacy. However, this model may be an effective first-line general inflammation model and could be useful in determining the anti-inflammatory potential of test compounds. A variety of clinically approved anti-inflammatory compounds, including glucocorticoids, NSAIDS and COX-2 inhibitors are extremely effective in this model. Compounds ICI-685 and ICI-735 were tested for their ability to inhibit LPS-stimulated TNF-α and IL-1β production.

Both ICI-685 and ICI-735 were formulated in water. For the time course study, both drugs were formulated at a concentration of 1 mg/ml and dosed 10 ml/kg to produce a dose of 10 mg/kg. For the dose-response study, drug was formulated at concentrations of 0.05, 0.2 and 0.5 mg/ml and dosed at a volume of 10 ml/kg to produce doses of 0.5, 2 and 5 mg/kg, respectively. Animals were dosed IV or IP.

CD1:ICR mice were obtained from Harlan (Indianapolis, Ind.) at 6 weeks of age. Animals were housed 5 per cage, kept on a 12 hr light dark cycle and fed food and water ad libitum. Animals were tested at 8-10 weeks of age.

Lipopolysaccharide (heat killed E. coli 0127:B5; Sigma Aldrich) was prepared in distilled water at a concentration of 0.025 mg/ml. LPS was dosed at a volume of 10 ml/kg (IP) to produce a final dose of 0.25 mg/kg (approximately 7.5 μg/mouse). Drugs were dosed prior to LPS administration as indicated elsewhere herein. Blood was collected by retro-orbital eye bleed 90 minutes after LPS administration. Serum was prepared from blood and TNF-α and IL-1β levels were measured by using the OPT-EIA mouse TNF-α and IL-1β ELISA kits (BD Biosciences) as per directions of the manufacturer.

The first study was designed to determine the optimal route of administration and the optimal pre-treatment time. Two pre-dose time course studies were conducted. The first (Study 1A) was conducted with 3 pre-dose time points (2, 6 and 18 hrs). The second was conducted at 0, 1 and 2 hr predose time points. For both studies, drug was dosed IP or IV.

Using data from the first study, a second study was conducted that was designed to measure dose-response activity of each compound. Compounds were tested at doses of 0, 2.0 and 5 mg/kg using the route and pre-treatment time that produced the best activity.

LPS-stimulated increases in both TNFα and IL-1β to levels consistent with those of previous studies. Consistent with these previous studies, TNFα was much more responsive than IL-1β to these LPS-stimulated increases. Serum TNFα levels were increased from undetectable levels to between 3 and 8 ng/ml. IL-1β levels were elevated from baseline levels of between 50 and 100 pg/ml to an LPS-stimulated level of 200 to 350 pg/ml.

Both ICI-685 and ICI-735 inhibited LPS-stimulated TNFα secretion. For both compounds, the optimal pre-dose time period for TNFα inhibition was between 0 and 2 hrs with IV administration producing a slightly better inhibition than IP administration. For the subsequent dose-response study, animals were dosed with a pre-dose period of 1 hr via IV administration. The test drugs used in these studies did not inhibit LPS-mediated increases in IL-1β levels in a reproducible fashion. These data are consistent with our previous studies that demonstrate that IL-1β is less responsive than TNFα to the inhibitory activity of these class of molecules.

For the dose-response study, both compounds inhibited at concentrations of 5 mg/kg, but not at lower doses. In combination with the pre-dose time course (which were dosed at 10 mg/kg), it appears that the most active dose levels for both compounds are 10 mg/kg.

For the current studies, there appears to be a discrepancy between the two time courses. Specifically, in the first time course ICI-685 did not inhibit TNFα levels at the 2 hr pretreatment period (IV administration). However, in the second pre-dose time course study, ICI-685 inhibited TNFα by 70%. As will be understood by the skilled artisan, effective dose-ranges in this type of LPS study for any compound can fluctuate from 5 to 10 fold. Immune function and cytokine responsiveness can be altered by (for example) environmental conditions (previous and current), age of animals, feeding state, time of study and LPS preparation.

Pharmacological Evaluation of Compounds ICI-715, ICI-824, ICI-953 and ICI-954 in Model of LPS-Mediated Cytokine Production.

Compounds ICI-715, ICI-824, ICI-953 and ICI-954 were formulated in water. For the time course study, drugs were formulated at a concentration of 1 mg/ml and dosed 10 ml/kg to produce a dose of 10 mg/kg. For the dose-response study, drugs were formulated at concentrations of 0.05, 0.2 and 0.5 mg/ml and dosed at a volume of 10 ml/kg to produce doses of 0.5, 2 and 5 mg/kg, respectively. Animals were dosed IV or IP.

CD1:ICR mice were obtained from Harlan (Indianapolis, Ind.) at 6 weeks of age. Animals were housed 5 per cage, kept on a 12 hr light dark cycle and fed food and water ad libitum. Animals were tested at 8-10 weeks of age.

Lipopolysaccharide (heat killed E. coli 0127:B5; Sigma Aldrich) was prepared in distilled water at a concentration of 0.025 mg/ml. LPS was dosed at a volume of 10 ml/kg (IP) to produce a final dose of 0.25 mg/kg (approximately 7.5 μg/mouse). Drugs were dosed prior to LPS administration as indicated above. Blood was collected by retro-orbital eye bleed 90 minutes after LPS administration. Serum was prepared from blood and TNF-α and IL-1β levels were measured by using the OPT-EIA mouse TNF-α and IL-1β ELISA kits (BD Biosciences) as per directions of the manufacturer.

The first study was designed to determine the optimal route of administration and the optimal pre-treatment time. One pre-dose time course was conducted (for all compounds) with compounds administered at 0, 1 and 2 hrs prior to LPS treatment. For both studies, drug was dosed IP or IV. The IP study and IV study were conducted on separate days.

Using data from the first study, a second study was conducted that was designed to measure dose-response activity of each compound. Compounds were tested at doses of 0.5, 2.0 and 5 mg/kg using the route and pre-treatment time that produced the best activity.

In the present studies, LPS-stimulated increases in both TNFα and IL-1β to levelsconsistent with those of previous studies. Consistent with these previous studies, TNFα was much more responsive than IL-1β to these LPS-stimulated increases. Serum TNFα levels were increased from undetectable levels to between 1 and 7 ng/ml. IL-1β levelswere elevated from baseline levels of between 50 and 100 pg/ml to an LPS-stimulated level of 200 to 350 pg/ml.

All four compounds inhibited LPS-stimulated TNFα secretion. The optimal pre-dose time period for TNFα inhibition was 1 hr. IP administration produced slightly better inhibition than IV administration for ICI-824, ICI-953 and ICI-954. IV administration of ICI-715 produced slightly better inhibition than IV administration. This predose time period and these routes were selected for the subsequent dose-response analysis.

For the dose-response study, the dose-range was between 0.5 and 5 mg/kg. Administration of ICI-715 (IV) produced at least a 50% inhibition of TNFα at all doses tested. ICI-824, ICI-953 and ICI-954 (IP) were ineffective up to a dose of 5 mg/kg. In combination with the pre-dose time course (which were dosed at 10 mg/kg), it appears that the most active dose levels for these last three compounds are 10 mg/kg. It also appears that ICI-715 may be more potent than these other compounds. However, ICI-715 was dosed IV, and the other compounds were dosed IP.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inducing apoptosis in an immune cell, the method comprising contacting the immune cell with a compound of formula I:

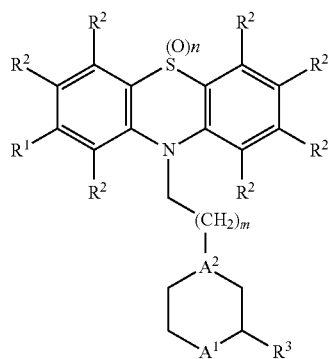

formula I or a pharmaceutically acceptable salt thereof, wherein:

$R^1$ is independently selected at each occurrence from hydrogen, halogen, $(C_1-C_6)$alkyl; $(C_1-C_6)$alkenyl; $(C_1-C_6)$alkoxy; OH; $NO_2$; C≡N; $C(=O)OR^7$; $C(=O)NR^7_2$; $NR^7_2$; $NR^7C(=O)(C_1-C_6)$alkyl; $NR^7C(=O)O(C_1-C_6)$alkyl; $NR^7C(=O)NR^7_2$; $NR^7SO_2(C_1-C_6)$alkyl; $SO_2NR^7_2$; $OC(=O)(C_1-C_6)$alkyl; $O(C_2-C_6)$alkylene-$NR^7_2$; $(C_2-C_6)$alkylene-$OR^7$; and $(C_1-C_3)$perfluoroalkyl;

$R^2$ is independently selected at each occurrence from hydrogen, halogen, $(C_1-C_6)$alkyl; $(C_1-C_6)$alkenyl; $(C_1-C_6)$alkoxy; OH; $NO_2$; C≡N; $C(=O)OR^7$; $C(=O)NR^7_2$; $NR^7_2$; $NR^7C(=O)(C_1-C_6)$alkyl; $NR^7C(=O)O(C_1-C_6)$alkyl; $NR^7C(=O)NR^7_2$; $NR^7SO_2(C_1-C_6)$alkyl; $SO_2NR^7_2$; $OC(=O)(C_1-C_6)$alkyl; $O(C_2-C_6)$alkylene-$NR^7_2$; $(C_2-C_6)$alkylene-$OR^7$; and $(C_1-C_3)$perfluoroalkyl;

$R^3$ is hydrogen, $C(=O)OR^7$, or $C(=O)NR^7_2$;

$A^1$ is $CH_2$ or $NR^4$;

$A^2$ is CH or N;

provided that if $A^1$ is $CH_2$, then $A^2$ is N, and if $A^2$ is CH, then $A^1$ is $NR^4$;

$R^4$ is $(CH_2)_p NHC(O)R^5$; $(CH_2)_p O(CH_2)_p OR^7$; $(CH_2)_p O(CH_2)_p NR^7_2$; $(CH_2)_p NR^4(CH_2)_p NR^7_2$; $(CH_2)_p O(CH_2)_p NHC(O)R^5$; $(CH_2)_p NR^7(CH_2)_p NHC(O)R^5$; $(CH_2)_q C(=O)OR^7$; $(CH_2)_q C(=O)NR^7_2$; $(CH_2)_p O(CH_2)_q C(=O)OR^7$; $(CH_2)_p O(CH_2)_q C(=O)NR^7_2$; $(CH_2)_p NR^7(CH_2)_q C(=O)OR^7$; or $(CH_2)_p NR^7(CH_2)_q C(=O)NR^7_2$;

$R^5$ is $(C_1-C_6)$alkyl; $NR^7C(=O)(C_1-C_6)$alkyl; $NR^7C(=O)O(C_1-C_6)$alkyl; $NR^7C(=O)NR^7_2$; $CH(R^6)NR^7_2$; $CH(R^6)NR^7C(=O)(C_1-C_6)$alkyl; or $CH(R^6)NR^7C(=O)O(C_1-C_6)$alkyl;

$R^6$ is H, $(C_1-C_6)$alkyl; $(C_2-C_6)$alkylene-$OR^7$; $(CH_2)_q C(=O)OR^7$; or $(CH_2)_q C(=O)NR^7_2$;

$R^7$ is independently selected at each occurrence from the group consisting of hydrogen and $(C_1-C_6)$alkyl;

m is independently at each occurrence 1, 2, or 3;

n is 0, 1, or 2;

p is independently at each occurrence 2 or 3; and q is independently at each occurrence 1 or 2.

2. The method of claim 1, wherein the compound of formula I is selected from the group consisting of:

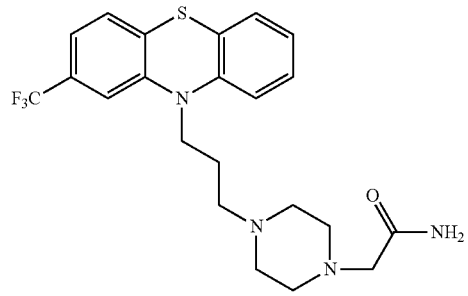

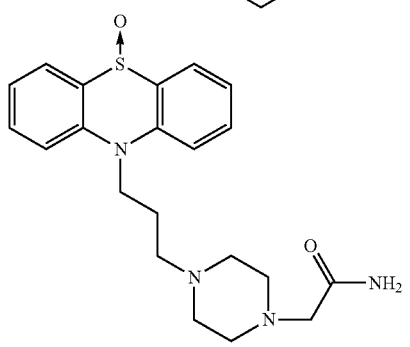

57
-continued
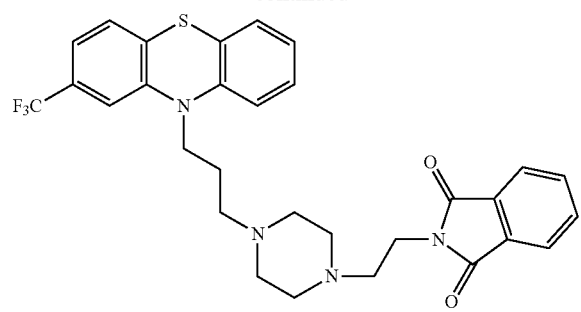
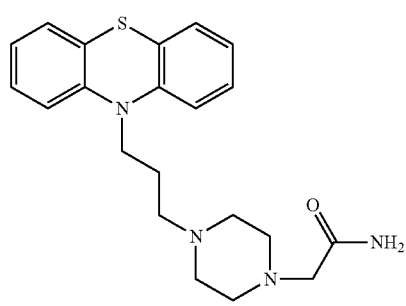
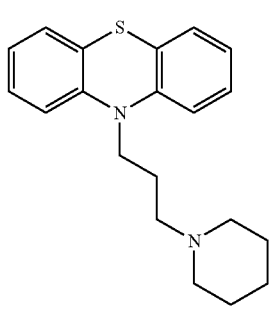
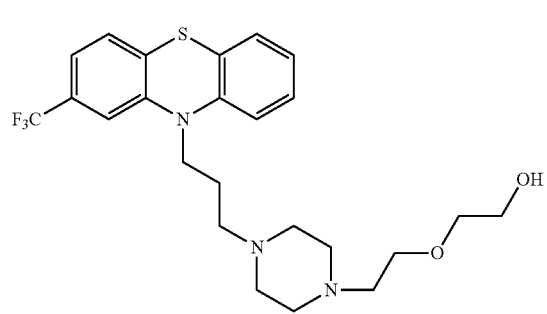
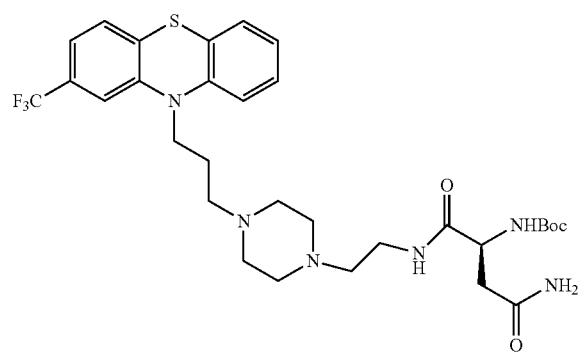
58
-continued
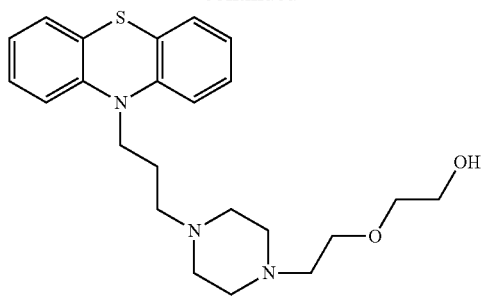
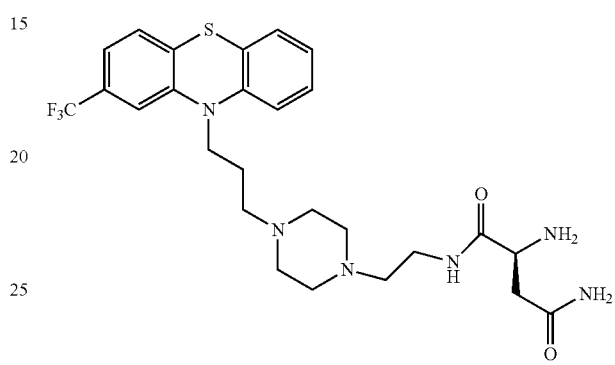
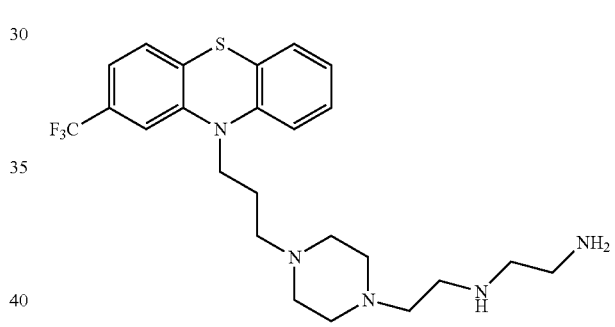
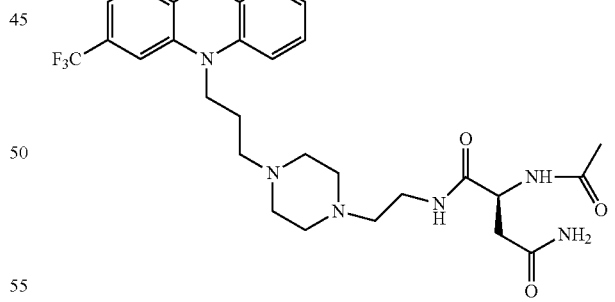
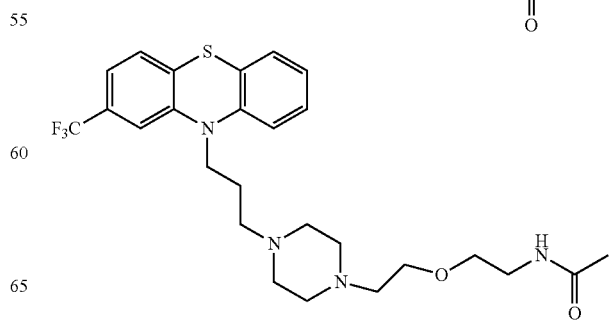

59
-continued
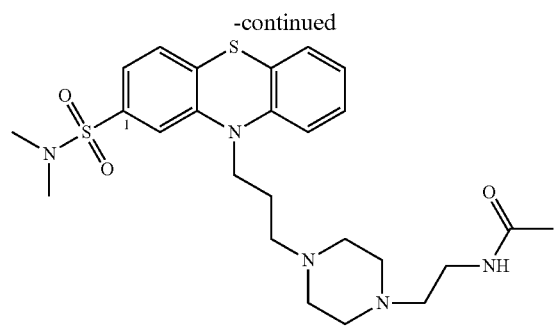
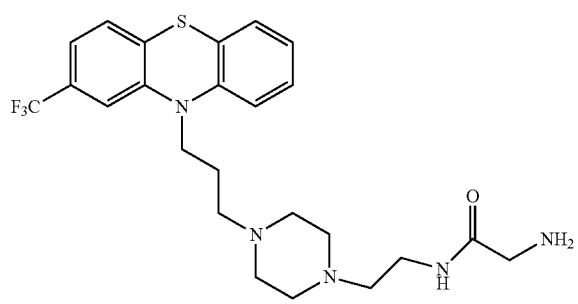
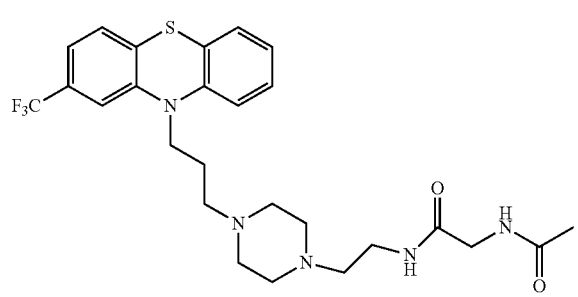
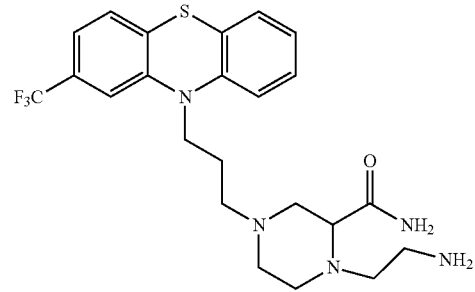
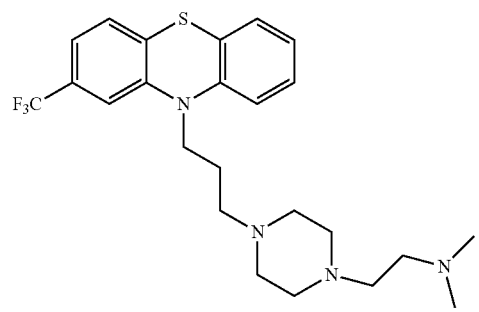
60
-continued
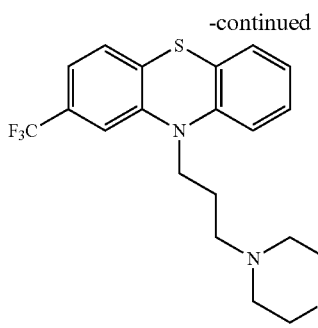
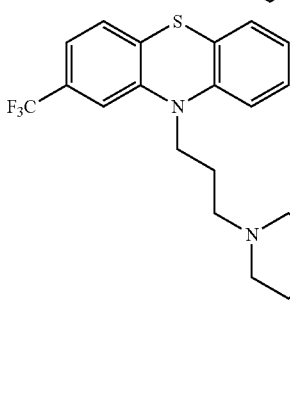
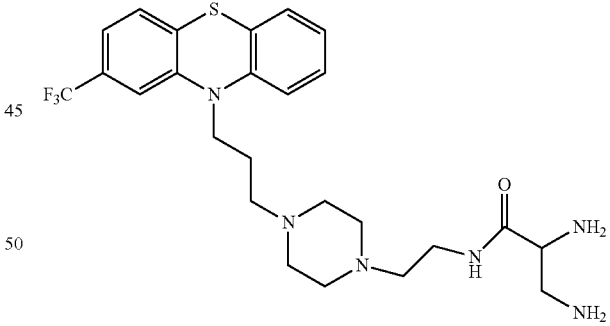
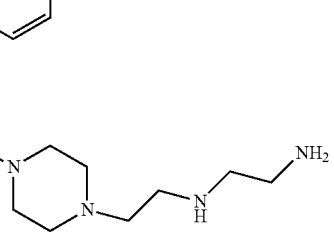

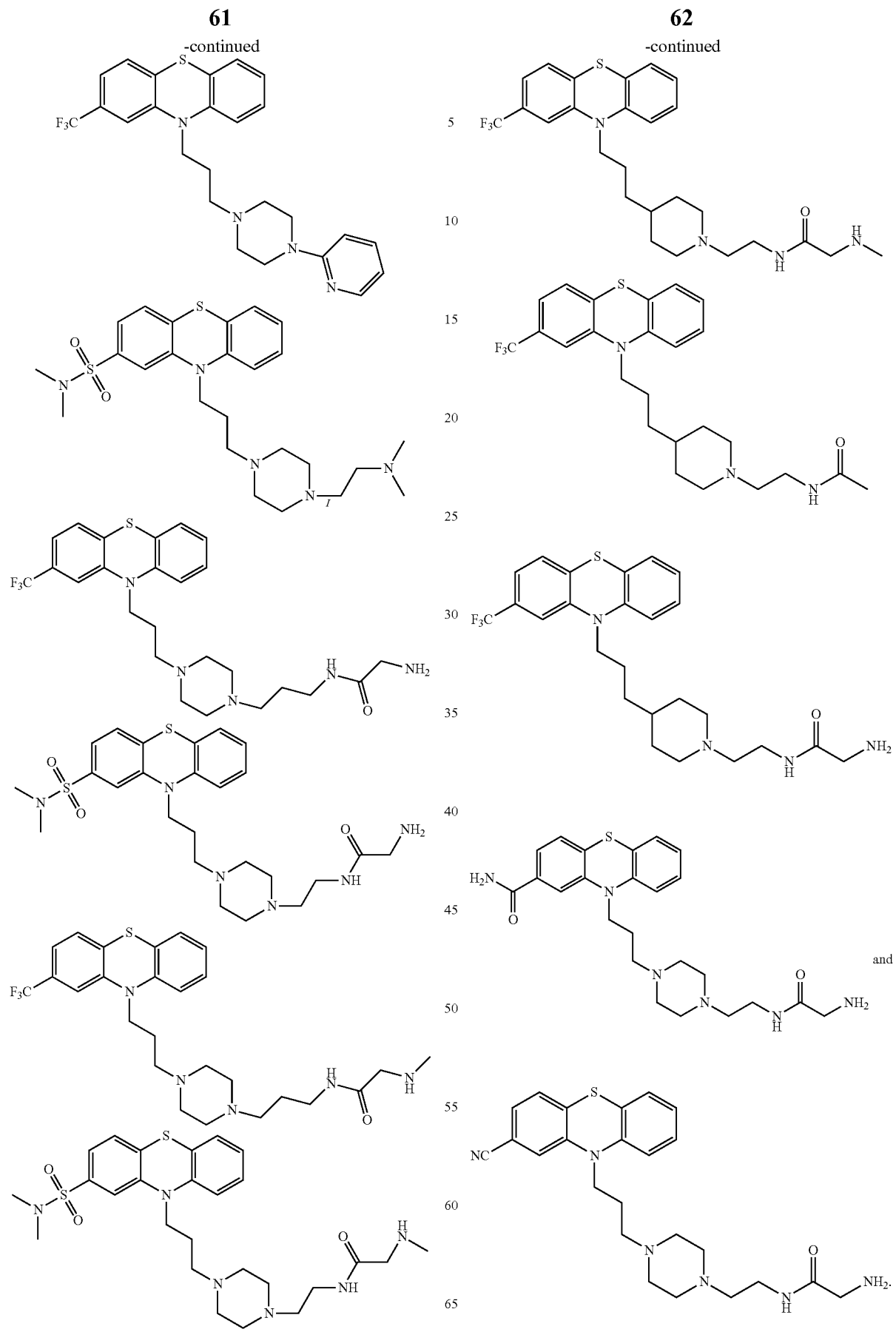

3. A method of inducing apoptosis in a lymphocyte, the method comprising contacting the lymphocyte with a compound of formula I.

4. The method of claim 3, wherein the lymphocyte is selected from the group consisting of a T cell and a B cell.

5. The method of claim 4, wherein the B cell is a plasma cell.

6. The method of claim 5, wherein the plasma cell is a multiple myeloma cell.

7. A method of inhibiting proliferation of a lymphocyte, the method comprising contacting the lymphocyte with a compound of formula I.

8. The method of claim 7, wherein the lymphocyte is selected from the group consisting of a T cell and a B cell.

9. The method of claim 8, wherein the B cell is a plasma cell.

10. The method of claim 9, wherein the plasma cell is a multiple myeloma cell.

11. The method of claim 1, wherein the compound of formula I is

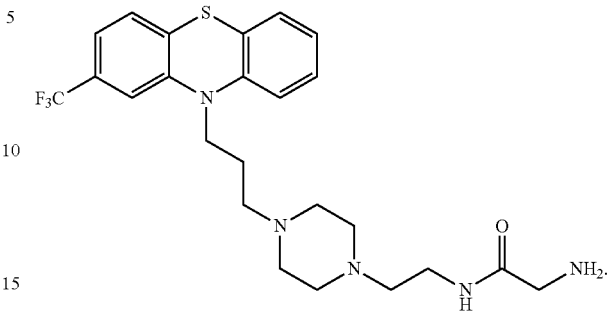

* * * * *